US010167345B2

(12) United States Patent
Baty et al.

(10) Patent No.: US 10,167,345 B2
(45) Date of Patent: Jan. 1, 2019

(54) ANTIGEN BINDING FORMATS FOR USE IN THERAPEUTIC TREATMENTS OR DIAGNOSTIC ASSAYS

(71) Applicants: Daniel Baty, Marseilles (FR); Patrick Chames, Marseilles (FR); Martine Mansais, Marseilles (FR); Brigitte Kerfelec, Marseilles (FR); Caroline Rozan, Marseilles (FR)

(72) Inventors: Daniel Baty, Marseilles (FR); Patrick Chames, Marseilles (FR); Martine Mansais, Marseilles (FR); Brigitte Kerfelec, Marseilles (FR); Caroline Rozan, Marseilles (FR)

( * ) Notice: Subject to any disclaimer, the term of this patent is extended or adjusted under 35 U.S.C. 154(b) by 142 days.

(21) Appl. No.: 15/421,559

(22) Filed: Feb. 1, 2017

(65) Prior Publication Data

US 2017/0152324 A1 Jun. 1, 2017

Related U.S. Application Data

(62) Division of application No. 13/976,481, filed as application No. PCT/EP2011/074241 on Dec. 29, 2011, now Pat. No. 9,598,499.

(60) Provisional application No. 61/428,294, filed on Dec. 30, 2010.

(30) Foreign Application Priority Data

Dec. 30, 2010 (EP) .................................... 10306541

(51) Int. Cl.

| | |
|---|---|
| ***C07K 16/46*** | (2006.01) |
| ***C07K 16/28*** | (2006.01) |
| ***C07K 16/30*** | (2006.01) |

(52) U.S. Cl.

CPC .......... *C07K 16/468* (2013.01); *C07K 16/283* (2013.01); *C07K 16/3007* (2013.01); *C07K 2317/22* (2013.01); *C07K 2317/31* (2013.01); *C07K 2317/35* (2013.01); *C07K 2317/52* (2013.01); *C07K 2317/522* (2013.01); *C07K 2317/569* (2013.01); *C07K 2317/64* (2013.01); *C07K 2317/73* (2013.01); *C07K 2317/92* (2013.01); *C07K 2317/94* (2013.01); *C07K 2319/00* (2013.01); *C07K 2319/74* (2013.01)

(58) Field of Classification Search

None

See application file for complete search history.

(56) References Cited

FOREIGN PATENT DOCUMENTS

WO WO 2006/064136 * 6/2006 ............ C07K 16/00

OTHER PUBLICATIONS

Borchmann et al. (Blood, 100(9): 3101-3107, 2002).*

* cited by examiner

*Primary Examiner* — Nelson B Moseley, II

(74) *Attorney, Agent, or Firm* — Whitham & Cook, P.C.

(57) ABSTRACT

The present invention relates to antigen binding formats for use in therapeutic treatments or diagnostic assays. The present invention relates to an antigen-binding format consisting of: —a first fusion protein wherein the CH1 constant domain of an antibody is fused i) by its N-terminal end to the C-terminal end of a variable domain of an antibody and ii) by its C-terminal end to the N-terminal end of a variable domain of an antibody and, —a second fusion protein wherein the CL constant domain of an antibody is fused by its N-terminal end to the C-terminal end of a variable domain of an antibody.

4 Claims, 3 Drawing Sheets

Figure 1:
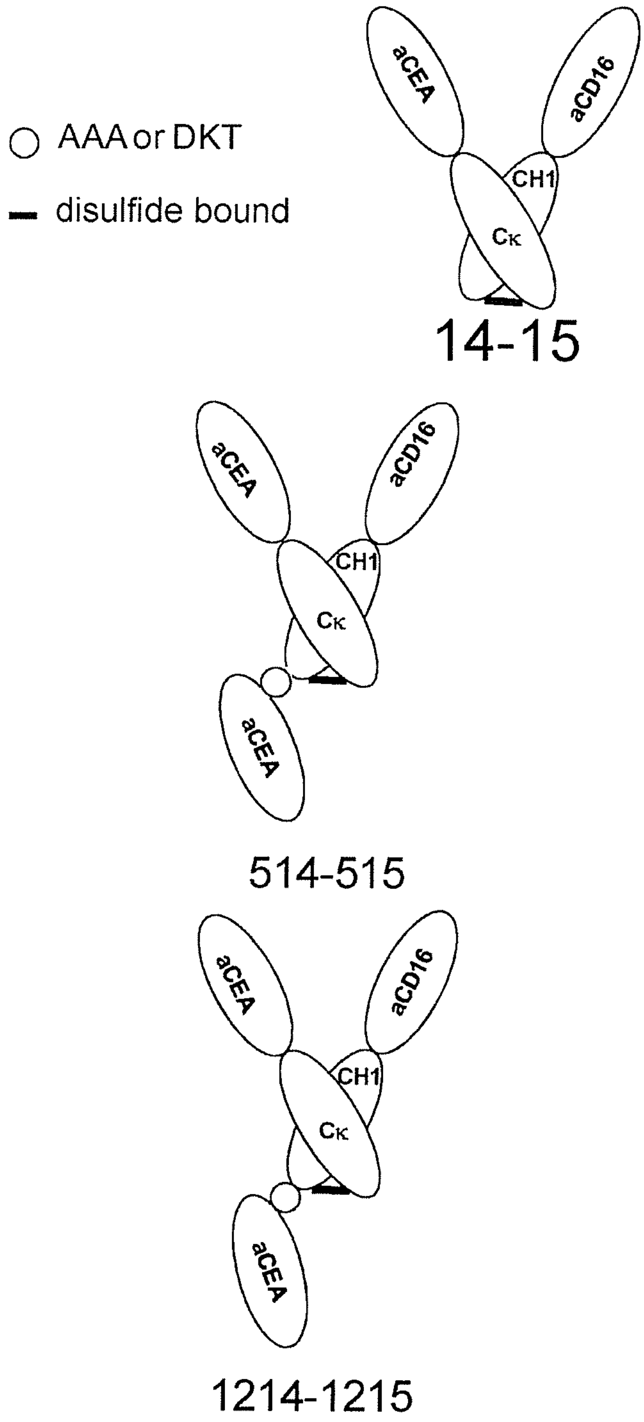

Specification includes a Sequence Listing.

ANTIGEN BINDING FORMATS FOR USE IN THERAPEUTIC TREATMENTS OR DIAGNOSTIC ASSAYS

CROSS-REFERENCE TO RELATED APPLICATIONS

This application is divisional application of U.S. patent application Ser. No. 13/976,481 filed Jun. 27, 2013, and that application was a Rule 371 national stage filing from PCT/EP2011/074241 filed Dec. 29, 2011, which claimed priority to U.S. Provisional Application 61/428,294 filed Dec. 30, 2010 and European Application 10306541.3 filed Dec. 30, 2010.

FIELD OF THE INVENTION

The present invention relates to antigen binding formats for use in therapeutic treatments or diagnostic assays.

BACKGROUND OF THE INVENTION

Therapeutic monoclonal antibodies (mAbs) have met some successes in the clinic over the last years, particularly in oncology. More than twenty five mAbs are on the market.

Many technical efforts have been made to generate second generation mAbs with decreased immunogenicity and with optimized effector functions. Since the majority of therapeutic antibodies are IgG1, at least part of the observed in vivo effects of mAbs might be induced following interactions between their Fc region and FcγR. Notably, the ability of mAbs to kill tumor cells has been related to their capacity to recruit and activate effector cells such as NK cells and macrophages through receptors for the Fc portion of IgG (FcγR).

However, recent reports have shown that the efficiency of IgG1 human therapeutic mAbs is strongly affected by various parameters: changes in Fc glycosylation, FcγRIIIA polymorphism, interaction with inhibitory FcγRIIB, and competition with endogenous IgG for FcγRI and FcγRIII binding. For instance, studies with FcγR−/− mice have revealed the implication of different FcγR in some in vivo mechanisms of action of two widely used therapeutic mAbs, trastuzumab and rituximab. These cytotoxic mAbs directed against tumors engage both activating (FcγRIIIA) and inhibitory (FcγRIIB) receptors. In these studies, a more pronounced tumor regression was observed in FcγRIIB-deficient mice than in wild-type mice, whereas FcγRIIIA-deficient mice were unable to stop tumor growth in the presence of therapeutic mAbs. In humans, a recent study has shown that the therapeutic efficiency of rituximab (a chimeric human IgG1) in patients with non-Hodgkin lymphoma is partly correlated with FcγRIIIA polymorphism. Thus, patients homozygous for the Val158 allele (IgG1 high binder) exhibited a higher response to the treatment than the patients homozygous for the Phe158 allele (IgG1 low binder). Similarly, engineered IgG glycoforms have been shown to trigger optimized ADCC through the recruitment of FcγRIIIA. A first study showed that an IgG1 antibody engineered to contain increasing amounts of bisected complex oligosaccharides (bisecting N-acetylglucosamine, GlcNAC) allows the triggering of a strong ADCC as compared to its parental counterpart. Second, a lack of fucose or low fucose content on human IgG1 N-linked oligosaccharides has been shown to improve FcγRIIIA binding and ADCC as well as to increase the clearance rate of Rhesus D+ red blood cells in human volunteers. Moreover, it has been recently shown that the antigenic density required to induce an efficient ADCC is lower when the IgG has a low content in fucose as compared to a highly fucosylated IgG.

The idea that a better control of Fc/FcγR interactions was needed when using therapeutic mAbs has been clearly argued in the early 80's and led to the concept and the generation of bispecific antibodies (bsAbs), using biochemical approaches and then molecular engineering in the early 90's. Bispecific antibodies, able to bring together target cells and activated effector cells have important potential advantages over whole naked mAbs. Notably, with regard to NK cells recruitment and activation, bsAbs make it possible to overcome most of the problems encountered with therapeutic mAbs. First, it is far easier to use an antibody arm binding to FcγRIIIA than to engineer and fine-tune the interaction between the antibody Fc region and FcγRIIIA. It is indeed possible to select a FcγRIIIA binder devoid of cross reaction for inhibitory FcγRIIB and targeting an epitope not involved in the Fc binding to avoid the high/low binder FcγRIIIA polymorphism issue, as well as endogenous IgG competition. Moreover, antibody fragments are not concerned by glycosylation issues, and it is possible to fine-tune the affinity of the antibody from a μM to a nM range, i.e., an affinity up to 1,000 fold higher than that involved in Fc/FcγRIIIA interaction. Thus, a number of attempts have been made to create anti-FcγRIIIA×anti-target bsAbs.

However, for years, these attempts were hindered by the impossibility to efficiently produce such molecules, the most efficient techniques requiring grams of mAbs to produce milligrams of heterogeneous preparations of bsAbs. Therefore, the first generation of bsAbs never reached the market, mostly due to the cost of getting molecules with bi-functional properties in large amounts for a therapeutic use.

The inventors have recently developed a new generation of bispecific antibodies, based on llama VHH (sdAb for single domain antibody or also Nb for nanobody), that can be easily produced in *E. coli* and that overcome the limitations listed above, while being able to exert a strong tumor lysis at extremely low concentrations. These bispecific antibodies are described in the International Patent Application no WO/2006/064136. This generation of therapeutic antibodies has the potential to rapidly translate into efficient therapeutics. Although these bsAbs accumulate within the tumor, they suffer from a rapid elimination due to their relatively small size, below the renal threshold (around 60 kDa), and to the absence of Fc region involved in the interaction with the FcRn receptor, responsible for the long serum half-life of full length IgG. Thus, there is a need to improve these bsAbs in terms of efficiency, serum half-life and biodistribution.

SUMMARY OF THE INVENTION

The present invention relates to an antigen-binding format consisting of:

- a first fusion protein wherein the CH1 constant domain of an antibody is fused i) by its N-terminal end to the C-terminal end of a first variable domain of an antibody and ii) by its C-terminal end to the N-terminal end of a second variable domain of an antibody and,
- a second fusion protein wherein the CL constant domain of an antibody is fused by its N-terminal end to the C-terminal end of a third variable domain of an antibody.

DETAILED DESCRIPTION OF THE INVENTION

The inventors have now created new antigen binding formats to increase the serum half-life of the original bsAb format (54 kDa) described in the International Patent Application WO/2006/064136 by fusing one additional sdAb (single domain antibody) to the C-terminal end of the CH1 domain of the Cκ/CH1 heterodimerization motif (FIG. 1). They have surprisingly shown that said fusion allows the production of various functional antigen binding formats differing in size and valence for the targeted antigens. The fact that sdAbs fused via their N-terminal domain to the C-terminal domain of CH1 remain active is remarkable because this N-terminal end is located at the vicinity of the antigen binding site. Major steric hindrance between the antigen and the heterodimerization motif might have occurred. However the inventors demonstrated that functional antigen binding formats may be obtained.

Antigen-Binding Formats of the Invention

Accordingly, the present invention relates to an antigen-binding format consisting of:

- a first fusion protein wherein the CH1 constant domain of an antibody is fused i) by its N-terminal end to the C-terminal end of a variable domain of an antibody and ii) by its C-terminal end to the N-terminal end of a variable domain of an antibody and,
- a second fusion protein wherein the CL constant domain of an antibody is fused by its N-terminal end to the C-terminal end of a variable domain of an antibody.

According to the invention, the antigen binding format of the invention represents a heterodimeric format that reproduces the CL/CH1 heterodimerization motif of a classic antibody and thus allows the correct folding of the antigen binding formats of the invention in a cellular context. According to the invention, the CH1 constant domain of the first fusion protein and the CL constant domain of the second fusion protein are therefore linked together via a disulfide bond.

According to the present invention, "antibody" or "immunoglobulin" have the same meaning, and will be used equally in the present invention. In natural antibodies, the two heavy chains are linked to each other by disulfide bonds and each heavy chain is linked to a light chain by a disulfide bond. There are two types of light chain, lambda (λ) and kappa (κ). There are five main heavy chain classes (or isotypes) which determine the functional activity of an antibody molecule: IgM, IgD, IgG, IgA and IgE. Each chain contains distinct sequence domains. The light chain includes two domains, a variable domain (VL) and a constant domain (CL). The heavy chain includes four domains, a variable domain (VH) and three constant domains (CH1, CH2 and CH3, collectively referred to as CH). The variable regions of both light (VL) and heavy (VH) chains determine binding recognition and specificity to the antigen. The constant region domains of the light (CL) and heavy (CH) chains confer important biological properties such as antibody chain association, secretion, transplacental mobility, complement binding, and binding to Fc receptors. The Fv fragment is the N-terminal part of the Fab fragment of an immunoglobulin consisting of the variable domains of one light chain and one heavy chain. The specificity of the antibody resides in the structural complementarity between the antibody combining site and the antigenic determinant. Antibody combining sites are made up of residues that are primarily from the hypervariable or complementarity determining regions (CDRs). Occasionally, residues from non-hypervariable or framework regions (FR) influence the overall domain structure and hence the combining site. The CDR refers to amino acid sequences which together define the binding affinity and specificity of the natural Fv region of a native immunoglobulin binding site. The light and heavy chain variable domains of an immunoglobulin have three CDRs, designated L-CDR1, L-CDR2, L-CDR3 and H-CDR1, H-CDR2, H-CDR3, respectively. An antigen-binding site, therefore, includes six CDRs, comprising the CDR set from each of a heavy and a light chain V region. FR refers to amino acid sequences interposed between CDRs.

The term "monoclonal antibody" or "mAb" as used herein refers to an antibody molecule of a single amino acid composition, that is directed against a specific antigen and that is produced by a single clone of B cells or hybridoma. Accordingly, the term "hybridoma" denotes a cell, which is obtained by subjecting a B cell prepared by immunizing an animal with an antigen to cell fusion with a myeloma cell derived from a mouse or the like which produces a desired monoclonal antibody having an antigen specificity.

In a particular embodiment, the CH1 and CL constant domains of the invention are humanized constant domains, and more preferably full-human CH1 and CL constant domains.

By "humanized", it is meant mutated so that immunogenicity upon administration in human patients is minor or nonexistent. Humanizing an antibody (e.g. a murine or Camelid antibody), according to the present invention, comprises a step of replacing one or more of the amino acids of said antibody by their human counterpart as found in the human consensus sequence, without that antibody losing its typical character, i. e. the humanization does not significantly affect the antigen binding capacity of the resulting antibody.

In a particular embodiment, the CL domain is from a lambda (λ) or a kappa (κ) light chain.

In a particular embodiment, the CH1 domain is from an IgG, such as IgG1, IgG2, IgG3, or IgG4. Alternatively, the CH1 domain is from an IgA, IgD, IgE or IgM.

In a particular embodiment, the variable domain is selected from the group consisting of VH domains, VL domains, or single domain antibodies (sdAbs).

The term "single domain antibody" (sdAb) or "VHH" refers to the single heavy chain variable domain of antibodies of the type that can be found in Camelid mammals which are naturally devoid of light chains. Such VHH are also called "Nanobody®". According to the invention, sdAb can particularly be llama sdAb.

In a particular embodiment, the single domain antibody (VHH) domain is humanized.

In a particular embodiment, the variable domain is a VH domain or a single domain antibody (sdAb).

In a particular embodiment, the VH domain is a humanized VH domain, and more preferably a fully human VH domain.

Typically, the variable domain may be directed against any antigen.

For example, the variable domain may be specific for an immune cell regulatory molecule such as CD3, CD4, CD8, CD25, CD28, CD26, CTLA-4, ICOS, or CD11a. Other suitable antigens include but are not limited to those associated with immune cells including T cell-associated molecules, such as TCR/CD3 or CD2; NK cell-associated targets such as NKG2D, FcγRIIIa (CD16), CD38, CD44, CD56, or CD69; granulocyte-associated targets such as FcγRI (CD64), FcαRI (CD89), and CR3 (CD11b/CD18); monocyte/macrophage-associated targets (such as FcγRI (CD64), FcαRI (CD89), CD3 (CD11b/CD18), or mannose receptor; dendritic cell-associated targets such as FcγRI (CD64) or mannose receptor; and erythrocyte-associated targets such as CRI (CD35).

Alternatively, the variable domain according to the invention may be directed against a cancer antigen. Known cancer antigens include, without limitation, c-erbB-2 (erbB-2 is also known as c-neu or HER-2), which is particularly associated with breast, ovarian, and colon tumor cells, as well as neuroblastoma, lung cancer, thyroid cancer, pancreatic cancer, prostate cancer, renal cancer and cancers of the digestive tract. Another class of cancer antigens is oncofetal proteins of nonenzymatic function. These antigens are found in a variety of neoplasms, and are often referred to as "tumor-associated antigens." Carcinoembryonic antigen (CEA), and α-fetoprotein (AFP) are two examples of such cancer antigens. AFP levels rise in patients with hepatocellular carcinoma: 69% of patients with liver cancer express high levels of AFP in their serum. CEA is a serum glycoprotein of 200 kDa found in adenocarcinoma of colon, as well as cancers of the lung and genitourinary tract. Yet another class of cancer antigens is those antigens unique to a particular tumor, referred to sometimes as "tumor specific antigens," such as heat shock proteins (e.g., hsp70 or hsp90 proteins) from a particular type of tumor. Other targets include the MICA/B ligands of NKG2D. These molecules are expressed on many types of tumors, but not normally on healthy cells.

Additional specific examples of cancer antigens include epithelial cell adhesion molecule (Ep-CAM/TACSTD1), mesothelin, tumor-associated glycoprotein 72 (TAG-72), gp100, Melan-A, MART-1, KDR, RCAS1, MDA7, cancer-associated viral vaccines (e.g., human papillomavirus antigens), prostate specific antigen (PSA, PSMA), RAGE (renal antigen), CAMEL (CTL-recognized antigen on melanoma), CT antigens (such as MAGE-B5, -B6, -C2, -C3, and D; Mage-12; CT10; NY-ESO-1, SSX-2, GAGE, BAGE, MAGE, and SAGE), mucin antigens (e.g., MUC1, mucin-CA125, etc.), cancer-associated ganglioside antigens, tyrosinase, gp75, C-myc, Mart1, MelanA, MUM-1, MUM-2, MUM-3, HLA-B7, Ep-CAM, tumor-derived heat shock proteins, and the like (see also, e.g., Acres et al., Curr Opin Mol Ther 2004 February, 6:40-7; Taylor-Papadimitriou et al., Biochim Biophys Acta. 1999 Oct. 8; 1455(2-3):301-13; Emens et al., Cancer Biol Ther. 2003 July-August; 2(4 Suppl 1):S161-8; and Ohshima et al., Int J Cancer. 2001 Jul. 1; 93(1):91-6). Other exemplary cancer antigen targets include CA 195 tumor-associated antigen-like antigen (see, e.g., U.S. Pat. No. 5,324,822) and female urine squamous cell carcinoma-like antigens (see, e.g., U.S. Pat. No. 5,306,811), and the breast cell cancer antigens described in U.S. Pat. No. 4,960,716.

The variable domain according to the invention may target protein antigens, carbohydrate antigens, or glycosylated proteins. For example, the variable domain can target glycosylation groups of antigens that are preferentially produced by transformed (neoplastic or cancerous) cells, infected cells, and the like (cells associated with other immune system-related disorders). In one aspect, the antigen is a tumor-associated antigen. In an exemplary aspect, the antigen is O-acetylated-GD2 or glypican-3. In another particular aspect, the antigen is one of the Thomsen-Friedenreich (TF) antigens (TFAs).

The variable domain according to the invention can also exhibit specificity for a cancer-associated protein. Such proteins can include any protein associated with cancer progression. Examples of such proteins include angiogenesis factors associated with tumor growth, such as vascular endothelial growth factors (VEGFs), fibroblast growth factors (FGFs), tissue factor (TF), epidermal growth factors (EGFs), and receptors thereof; factors associated with tumor invasiveness; and other receptors associated with cancer progression (e.g., one of the HER1-HER4 receptors).

Alternatively the variable domain according to the invention can be specific for a virus, a bacteria or parasite associated target. For example, the variable domain may be specific for a virus-associated target such as an HIV protein (e.g., gp120 or gp41), CMV or other viruses, such as hepatitis C virus (HCV).

The variable domain according to the invention may also target albumin or FcRn to increase the half-life of the antigen binding formats of the invention in the systemic circulation.

The variable domain according to the invention may alternatively target a hapten, and more particularly low molecular weight hapten, and more preferably a radiolabeled low molecular weight hapten. Molecular weight haptens according to the invention may be selected from the group consisting of methotrexate, histamine succinyl glycine, DTPA (diethylene triaminepentaacetic acid); DOTA (1,4,7,10-tetraazacyclododecane-N,N',N",N'"-tetraacetic acid); and derivatives thereof (see, for example, U.S. Pat. Nos. 4,885,363; 5,087,440; 5,155,215; 5,188,816; 5,219,553; 5,262,532; and 5,358,704; and D. Meyer et al., Invest. Radiol. 1990, 25: S53-55). In particular embodiment, the hapten is labeled with a radionuclide. For example, useful diagnostic radionuclides include, but are not limited to, $^{110}$In, $^{177}$Lu, $^{18}$F, $^{52}$Fe, $^{62}$Cu, $^{64}$Cu, $^{67}$Cu, $^{67}$Ga, $^{68}$Ga, $^{89}$Zr, $^{94}$Tc, $^{150}$Re, $^{188}$Re, or other gamma-, beta-, or positron-emitters. Particularly useful therapeutic radionuclides include, but are not limited to $^{111}$In, $^{177}$Lu, $^{212}$Bi, $^{213}$Bi, $^{211}$At, $^{62}$Cu, $^{64}$Cu, $^{67}$Cu, $^{90}$Y, $^{125}$I, $^{131}$I, $^{32}$P, $^{33}$P, $^{47}$Sc, $^{111}$Ag, $^{67}$Ga, $^{142}$Pr, $^{153}$Sm, $^{161}$Tb, $^{166}$Dy, $^{166}$Ho, $^{186}$Re, $^{188}$Re, $^{189}$Re, $^{212}$Pb, $^{223}$Ra, $^{225}$Ac, $^{59}$Fe, $^{75}$Se, $^{77}$As, $^{89}$Sr, $^{99}$Mo, $^{105}$Rh, $^{109}$Pd, $^{143}$Pr, $^{149}$Pm, $^{169}$Er, $^{194}$Ir, $^{198}$Au, $^{199}$Au, and $^{211}$Pb.

The constant domains and variable domains according to the invention can readily be prepared by an ordinarily skilled artisan using routine experimentation.

For example, the constant domains and variable domains according to the invention may be from monoclonal antibodies. Monoclonal antibodies directed against antigens of interest can be produced by an animal (including, but not limited to, human, mouse, camelid, rat, rabbit, hamster, goat, horse, chicken, or turkey), chemically synthesized, or recombinantly expressed. For example, monoclonal antibodies can be prepared and isolated using any technique that provides for the production of antibody molecules by continuous cell lines in culture. Techniques for production and isolation include but are not limited to the hybridoma technique originally described by Kohler and Milstein (1975); the human B-cell hybridoma technique (Cote et al., 1983); and the EBV-hybridoma technique (Cole et al. 1985). Other known methods of producing transformed B cell lines that produce monoclonal antibodies may also be used. Monoclonal antibodies of the present invention may be produced by recombinant DNA techniques, for example, produced by phage display or by combinatorial methods. See, for example, U.S. Pat. No. 5,223,409; WO 92/18619; WO 91/17271; WO 92/20791; WO 92/15679; WO 93/01288; WO 92/01047; WO 92/09690; or WO 90/02809. Monoclonal antibodies of the present invention can be purified by any method known in the art for purification of an immunoglobulin molecule, for example, by chromatography (e.g., ion exchange, affinity, and sizing column chromatography), centrifugation, differential solubility, or by any other standard technique for the purification of proteins. In addition, the antibodies can be fused to heterologous polypeptide sequences described herein or otherwise known in the art, to facilitate purification. Finally, the genes encoding the constant domain or variable domain according to the invention can be recovered from the DNA of relevant hybridomas or phages. In a particular embodiment, monoclonal antibodies are full-human antibodies or humanized antibodies.

sdAbs are usually generated by PCR cloning of the V-domain repertoire from blood, lymph node, or spleen cDNA obtained from immunized animals into a phage display vector, such as pHEN2. Antigen-specific sdAbs are commonly selected by panning phage libraries on immobilized antigen, e.g., antigen coated onto the plastic surface of a test tube, biotinylated antigens immobilized on streptavidin beads, or membrane proteins expressed on the surface of cells. However, such sdAbs often show lower affinities for their antigen than sdAbs derived from animals that have received several immunizations. The high affinity of sdAbs from immune libraries is attributed to the natural selection of variant sdAbs during clonal expansion of B-cells in the lymphoid organs of immunized animals. The affinity of sdAbs from non-immune libraries can often be improved by mimicking this strategy in vitro, i.e., by site directed mutagenesis of the CDR regions and further rounds of panning on immobilized antigen under conditions of increased stringency (higher temperature, high or low salt concentration, high or low pH, and low antigen concentrations). sdAbs derived from camelid are readily expressed in and purified from the *E. coli* periplasm at much higher levels than the corresponding domains of conventional antibodies. sdAbs generally display high solubility and stability and can also be readily produced in yeast, plant, and mammalian cells. For example, the "Hamers patents" describe methods and techniques for generating VHH against any desired target (see for example U.S. Pat. No. 5,800,988; U.S. Pat. No. 5,874,541 and U.S. Pat. No. 6,015,695). The "Hamers patents" more particularly describe production of sdAbs in bacterial hosts such as *E. coli* (see for example U.S. Pat. No. 6,765,087) and in lower eukaryotic hosts such as moulds (for example *Aspergillus* or *Trichoderma*) or in yeast (for example *Saccharomyces, Kluyveromyces, Hansenula* or *Pichia*) (see for example U.S. Pat. No. 6,838,254). In a specific antibody, the sdAbs of the invention may be further humanized.

According to the invention, the CH1 and CL constant domains of the fusion proteins are fused directly at their N-terminal ends to the C-terminal end of a variable domain of an antibody.

As used herein, the term "directly" means that the (first or last) amino acid at the terminal end (N or C-terminal end) of the constant domain is fused to the (first or last) amino acid at the terminal end (N or C-terminal end) of the variable domain.

In other words, in this embodiment, the first amino acid of the N-terminal end of said CH1 or CL constant domain is directly linked by a covalent bond to the last amino acid of the C-terminal end of said variable domain of an antibody.

According to the invention, the CH1 constant domain of the first fusion protein is fused by its C-terminal end to the N-terminal end of a variable domain of an antibody either directly or via a spacer.

As used herein, the term "spacer" refers to a sequence of at least one amino acid that links the constant domain with the variable domain of the invention. Such a spacer may be useful to prevent steric hindrances. Typically, said spacer is an amino acid sequence selected from the group consisting of AAA (SEQ ID NO:29) and DKT (SEQ ID NO:30). Preferably, said spacer is the sequence DKT naturally present at the C-terminal end of the human CH1 domain of antibodies.

Preferably, the antigen binding format according to the invention consists of:

- a first fusion protein consisting of a CH1 domain of an antibody fused directly by its N-terminal end to the C-terminal end of a variable domain of an antibody, and fused via a spacer by its C-terminal end to the N-terminal end of a variable domain of an antibody, said spacer being preferably AAA or DKT and,
- a second fusion protein consisting of a CL domain of an antibody fused directly by its N-terminal end to the C-terminal end of a variable domain of an antibody.

According to the invention, the antigen binding formats of the invention have 3 variable domains and can therefore be mono, bi, or tri specific toward antigens of interest. Accordingly, every variable domains of the antigen binding format according to the invention has the ability to bind to an antigen by itself. The binding to the antigen is not as the same as classically observed for an antibody binding to an antigen (the entity responsible for the binding to the antigen is the complex formed by the VL and CH variable domains) but approaches to the same as observed for camelid mammals: a variable domain (VH, VL or VHH) can bind to an antigen by itself.

In a particular embodiment, the present invention relates to an antigen-binding format consisting of:

- a first fusion protein wherein the CH1 constant domain of an antibody is fused i) by its N-terminal end to the C-terminal end of a variable domain of an antibody and ii) by its C-terminal end to the N-terminal end of a variable domain of an antibody and,
- a second fusion protein wherein the CL constant domain of an antibody is fused by its N-terminal end to the C-terminal end of a variable domain of an antibody.

with the exception of an antigen-binding format consisting of:

- a first fusion protein wherein the CH1 constant domain of an antibody is fused i) by its N-terminal end to the C-terminal end of a VH variable domain of an antibody and ii) by its C-terminal end to the N-terminal end of a variable domain of an antibody and,
- a second fusion protein wherein the CL constant domain of an antibody is fused by its N-terminal end to the C-terminal end of a VL variable domain of an antibody
- wherein the VH variable domain of the first fusion protein and VL variable domain of the second fusion protein do not constitute a unique antigen-binding site (i.e. the assembly of 2 fusion proteins does not constitute a fragment antigen-binding (Fab fragment)).

In a particular embodiment, the present invention relates to an antigen-binding format consisting of:

- a first fusion protein wherein the CH1 constant domain of an antibody is fused i) by its N-terminal end to the C-terminal end of a variable domain of an antibody and ii) by its C-terminal end to the N-terminal end of a variable domain of an antibody and,
- a second fusion protein wherein the CL constant domain of an antibody is fused by its N-terminal end to the C-terminal end of a variable domain of an antibody.

with the exception of an antigen-binding format consisting of:

- a first fusion protein wherein the CH1 constant domain of an antibody is fused i) by its N-terminal end to the C-terminal end of a VH variable domain of an antibody and ii) by its C-terminal end to the N-terminal end of a variable domain of an antibody and,
- a second fusion protein wherein the CL constant domain of an antibody is fused by its N-terminal end to the C-terminal end of a VL variable domain of an antibody In some embodiments, the antigen binding format of the invention may be monospecific when all variable domains are directed against the same antigen. Moreover, the antigen binding format of the invention may be bispecific, when combination of variable domains makes them directed against two particular antigens (e.g. CEA and CD16). According to this embodiment, said antigen binding format is bivalent; i.e. two of the three variable domains are directed against the same antigen (e.g. CEA or CD16). Furthermore, the antigen binding format of the invention may be trispecific, when combination of variable domains makes them directed against three particular antigens (e.g. CEA, CD3 and CD16 or CEA, CD16, human albumin or CEA, CD3, human albumin).

In a particular embodiment, the antigen binding format of the invention is bispecific wherein two variable domains are specific for a cancer antigen (e.g. CEA) and the last variable domain is specific for an immune cell regulatory molecule (e.g. CD16).

In a particular embodiment, the antigen binding format of the invention is trispecific wherein a first variable domain is specific for a cancer antigen (e.g. CEA or any cancer antigen), a second variable domain is specific for a first immune cell regulatory molecule (e.g. CD16), and a third variable domain is specific for a second immune cell regulatory molecule (e.g. CD3). More particularly, the invention relates to an antigen binding format wherein a first variable domain is specific for a cancer antigen, a second variable domain is specific for a natural killer cell molecule (e.g. CD16), and a third variable domain is specific for a T cell molecule (e.g. CD3). provides the advantage to kill tumor cells more potently by providing both NK cells and T cells retargeting. Said binding antigen format also contributes to the stimulation of the adaptive immune system, because tumor killing T-lymphocytes could potentially be generated, and vaccination could be established (ie, the provision of long-term immune response and memory cells that could rapidly generate a new and efficient response in the case of metastasis development).

In a particular embodiment, the antigen binding format of the invention consists of:

- a first fusion protein consisting of a CH1 domain fused directly by its N-terminal end to a single domain antibody specific for CD16 and fused via a spacer by its C-terminal end to a single domain antibody specific for carcinoembryonic antigen (CEA) wherein said spacer is AAA or DKT; and
- a second fusion protein consisting of a CL domain of a kappa (κ) light chain fused directly by its N-terminal end with a single domain antibody specific for carcinoembryonic antigen (CEA).

In a particular embodiment, an antigen binding format of the invention is represented by format 514-515 or 1214-1215 in FIG. 1.

In a particular embodiment, the antigen binding format of the invention is trispecific wherein the first variable domain is specific for a cancer antigen (e.g. CEA), the second variable domain is specific for a immune cell regulatory molecule (e.g. CD16), and the third variable domain is specific for albumin. More particularly, the invention relates to an antigen binding format wherein a first variable domain is specific for a cancer antigen, a second variable domain is specific for a natural killer cell molecule (e.g. CD16), and a third variable domain is specific for a albumin. The half life of the antigen binding format in the systemic circulation may be thus increased without affecting its tumor cell killing effects.

Nucleic Acids, Vectors and Recombinant Host Cells of the Invention

A further object of the present invention relates to a nucleic acid molecule encoding for an antigen binding format according to the invention.

As used herein, a sequence "encoding" an expression product, such as a RNA, polypeptide, protein, or enzyme, is a nucleotide sequence that, when expressed, results in the production of that RNA, polypeptide, protein, or enzyme, i.e., the nucleotide sequence encodes an amino acid sequence for that polypeptide, protein or enzyme. A coding sequence for a protein may include a start codon (usually ATG) and a stop codon.

These nucleic acid molecules can be obtained by conventional methods well known to those skilled in the art.

Typically, said nucleic acid is a DNA or RNA molecule, which may be included in a suitable vector, such as a plasmid, cosmid, episome, artificial chromosome, phage or viral vector.

So, a further object of the present invention relates to a vector and an expression cassette in which a nucleic acid molecule encoding for an antigen binding format of the invention is associated with suitable elements for controlling transcription (in particular promoter, enhancer and, optionally, terminator) and, optionally translation, and also the recombinant vectors into which a nucleic acid molecule in accordance with the invention is inserted. These recombinant vectors may, for example, be cloning vectors, or expression vectors.

As used herein, the terms "vector", "cloning vector" and "expression vector" mean the vehicle by which a DNA or RNA sequence (e.g. a foreign gene) can be introduced into a host cell, so as to transform the host and promote expression (e.g. transcription and translation) of the introduced sequence.

According to the invention, the vector is a bicistronic vector that includes two nucleic acid molecules, each one encoding for a fusion protein of the antigen binding format.

Any expression vector for animal cell can be used. Examples of suitable vectors include pAGE107 (Miyaji H et al. 1990), pAGE103 (Mizukami T et al. 1987), pHSG274 (Brady G et al. 1984), pKCR (O'Hare K et al. 1981), pSG1 beta d2-4-(Miyaji H et al. 1990) and the like.

Other examples of plasmids include replicating plasmids comprising an origin of replication, or integrative plasmids, such as for instance pUC, pcDNA, pBR, and the like.

Other examples of viral vectors include adenoviral, retroviral, herpes virus and AAV vectors. Such recombinant viruses may be produced by techniques known in the art, such as by transfecting packaging cells or by transient transfection with helper plasmids or viruses. Typical examples of virus packaging cells include PA317 cells, PsiCRIP cells, GPenv+ cells, 293 cells, etc. Detailed protocols for producing such replication-defective recombinant viruses may be found for instance in WO 95/14785, WO 96/22378, U.S. Pat. No. 5,882,877, U.S. Pat. No. 6,013,516, U.S. Pat. No. 4,861,719, U.S. Pat. No. 5,278,056 and WO 94/19478.

Examples of promoters and enhancers used in the expression vector for animal cell include early promoter and enhancer of SV40 (Mizukami T. et al. 1987), LTR promoter and enhancer of Moloney mouse leukemia virus (Kuwana Y et al. 1987), promoter (Mason J O et al. 1985) and enhancer (Gillies S D et al. 1983) of immunoglobulin H chain and the like.

The invention also includes gene delivery systems comprising a nucleic acid molecule of the invention, which can be used in gene therapy in vivo or ex vivo. This includes for instance viral transfer vectors such as those derived from retrovirus, adenovirus, adeno associated virus, lentivirus, which are conventionally used in gene therapy. This also includes gene delivery systems comprising a nucleic acid molecule of the invention and a non-viral gene delivery vehicle. Examples of non viral gene delivery vehicles include liposomes and polymers such as polyethylenimines, cyclodextrins, histidine/lysine (HK) polymers, etc.

A subject of the present invention is also a prokaryotic or eukaryotic host cell genetically transformed with at least one nucleic acid molecule or vector according to the invention (preferably a bicistronic vector as above described).

The term "transformation" means the introduction of a "foreign" (i.e. extrinsic or extracellular) gene, DNA or RNA sequence to a host cell, so that the host cell will express the introduced gene or sequence to produce a desired substance, typically a protein or enzyme coded by the introduced gene or sequence. A host cell that receives and expresses introduced DNA or RNA has been "transformed".

In a particular embodiment, for expressing and producing antigen binding formats of the invention, prokaryotic cells, in particular *E. coli* cells, will be chosen. Actually, according to the invention, it is not mandatory to produce the antigen binding format of the invention in a eukaryotic context that will favour post-translational modifications (e.g. glycosylation). Furthermore, prokaryotic cells have the advantages to produce protein in large amounts. If a eukaryotic context is needed, yeasts (e.g. *saccharomyces* strains) may be particularly suitable since they allow production of large amounts of proteins. Otherwise, typical eukaryotic cell lines such as CHO, BHK-21, COS-7, C127, PER.C6, YB2/0 or HEK293 could be used, for their ability to process to the right post-translational modifications of the antigen binding format of the invention.

Accordingly, a further aspect of the invention relates to a host cell comprising a nucleic acid molecule encoding for an antigen binding format according to the invention or a vector according to the invention.

The construction of expression vectors in accordance with the invention, and the transformation of the host cells can be carried out using conventional molecular biology techniques. The antigen binding formats of the invention, can, for example, be obtained by culturing genetically transformed cells in accordance with the invention and recovering the antigen binding format expressed by said cell, from the culture. They may then, if necessary, be purified by conventional procedures, known in themselves to those skilled in the art, for example by fractional precipitation, in particular ammonium sulfate precipitation, electrophoresis, gel filtration, affinity chromatography, etc. . . . In particular, conventional methods for preparing and purifying recombinant proteins may be used for producing the proteins in accordance with the invention.

A further aspect of the invention relates to a method for producing an antigen binding format of the invention comprising the step consisting of: (i) culturing a transformed host cell according to the invention under conditions suitable to allow expression of said antigen binding format; and (ii) recovering the expressed antigen binding format.

Therapeutic Methods and Uses of the Invention

The present invention provides methods and compositions (such as pharmaceutical compositions) for treating cancer or infectious diseases. Antigen binding formats of the invention are indeed particularly suitable for the treatment of diseases such as cancer or infectious diseases.

Therefore, a further object of the invention relates to an antigen binding format of the invention for use as a medicament.

More particularly, an aspect of the invention relates to an antigen binding format of the invention for use in the treatment of cancer or infectious diseases.

In the context of the invention, the term "treating" or "treatment", as used herein, means reversing, alleviating, inhibiting the progress of, or preventing the disorder or condition to which such term applies, or one or more symptoms of such disorder or condition.

As used herein, the term "infectious disease" is intended to encompass any disease which results from an infection mediated by a virus, a bacteria or a parasite. Therefore the term includes but is not limited to infection with virus such as human immunodeficiency virus, Hepatitis B virus, hepatitis C virus, with parasites such as *Plasmodium Falciparum* (causative agent for Malaria), or with bacteria such as mycobacterium tuberculosis.

As used herein, the term "cancer" is intended to encompass primary and metastatic solid tumors, including carcinomas of breast, colon, rectum, lung, oropharynx, hypopharynx, esophagus, stomach, pancreas, liver, gallbladder and bile ducts, small intestine, kidney, bladder, urothelium, female genital tract, (including cervix, uterus, and ovaries as well as choriocarcinoma and gestational trophoblastic disease), male genital tract (including prostate, seminal vesicles, testes and germ cell tumors), endocrine glands (including the thyroid, adrenal, and pituitary glands), and skin, as well as hemangiomas, melanomas, sarcomas (including those arising from bone and soft tissues as well as Kaposi's sarcoma) and tumors of the brain, nerves, eyes, such as astrocytomas, gliomas, glioblastomas, retinoblastomas, neuromas, neuroblastomas, Schwannomas, and meningiomas. The term cancer also relates to tumors arising from hematopoietic malignancies such as leukemias as well both Hodgkin's and non-Hodgkin's lymphomas.

A further aspect of the invention relates to a method for treating cancer or an infectious disease, comprising administering to a subject in need thereof an amount of antigen binding format according to the invention.

As used herein, the term "subject" denotes a mammal, such as a rodent, a feline, a canine, and a primate. Preferably, a subject according to the invention is a human.

The antigen binding format of the invention may be administered in the form of a pharmaceutical composition, as defined below.

Preferably, the antigen binding formats of the invention are administered in a therapeutically effective amount.

The term "therapeutically effective amount" means a sufficient amount of the active ingredients of the invention to treat cancer or infectious disease at a reasonable benefit/risk ratio applicable to any medical treatment.

It will be understood that the total daily usage of the antigen binding formats of the invention will be decided by the attending physician within the scope of sound medical judgment. The specific therapeutically effective dose level for any particular subject will depend upon a variety of factors including the disorder being treated and the severity of the disorder; activity of the specific compound employed; the specific composition employed, the age, body weight, general health, sex and diet of the subject; the time of administration, route of administration, and rate of excretion of the specific antigen binding formats employed; the duration of the treatment; drugs used in combination or coincidental with the specific antigen binding formats employed; and like factors well known in the medical arts. For example, it is well within the skill of the art to start doses of the antigen binding formats at levels lower than those required to achieve the desired therapeutic effect and to gradually increase the dosage until the desired effect is achieved.

An approach to cancer therapy and diagnosis may also involve the use of a bispecific antigen binding format according to the invention having at least one arm that specifically binds a cancer antigen and at least one other arm that specifically binds a low molecular weight hapten. In this methodology, the antigen binding format of the invention is administered and allowed to target the cancer antigen and therefore the tumour. Some time later, a radiolabeled low molecular weight hapten is given, which being recognized by the second specificity of the antigen binding format, also localizes to the tumour.

In another particular embodiment, the antigen binding format according to the invention may act as a ligand for a cell receptor or channel. Therefore the antigen binding format according to the invention may represent an agonist, a partial agonist or an antagonist for a receptor.

Diagnostic Methods and Uses of the Invention

Antigen binding formats of the invention may also be particularly suitable for diagnosing or monitoring a disease. Said disease may be any disease and may be selected for example from the group consisting of cancers and infectious diseases.

A further aspect of the invention relates to the use of an antigen binding format of the invention for diagnosing or monitoring a disease that may be selected from the group consisting of cancers and infectious diseases.

In a particular embodiment, antigen binding formats of the invention may be labelled with a detectable molecule or substance, such as a fluorescent molecule, a radioactive molecule or any others labels known in the art. Labels are known in the art to generally provide (either directly or indirectly) a signal.

As used herein, the term "labelled", with regard to the antibody, is intended to encompass direct labelling of the antibody by coupling (i.e., physically linking) a detectable substance, such as a radioactive agent or a fluorophore (e.g. fluorescein isothiocyanate (FITC) or phycoerythrin (PE) or indocyanine (Cy5)) to the antibody, as well as indirect labelling of the antibody by reactivity with a detectable substance.

An antigen binding format of the invention may be labelled with a radioactive molecule by any method known to the art. For example radioactive molecules include but are not limited to radioactive atoms for scintigraphic studies such as I123, I124, In111, Re186, Re188. Antigen binding formats of the invention may also be labelled with a spin label for nuclear magnetic resonance (NMR) imaging (also known as magnetic resonance imaging, mri), such as iodine-123, iodine-131, indium-I11, fluorine-19, carbon-13, nitrogen-15, oxygen-17, gadolinium, manganese or iron.

A "biological sample" encompasses a variety of sample types obtained from a subject and can be used in a diagnostic or monitoring assay. Biological samples include but are not limited to blood and other liquid samples of biological origin, solid tissue samples such as a biopsy specimen or tissue cultures or cells derived therefrom, and the progeny thereof. For example, biological samples include cells obtained from a tissue sample collected from an individual suspected of having a cancer disease. Therefore, biological samples encompass clinical samples, cells in culture, cell supernatants, cell lysates, serum, plasma, biological fluid, and tissue samples.

Antigen binding formats of the invention may be useful for staging of cancer diseases (e.g., in radioimaging).

Pharmaceutical Compositions and Kits of the Invention

The invention also relates to pharmaceutical compositions comprising antigen binding formats of the invention.

Therefore, antigen binding formats of the invention may be combined with pharmaceutically acceptable excipients, and optionally sustained-release matrices, such as biodegradable polymers, to form therapeutic compositions.

"Pharmaceutically" or "pharmaceutically acceptable" refers to molecular entities and compositions that do not produce any adverse, allergic or other untoward reaction when administered to a mammal, especially a human, as appropriate. A pharmaceutically acceptable carrier or excipient refers to a non-toxic solid, semisolid or liquid filler, diluent, encapsulating material or formulation auxiliary of any type.

The form of the pharmaceutical compositions, the route of administration, the dosage and the regimen naturally depend upon the condition to be treated, the severity of the illness, the age, weight, and sex of the patient, etc.

The pharmaceutical compositions of the invention can be formulated for a topical, oral, parenteral, intranasal, intravenous, intramuscular, subcutaneous or intraocular administration and the like.

Preferably, the pharmaceutical compositions contain vehicles which are pharmaceutically acceptable for a formulation capable of being injected. These may be in particular isotonic, sterile, saline solutions (monosodium or disodium phosphate, sodium, potassium, calcium or magnesium chloride and the like or mixtures of such salts), or dry, especially freeze-dried compositions which upon addition, depending on the case, of sterilized water or physiological saline, permit the constitution of injectable solutions.

The doses used for the administration can be adapted as a function of various parameters, and in particular as a function of the mode of administration used, of the relevant pathology, or alternatively of the desired duration of treatment.

To prepare pharmaceutical compositions, an effective amount of the antigen binding format may be dissolved or dispersed in a pharmaceutically acceptable carrier or aqueous medium.

The pharmaceutical forms suitable for injectable use include sterile aqueous solutions or dispersions; formulations including sesame oil, peanut oil or aqueous propylene glycol; and sterile powders for the extemporaneous preparation of sterile injectable solutions or dispersions. In all cases, the form must be sterile and must be fluid to the extent that easy syringability exists. It must be stable under the conditions of manufacture and storage and must be preserved against the contaminating action of microorganisms, such as bacteria and fungi.

Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

An antigen binding format of the invention can be formulated into a composition in a neutral or salt form. Pharmaceutically acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

The carrier can also be a solvent or dispersion medium containing, for example, water, ethanol, polyol (for example, glycerol, propylene glycol, and liquid polyethylene glycol, and the like), suitable mixtures thereof, and vegetables oils. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminium monostearate and gelatin.

Sterile injectable solutions are prepared by incorporating the required amount of the active compounds in the appropriate solvent with various/several of the other ingredients enumerated above, as required, followed by filtered sterilization. Generally, dispersions are prepared by incorporating the various sterilized active ingredients into a sterile vehicle which contains the basic dispersion medium and the other required ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The preparation of more, or highly concentrated solutions for direct injection is also contemplated, where the use of DMSO as solvent is envisioned to result in extremely rapid penetration, delivering high concentrations of the active agents to a small tumor area.

Upon formulation, solutions will be administered in a manner compatible with the dosage formulation and in such amount as is therapeutically effective. The formulations are easily administered in a variety of dosage forms, such as the type of injectable solutions described above, but drug release capsules and the like can also be employed.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the subject being treated. The person responsible for administration will, in any event, determine the appropriate dose for the individual subject.

The antigen binding formats of the invention may be formulated within a therapeutic mixture to comprise about 0.0001 to 1.0 milligrams, or about 0.001 to 1.0 milligrams, or about 0.01 to 1.0 milligrams, or about 0.1 to 1.0 milligrams or even about 10 milligrams per dose or so. Multiple doses can also be administered.

In addition to the compounds formulated for parenteral administration, such as intravenous or intramuscular injection, other pharmaceutically acceptable forms include, e.g. tablets or other solids for oral administration; time release capsules; and any other form currently used.

In certain embodiments, the use of liposomes and/or nanoparticles is contemplated for the introduction of antigen binding formats into host cells. The formation and use of liposomes and/or nanoparticles are known to those of skill in the art.

Nanocapsules can generally entrap compounds in a stable and reproducible way. To avoid side effects due to intracellular polymeric overloading, such ultrafine particles (sized around 0.1 μm) are generally designed using polymers able to be degraded in vivo. Biodegradable polyalkyl-cyanoacrylate nanoparticles that meet these requirements are contemplated for use in the present invention, and such particles may be easily made.

Liposomes are formed from phospholipids that once dispersed in an aqueous medium spontaneously form multilamellar concentric bilayer vesicles (also termed multilamellar vesicles (MLVs)). MLVs generally have diameters ranging from 25 nm to 4 μm. Sonication of MLVs results in the formation of small unilamellar vesicles (SUVs) with diameters in the range of 200 to 500 Å, containing an aqueous solution in the core. The physical characteristics of liposomes depend on pH, ionic strength and the presence of divalent cations.

The invention also provides kits comprising at least one antigen binding format of the invention. Kits containing antigen binding formats of the invention find use in therapeutic methods or diagnostic assays.

The invention will be further illustrated by the following figures and examples. However, these examples and figures should not be interpreted in any way as limiting the scope of the present invention.

FIGURES

FIG. 1: Representation of various bispecific antibody formats.

Figure 2:
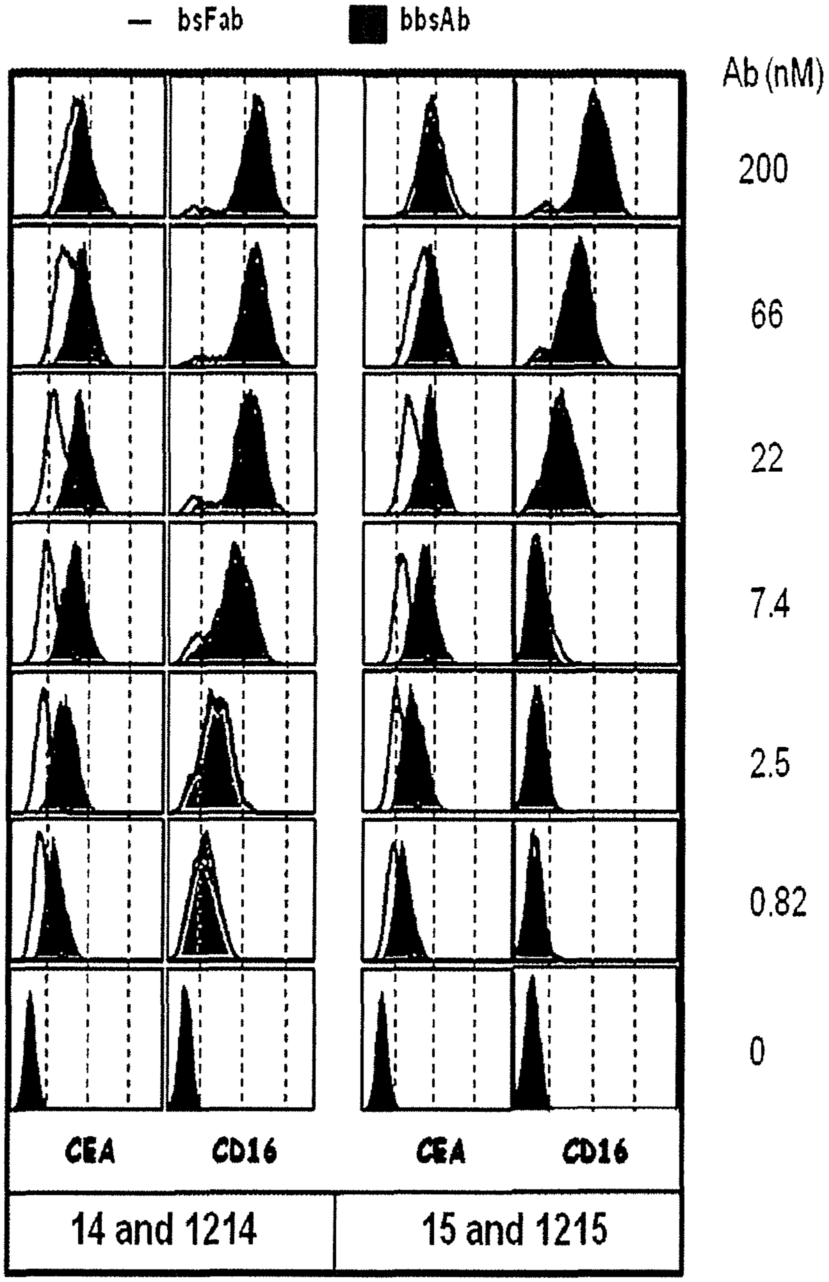

FIG. 2: Flow cytometry experiments demonstrating a higher apparent affinity of bivalent (bbsAb) vs. monovalent (bsFab) bispecific antibodies. CEA: MC38-CEA cells CD16: Jurkat-CD16 cells.

Figure 3:
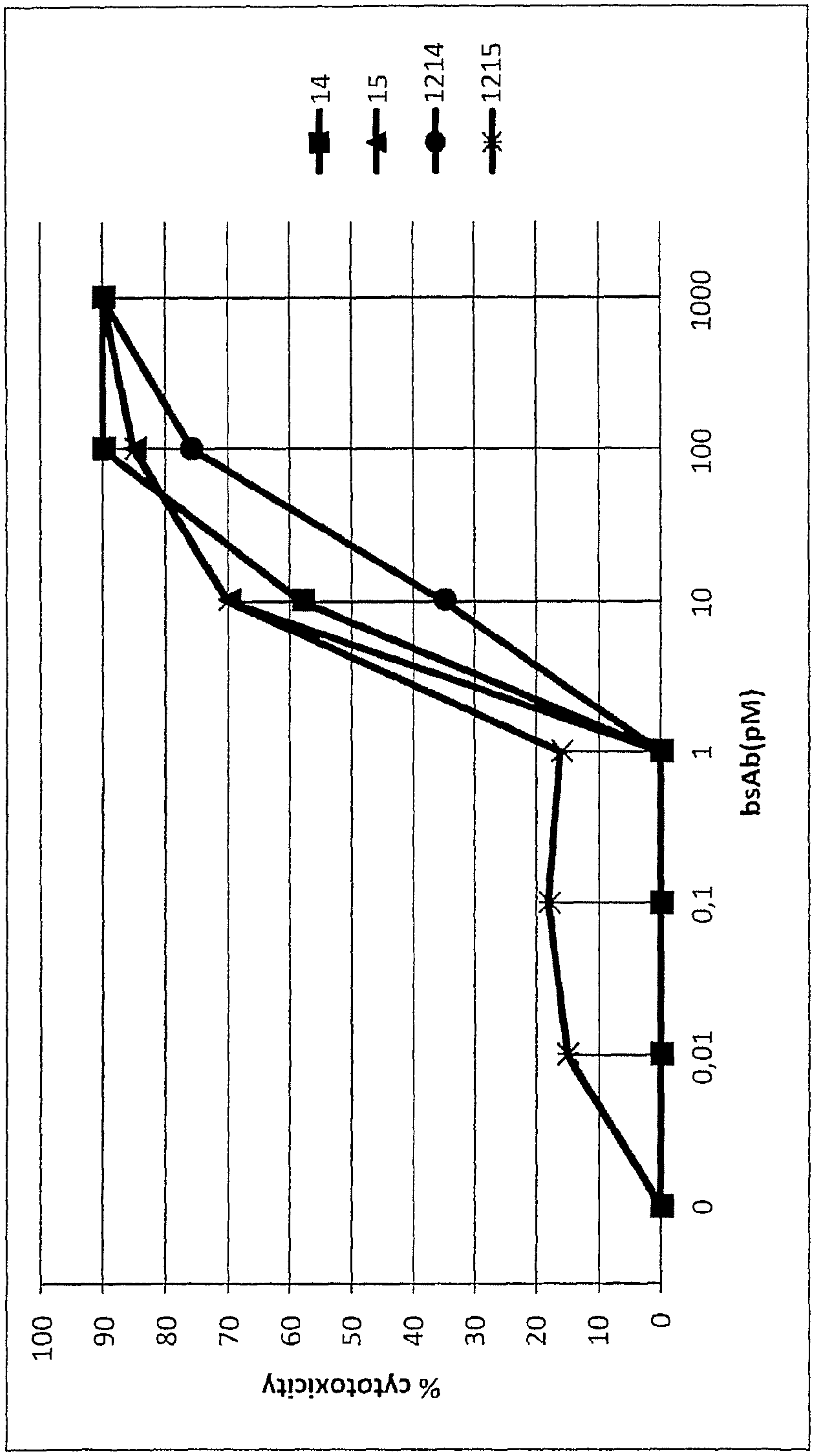

FIG. 3: In vitro cytotoxicity assays performed by flow cytometry using human NK cells and bispecific antibodies

EXAMPLE

Material & Methods

1/ Construction of the New Formats p501 (SEQ ID NO:9): Insertion of anti-CEA sdAb 17 gene (Behar, G., Chames, P., Teulon, I., Cornillon, A., Alshoukr, F., Roquet, F., Pugniere, M., Teillaud, J.-L., Gruaz-Guyon, A., Pelegrin, A. and Baty, D Llama single domain antibodies directed against non-conventional epitopes of tumor-associated carcinoembryonic antigen (CEA) absent from non-specific cross-reacting antigen (NCA). FEBS J, 2009, 276, 3881-93) of pHen1-CEA17 (SEQ ID NO:10) into p1 (SEQ ID NO:11) at the C-terminal end of CH1 domain (Not I site):

PCR: 5 ng pHen1-CEA17 (SEQ ID NO:10), 0.5 U Taq Polymerase Deep-vent (New England Biolabs), 10 μM of primer 5' Not VHH and primer 3' Not VHH rev, 5 μL Tp 10×, 1 μl $MgSO_4$ 1 mM, 4 μl dNTP 2.5 mM, $H_2O$ up to 50 μl, 94° C. 3 min, 94° C. 45 sec, 60° C. 45 sec, 72° C. 45 sec×35 cycles, 72° C. 10 min.

```
Primer 5' Not VHH Not
SEQ ID NO 1:
CCACGATTCTGCGGCCGCAGAGGTGCAGCTGGTGGAGTCTGG

Primer 3' Not VHH rev
SEQ ID NO 2:
TTTTTGTTCTGCGGCCGCTGAGGAGACGGTGACCTGGG
```

The PCR fragment was purified on 2% agarose gel using NucleoSpin Extract II kit (Macherey-Nagel) and eluted in 50 μL of buffer NE.

Digestion of p1 (SEQ ID NO:11) (5 μg) by Not I (50 U), 30 μL buffer 3 10×, 30 μL BSA 10 mg/ml, $H_2O$ up to 300 μl 1 h at 37° C. followed by dephosphorylation using 10 U of CIP (Biolabs), 30 min at 37° C. CIP was inactivated using 9 μl EDTA 0.5 M 1 h at 65° C., phenol-treated, and precipitated 16 h at −20° C. using 1 volume NaOAc 0.3M and 3 volumes ethanol 96%, followed by centrifugation 10 min at 16 000 g, washing of the pellet using 750 μl ethanol 70%. The dried pellet was resuspended in 20 μl $H_2O$.

PCR fragment (20 μl) was digested using NotI (100 U) (30 μl buffer 3 10×, 30 μl BSA 10 mg/ml, $H_2O$ up to 300 μl 1 h at 37° C.). After phenol treatment, the digested PCR fragment was precipitated 16 h at −20° C. using 1 volume NaOAc 0.3 M and 3 volumes ethanol 96%, followed by centrifugation 10 min at 16 000 g, washing of the pellet using 750 μl ethanol 70%. The dried pellet was resuspended in 20 μL $H_2O$.

Ligation: 120 ng of vector p1 (SEQ ID NO:11) and 60 ng of PCR fragment using 10 U of ligase (Biolabs), 1 μl of buffer 10×, $H_2O$ up to 10 μl, 1 h at RT, 10 min at 65° C.

Three μl of the ligation was electroporated into 40 μl of electrocompetent TG1 cell. Cells were resuspended in 1 ml SOC, 1 h at 37° C., shaked at 180 rpm, and plate on LB/ampicillin dishes.

Two 2 sets of colony-PCRs were performed on 48 colonies to check the ligation event.

```
PCR1:
Primer 5' M13 Reverse
SEQ ID NO 3:
CAGGAAACAGCTATGAC
and
```

-continued

```
Primer 3' Hind 111 + 40
SEQ ID NO 4:
GCTGAAAATCTTCTCTCATCCG

PCR2:
Primer 5' Flag
SEQ ID NO 5:
GCAGGTGATTACAAAGACGATG
and

Primer 3' Not VHH rev
(SEQ ID NO 2)
```

(0.25 U Dynazyme II (Finnzyme), 2.5 μL buffer 10×, 10 mM dNTP, $H_2O$ up to 25 μL, 94° C. 3 min, 94° C. 45 sec, 60° C. 45 sec, 72° C. 45 sec×35 cycles, 72° C. 10 min).

Four positive clones were assayed for expression: induction 12 h at 30° C., IPTG 100 μM, loading of cell lysate on SDS-PAGE 15%, and western blot using 9E10-HRP diluted 1/100).

The sequences were checked (Millegen).

p514 (SEQ ID NO:12): Insertion of the NheI/HindIII fragment from p501 (SEQ ID NO:9) into p14 (SEQ ID NO:13):

10 μg of each vector was digested in 10 μl buffer 2 10×, 10 μl of BSA (10 mg/ml) 20 U NheI, 20 U HindIII, $H_2O$ up to 100 μl, 1 h at 37° C. p14 (SEQ ID NO:13) was dephosphorylated and resuspended in TE (see above).

Fragments were gel purified as above using NucleoSpin Extract II (Macherey-Nagel) and eluted using 25 μl $H_2O$. Fragments were ligated and ligation was electroporated as above.

Colony-PCR was performed using primers 5' sigpelbfor (SEQ ID NO 6: TACCTATTGCCTACGGCAGCC) and 3' HindIII+40 (SEQ ID NO 4), 0.25 U Dynazyme II (Finnzyme), 2.5 μl buffer 10×, 4 μl dNTP 2.5 mM, $H_2O$ up to 25 μl, 94° C. 3 min, 94° C. 1 min 30 sec, 60° C. 1 min 30 sec, 72° C. 1 min 30 sec×35 cycles, 72° C. 10 min. Four positive clones were assayed for expression as above, and sequences were checked (Millegen)

p515 (SEQ ID NO:14): Insertion of the NheI/HindIII fragment from p501 (SEQ ID NO:9) into p15 (SEQ ID NO:15):

As for p514 p1201 (SEQ ID NO:16): Mutation from AAA to DKT spacer on p501 (SEQ ID NO:9):

Quikchange on p501 (SEQ ID NO:9) using 125 ng of each primer, 5 μl of buffer 10×, 4 μl dNTP, 2.5 U Pfu Ultra (Stratagene), $H_2O$ up to 50 μl, 95° C. 1 min, 95° C. 30 sec, 55° C. 1 min, 68° C. 7 min, ×18 cycles, add 40 U Dpn I

```
Primer 5' 1201 for
SEQ ID NO: 7:
GTTGAGCCCAAATCTTGTGACAAAACTGAGGTGCAGCTGGTGG

Primer 3' 1201rev
SEQ ID NO 14:
CCACCAGCTGCACCTCAGTTTTGTCACAAGATTTGGGCTCAAC
```

Transformation was performed by electroporation into DH5α using 2 μl of Quikchange product.

Clones were tested for expression as above and sequences were checked.

p1214 (SEQ ID NO:17): Insertion of Nhe I/Hind III fragment from p1201 (SEQ ID NO:16) into p14 (SEQ ID NO:13):

Digest 1 μg of p14 (SEQ ID NO:13) and 15 μg of p1201 (SEQ ID NO:16) by NheI 20 U for p14 (SEQ ID NO:8) and 60 U for p1201 (SEQ ID NO:16) and HindIII 20 U for p14 and 60 U for p1201 using buffer 2 1× final $H_2O$ up to 50 μl, 2 h at 37° C., dephosphorylate vector 14 by adding 10 U of CIP, 30 min at 37° C., add 1.5 μl EDTA 0.5M, followed by phenol extraction, ethanol precipitate and resuspend in 20 μl $H_2O$.

Gel-purify fragment from p1201 (SEQ ID NO:16) using NucleoSpin Extract II.

Ligation using various vector ratios: insert, using 10 μl Buffer 2×, 3 U T4 DNA ligase (Promega), $H_2O$ up to 50 μl, 15 min RT, 15 min at 65° C., ethanol precipitate and resuspend in 4 μl $H_2O$ Electroporate 40 μl of DH5α using 4 μl of ligation, plate on LB/Ampi 100 μg/ml petri dishes Clones were tested for expression as above and sequences were checked.

p1215 (SEQ ID NO:18): as for p1214 (SEQ ID NO:17) but using p15 (SEQ ID NO:15):

2/ Production and Purification of Abs

2.1 Production in *E. Coli*

The *E. coli* K12 strain DH5α was used for the Ab production. First, a single colony containing the plasmid of interest was inoculated in 50 ml of LB medium supplemented with ampicillin 100 μg/ml and 2% glucose. The bacteria were grown at 30° C. and shaken at 205 rpm overnight. Four hundred ml of LB medium supplemented with ampicillin 100 μg/ml was inoculated with the previous culture to obtain an $OD_{600\ nm}$ of 0.1. The bacteria were grown at 30° C. for 2 h 30, then at 20° C. to an $OD_{600\ nm}$ of 0.8-1. The production of Abs was induced by addition of 0.1 mM IPTG (Isopropyl-β-D-thiogalactopyranoside) for 60 h at 20° C.

2.2 Extraction of the Soluble Fraction of the Periplasm

Cells were harvested by centrifugation at 1860 g for 30 min at 4° C. The pellet was thoroughly resuspended in 4 ml of cold TES buffer pH 8.0 (0.2 M Tris HCl pH 8, 0.5 mM EDTA, 0.5 M Sucrose) before adding 1.6 mg of freshly made lysosyme solution. The cells were then submitted to an osmotic shock by addition of 8 ml of cold TES buffer and 8 ml of cold water. After an incubation of 30 min on ice, 250 μg of DNAse I (Roche) and 250 μl of 1 M $MgCl_2$ were added and the mixture was further incubated 30 min at room temperature. The mixture was centrifuged at 1860 g for 1 h at 4° C. After addition of one tablet of a protease inhibitor cocktail, Complete EDTA-free (Roche) into 50 ml of supernatant, the supernatant was dialyzed for 16 h at 4° C. against 50 mM sodium acetate buffer pH 7.0 containing 0.1 M NaCl.

2.3 Purification of Abs

Purification by Cobalt Affinity Chromatography

After filtration on 0.2 μm filter (Millipore), the supernatant was loaded on a 2 ml BD Talon™ Metal Affinity column (BD Biosciences Clontech) previously equilibrated in a 50 mM sodium acetate buffer pH 7.0 containing 0.1 M NaCl. The column was washed with 5 volumes of 50 mM sodium acetate buffer pH 7.0 containing 1 M NaCl then with 5 volumes of 50 mM sodium acetate buffer pH 7.0 containing 0.1 M NaCl. Elution was performed by a linear imidazol gradient (0 to 250 mM). The elution profile was followed spectrophotometrically at 280 nm. The purified fractions were analyzed by SDS PAGE 12% stained with Coomassie blue and western blotting using anti cmyc-HRP antibody (1 μg/ml, Santa Cruz Biotechnologies) and anti-flag-HRP antibody (0.5 μg/ml, Sigma).

Purification by Affinity Chromatography on Protein G

The fractions containing Abs were pooled, dialyzed against PBS buffer (137 mM NaCl, 2.7 mM KCl, 1.2 mM Na2HPO4, 1.76 mM KH2PO4 pH 7.4) and loaded onto a 1 ml Hi-Trap Protein G column (Amersham Biosciences). After washing the column with 5 volumes of PBS, the antibodies were eluted with a 0.1 M glycine HCl buffer pH 2.7 and neutralized by addition of 1/10 volume of 1 M Tris-HCl buffer pH 9.0. The elution profile was followed spectrophotometrically at 280 nm. Purification of Abs was followed by SDS PAGE 12% stained with Coomassie blue and western blotting. Fractions of interest were pooled, washed in PBS and concentrated on Vivaspin devices (cut off 5 kDa, Millipore).

Ab concentrations were determined by the colorimetric method of Lowry using the Biorad protein assay kit. Abs were diluted with one volume of glycerol and stored at −20° C.

3/ Flow Cytometry Experiments

Binding of bsAb to CEA was assessed using MC38-CEA cells. Binding of antibodies to CD16A was assessed using Jurkat-CD16A cells. Cells ($5\times10^5$ cells/well) were distributed in a V-bottom 96 well microplate and incubated with various concentrations of antibodies (0.82 to 200 nM) for 1 h at 4° C. All cell and antibody dilutions were performed in PBS 1% BSA. Bound antibodies were stained by monoclonal mouse anti c-myc antibody 9E10 (4 μg/ml, (Santa Cruz Biotechnology) for CEA binding or mouse anti-flag M2 antibody (1 μg/ml, Sigma) for CD16A binding, followed by F(ab')2 goat anti-mouse-FITC antibody (7 μg/mL, Beckman Coulter). After several washes with PBS 1% BSA, labelled cells were gently resuspended in 200 μl PBS BSA 1% and analyzed by flow cytometry on a FACS Calibur cytometer (BD Biosciences). The results were analyzed with CellQuest Pro (BD Biosciences) or Flowjo (Treestart Inc.) softwares.

4/ In Vitro Cytotoxicity Assays

4.1 Isolation of PBMCs (Peripheral Blood Mononuclear Cells)

A blood pack (400 ml) from a healthy donor was recovered in the EFS (Etablissement français du sang) Marseille, France. The blood was diluted in half in PBS 1% FCS and distributed in tubes of blood separation (PAA) previously filled with gradient separation (LSM 1077 Lymphocyte, PAA). The tubes were centrifuged 40 min at 400 g at room temperature with no acceleration and no brake. The opaque ring at the interface between plasma and gradient separation containing PBMCs was recovered. The cells were then washed twice in PBS 1% FCS and centrifuged 20 min at 150 g at room temperature. The cells were then counted on Malassez cell and either resuspended in FCS 20% DMSO and frozen in nitrogen or used for further assays.

4.2 NK Cells Purification

The selection of NK (natural killer) cells was made by negative depletion using the NK cell isolation kit (Milteny Biotec) from PBMCs from healthy donors according to manufactor's indications.

One hundred million of previously isolated PBMC were resuspended in 400 μl of cold buffer (PBS 0.5% BSA 2 mM EDTA). The cells were incubated with 100 μl of a cocktail of antibodies: biotin NK cell antibody cocktail, 10 min on ice. After addition of 300 μL of cold buffer, the cells were incubated with 200 μl of magnetic beads: NK cell cocktail microbeads, 15 min on ice. The cells were then washed with 10 ml of buffer and then resuspended in 500 μl of buffer. The cell suspension was loaded onto the MACS LS column placed in a magnetic field of a MAC Separator and washed with 9 ml of buffer. The unlabelled NK cells were collected, counted and resuspended in culture medium RPMI 10% FCS.

4.3 Cytotoxicity Assay by Flow Cytometry

The cytotoxicity assay by flow cytometry quantifies the lysis of CEA positive target cells induced by CD16+ cells such as NK cells from healthy donors under the action of bsAb.

4.4 Labelling of Target Cells with CFSE

Five millions of CEA+ target cells (MC38-CEA) were washed twice in PBS 1% BSA before addition of CFSE (Carboxyfluorescein succinimidyl ester) at a final concentration of 5 μM in 1 ml of PBS 1% BSA for 10 min in water bath at 37° C. The reaction was then stopped by adding an excess of cold PBS 1% BSA. Cells were washed twice in culture medium RPMI 10% FCS.

CFSE labeled target cells (20 000 cells in 100 μL per well) were incubated with various concentrations of antibodies (1000 pM to 0.01 pM). Each point was made in triplicate. NK cells freshly isolated from PBMC were then added at a effector/target ratio of 10/1. The plate was centrifuged at 560 g for 30 s and incubated at 37° C. for 12 h.

Cells were recovered and washed twice in PBS 1% BSA and incubated for 5 min with 100 μL of 2 nM To-pro3. After addition of 100 μL of PBS 1% BSA, the samples were analyzed by flow cytometry (FACS Calibur, BD Biosciences). Target cell lysis was subsequently measured by release of intracellular label by a scintillation counter or spectrophotometry. Dead target cells were identified as CFSE+/To-pro 3+ cells.

$$\%\ \text{lysis}=(\%\ \text{Target}+NK+Ab-\%\ \text{Target}+NK)/(100-\%\ \text{Target}+NK)\times 100.$$

Results

The modularity of single domain antibodies combined to the use of the human heterodimerization motif constituted by the CH1/Cκ domains allows the efficient generation of multivalent and/or multispecific recombinant antibodies. We have previously demonstrated the possibility to produce active bispecific monovalent constructs named bsAb (see FIG. 1 and WO/2006/064136) allowing the efficient retargeting and activation of effector cells such as human NK cells and macrophages toward tumor cells, leading to their lysis.

In these constructs, the sdAbs were linked to the N-terminal extremities of CH1 and Cκ domains by their C-terminal extremities. In this work, we wanted to establish the possibility to link the N-terminal end of the sdAb to the C-terminus of the CH1 domain to create multivalent bispecific molecules. Several molecules corresponding to the addition of one anti-CEA domain to the original bsAb format were thus constructed. The N-terminus of sdAbs is located at the tip of the domain, i.e. close to the antigen binding interface. To avoid possible steric clashes, the effect of the addition of small spacers (3 residues, AAA or DKT) was investigated. A representation of these various new formats is shown in FIG. 1.

All these molecules were produced in the periplasm of *E. coli* to allow a proper disulfide bond formation within each Ig domain and purified after periplasm extraction using a common two-steps procedure, i.e. metal affinity chromatography followed by protein G purification.

Two of the new molecules, i.e. 1214 (SEQ ID NO:25 and SEQ ID NO:26) and 1215 (SEQ ID NO:27 and SEQ ID NO:28) were compared with their monovalent parent molecules (14 and 15) chosen to demonstrate an avidity effect due to the addition of an extra anti-CEA domain, using flow cytometry on CEA+ target cells.

FIG. 2 clearly shows that bivalent constructs 1214 and 1215 yielded higher signals than their parent molecules, especially at low concentration. Altogether, these results demonstrate that single domain added at the C-terminus of CH1 can access and efficiently bind their antigen displayed at the cell surface.

The ability of these new molecules to retarget effector cells toward CEA+ target cells was demonstrated using a flow cytometry based in vitro cytotoxicity assay. CEA+ target cells were fluorescently labelled using CFSE and mixed to human NK cells at an effector: target ratio of 10:1 in the presence of various concentration of monovalent (14 and 15) or bivalent (1214 and 1215) bispecific molecules. As shown in FIG. 3, all molecules displayed a similar activity in this assay with $EC_{50}$ values in the pM range.

REFERENCES

Throughout this application, various references describe the state of the art to which this invention pertains. The disclosures of these references are hereby incorporated by reference into the present disclosure.

The invention claimed is:

1. A nucleic acid molecule encoding for an antigen binding format comprising:

a first fusion protein wherein a CH1 constant domain of an antibody is fused i) by its N-terminal end to a C-terminal end of a first single domain antibody and ii) by its C-terminal end to an N-terminal end of a second single domain antibody, wherein the C-terminal end of the CH1 constant domain includes DKT which is fused directly to the N-terminal end of the second single domain antibody, and a second fusion protein wherein a CL constant domain of an antibody is fused by its N-terminal end to a C-terminal end of a third single domain antibody, wherein said first, second and third single domain antibody may be the same or different, and wherein said CH1 constant domain and said CL constant domain are linked via a disulfide bond.

2. A vector comprising a nucleic acid molecule encoding for an antigen binding format comprising:

a first fusion protein wherein a CH1 constant domain of an antibody is fused i) by its N-terminal end to a C-terminal end of a first single domain antibody and ii) by its C-terminal end to an N-terminal end of a second single domain antibody, wherein the C-terminal end of the CH1 constant domain includes DKT which is fused directly to the N-terminal end of the second single domain antibody, and a second fusion protein wherein a CL constant domain of an antibody is fused by its N-terminal end to a C-terminal end of a third single domain antibody, wherein said first, second and third single domain antibody may be the same or different, and wherein said CH1 constant domain and said CL constant domain are linked via a disulfide bond.

3. A prokaryotic or eukaryotic host cell genetically transformed with at least one nucleic acid molecule encoding for an antigen binding format comprising:

a first fusion protein wherein a CH1 constant domain of an antibody is fused i) by its N-terminal end to a C-terminal end of a first single domain antibody and ii) by its C-terminal end to an N-terminal end of a second single domain antibody, wherein the C-terminal end of the CH1 constant domain includes DKT which is fused directly to the N-terminal end of the second single domain antibody, and a second fusion protein wherein a CL constant domain of an antibody is fused by its N-terminal end to a C-terminal end of a third single domain antibody, wherein said first, second and third single domain antibody may be the same or different, and wherein said CH1 constant domain and said CL constant domain are linked via a disulfide bond.

4. The prokaryotic or eukaryotic host cell of claim 3, wherein said at least one nucleic acid molecule is present in a vector.

* * * * *

SEQUENCE LISTING

```
<160> NUMBER OF SEQ ID NOS: 28

<210> SEQ ID NO 1
<211> LENGTH: 42
<212> TYPE: DNA
<213> ORGANISM: Artificial
<220> FEATURE:
<223> OTHER INFORMATION: Synthetic oligonucleotide primer 5' Not VHH
```

<400> SEQUENCE: 1
ccacgattct gcggccgcag aggtgcagct ggtggagtct gg 42

<210> SEQ ID NO 2
<211> LENGTH: 38
<212> TYPE: DNA
<213> ORGANISM: Artificial
<220> FEATURE:
<223> OTHER INFORMATION: Synthetic oligonucleotide primer 3' Not VHH rev

<400> SEQUENCE: 2
tttttgttct gcggccgctg aggagacggt gacctggg 38

<210> SEQ ID NO 3
<211> LENGTH: 17
<212> TYPE: DNA
<213> ORGANISM: Artificial
<220> FEATURE:
<223> OTHER INFORMATION: Synthetic oligonucleotide primer 5' M13 Reverse

<400> SEQUENCE: 3
caggaaacag ctatgac 17

<210> SEQ ID NO 4
<211> LENGTH: 22
<212> TYPE: DNA
<213> ORGANISM: Artificial
<220> FEATURE:
<223> OTHER INFORMATION: Synthetic oligonucleotide primer 3' Hind III+40

<400> SEQUENCE: 4
gctgaaaatc ttctctcatc cg 22

<210> SEQ ID NO 5
<211> LENGTH: 22
<212> TYPE: DNA
<213> ORGANISM: Artificial
<220> FEATURE:
<223> OTHER INFORMATION: Synthetic oligonucleotide primer 5' Flag

<400> SEQUENCE: 5
gcaggtgatt acaaagacga tg 22

<210> SEQ ID NO 6
<211> LENGTH: 21
<212> TYPE: DNA
<213> ORGANISM: Artificial
<220> FEATURE:
<223> OTHER INFORMATION: Synthetic oligonucleotide primer 5' sigpelbfor

<400> SEQUENCE: 6
tacctattgc ctacggcagc c 21

<210> SEQ ID NO 7
<211> LENGTH: 43
<212> TYPE: DNA
<213> ORGANISM: Artificial
<220> FEATURE:
<223> OTHER INFORMATION: Synthetic oligonucleotide primer 5' 1201for

<400> SEQUENCE: 7
gttgagccca aatcttgtga caaaactgag gtgcagctgg tgg 43

<210> SEQ ID NO 8

-continued

<211> LENGTH: 43
<212> TYPE: DNA
<213> ORGANISM: Artificial
<220> FEATURE:
<223> OTHER INFORMATION: Synthetic oligonucleotide primer 3' 1201rev

<400> SEQUENCE: 8
ccaccagctg cacctcagtt ttgtcacaag atttgggctc aac 43

<210> SEQ ID NO 9
<211> LENGTH: 6536
<212> TYPE: DNA
<213> ORGANISM: Artificial
<220> FEATURE:
<223> OTHER INFORMATION: Synthetic plasmid p501

<400> SEQUENCE: 9
cctgaattga ctctcttccg ggcgctatca tgccataccg cgaaaggttt tgcgccattc 60
gatggtgtca acgtaaatgc atgccgcttc gccttcgcgc gcgaattgca agctgatccg 120
gagcttatcg actgcacggt gcaccaatgc ttctggcgtc aggcagccat cggaagctgt 180
ggtatggctg tgcaggtcgt aaatcactgc ataattcgtg tcgctcaagg cgcactcccg 240
ttctggataa tgtttttttgc gccgacatca taacggttct ggcaaatatt ctgaaatgag 300
ctgttgacaa ttaatcatcg gctcgtataa tgtgtggaat tgtgagcgga taacaatttc 360
acacaggaaa cagaattcca tatgaaatac ctattaccaa cagcagcagc tgggttatta 420
ttgctcgctg cgcagccggc catggcccag gtcaccgtct cctcacgtac ggtggctgca 480
ccatctgtct tcatcttccc gccatctgat gagcagttga aatctggaac tgcctctgtt 540
gtgtgcctgc tgaataactt ctatcccaga gaggccaaag tacagtggaa ggtggataac 600
gccctccaat cgggtaactc ccaggagagt gtcacagagc aggacagcaa ggacagcacc 660
tacagcctca gcagcaccct gacgctgagc aaagcagact acgagaaaca caaagtctac 720
gcctgcgaag tcacccatca gggcctgagc tcgccggtga caaagagctt caaccgcgga 780
gagtgtgcag gtgattacaa agacgatgac gataagtaat aaacaggaaa cagaagtcca 840
tatgaaatac ctattgccta cggcagccgc tggattgtta ttactcgcgg cccagccggc 900
catggccgct agcaccaagg gcccatcggt cttccccctg gcaccctcct ccaagagcac 960
ctctgggggc acagcggccc tgggctgcct ggtcaaggac tacttccccg aaccggtgac 1020
ggtgtcgtgg aactcaggcg ccctgaccag cggcgtgcac accttcccgg ctgtcctaca 1080
gtcctcagga ctctactccc tcagcagcgt agtgaccgtg ccctccagca gcttgggcac 1140
ccagacctac atctgcaacg tgaatcacaa gcccagcaac accaaggtgg acaagaaagt 1200
tgagcccaaa tcttgtgcgg ccgcagaggt gcagctggtg gagtctgggg gaggcttcgt 1260
gcaggcgggg gaatctctga cgctctcctg tacaagttct acactgacct tcactccgta 1320
tcgcatggcc tggtaccgcc aggctccagg gaagcagcgt gatttagtcg cggatattag 1380
tagtggtgat ggtaggacca caaactatgc ggacttcgcg aagggccgat tcaccatctc 1440
cagagacaac atcaagaaca cggtctttct gcgaatgact aacctgaaac ctgaggacac 1500
ggccgtctac tactgtaaca ccttcgtttc gtttgtgggg attgcgcgtt cttggggcca 1560
ggggacccag gtcactgtct cctcagcggc cgcagaacaa aaactcatct cagaagagga 1620
tctgaatggg gccgtacatc accaccatca tcatgggagc taagcttctg ttttggcgga 1680
tgagagaaga ttttcagcct gatacagatt aaatcagaac gcagaagcgg tctgataaaa 1740
cagaatttgc ctggcggcag tagcgcggtg gtcccacctg accccatgcc gaactcagaa 1800

-continued gtgaaacgcc gtagcgccga tggtagtgtg gggtctcccc atgcgagagt agggaactgc 1860
caggcatcaa ataaaacgaa aggctcagtc gaaagactgg gcctttcgtt ttatctgttg 1920
tttgtcggtg aacgctctcc tgagtaggac aaatccgccg ggagcggatt tgaacgttgc 1980
gaagcaacgg cccggaggac cctggcgggc aggacgcccg ccataaactg ccaggcatca 2040
aattaagcag aaggccatcc tgacggatgg cctttttgcg tttctacaaa ctcttttgtt 2100
tatttttcta aatacattca aatatgtatc cgctcatgag acaataaccc tgataaatgc 2160
ttcaataata ttgaaaaagg aagagtatga gtattcaaca tttccgtgtc gcccttattc 2220
ccttttttgc ggcattttgc cttcctgttt ttgctcaccc agaaacgctg gtgaaagtaa 2280
aagatgctga agatcagttg ggtgcacgag tgggttacat cgaactggat ctcaacagcg 2340
gtaagatcct tgagagtttt cgccccgaag aacgttttcc aatgatgagc acttttaaag 2400
ttctgctatg tggcgcggta ttatcccgtg ttgacgccgg gcaagagcaa ctcggtcgcc 2460
gcatacacta ttctcagaat gacttggttg agtactcacc agtcacagaa aagcatctta 2520
cggatggcat gacagtaaga gaattatgca gtgctgccat aaccatgagt gataacactg 2580
cggccaactt acttctgaca acgatcggag gaccgaagga gctaaccgct tttttgcaca 2640
acatggggga tcatgtaact cgccttgatc gttgggaacc ggagctgaat gaagccatac 2700
caaacgacga gcgtgacacc acgatgcctg tagcaatggc aacaacgttg cgcaaactat 2760
taactggcga actacttact ctagcttccc ggcaacaatt aatagactgg atggaggcgg 2820
ataaagttgc aggaccactt ctgcgctcgg cccttccggc tggctggttt attgctgata 2880
aatctggagc cggtgagcgt gggtctcgcg gtatcattgc agcactgggg ccagatggta 2940
agccctcccg tatcgtagtt atctacacga cggggagtca ggcaactatg gatgaacgaa 3000
atagacagat cgctgagata ggtgcctcac tgattaagca ttggtaactg tcagaccaag 3060
tttactcata tatactttag attgatttaa aacttcattt ttaatttaaa aggatctagg 3120
tgaagatcct ttttgataat ctcatgacca aaatccctta acgtgagttt tcgttccact 3180
gagcgtcaga ccccgtagaa aagatcaaag gatcttcttg agatcctttt tttctgcgcg 3240
taatctgctg cttgcaaaca aaaaaaccac cgctaccagc ggtggtttgt ttgccggatc 3300
aagagctacc aactcttttt ccgaaggtaa ctggcttcag cagagcgcag ataccaaata 3360
ctgtccttct agtgtagccg tagttaggcc accacttcaa gaactctgta gcaccgccta 3420
catacctcgc tctgctaatc ctgttaccag tggctgctgc cagtggcgat aagtcgtgtc 3480
ttaccgggtt ggactcaaga cgatagttac cggataaggc gcagcggtcg ggctgaacgg 3540
ggggttcgtg cacacagccc agcttggagc gaacgaccta caccgaactg agatacctac 3600
agcgtgagca ttgagaaagc gccacgcttc ccgaagggag aaaggcggac aggtatccgg 3660
taagcggcag ggtcggaaca ggagagcgca cgagggagct tccaggggga aacgcctggt 3720
atctttatag tcctgtcggg tttcgccacc tctgacttga gcgtcgattt ttgtgatgct 3780
cgtcaggggg gcggagccta tggaaaaacg ccagcaacgc ggccttttta cggttcctgg 3840
ccttttgctg gccttttgct cacatgttct ttcctgcgtt atcccctgat tctgtggata 3900
accgtattac cgcctttgag tgagctgata ccgctcgccg cagccgaacg accgagcgca 3960
gcgagtcagt gagcgaggaa gcggaagagc gcctgatgcg gtattttctc cttacgcatc 4020
tgtgcggtat ttcacaccgc atatatggtg cactctcagt acaatctgct ctgatgccgc 4080
atagttaagc cagtatacac tccgctatcg ctacgtgact gggtcatggc tgcgccccga 4140

-continued

```
cacccgccaa cacccgctga cgcgccctga cgggcttgtc tgctcccggc atccgcttac   4200
agacaagctg tgaccgtctc cgggagctgc atgtgtcaga ggttttcacc gtcatcaccg   4260
aaacgcgcga ggcagctgcg gtaaagctca tcagcgtggt cgtgaagcga ttcacagatg   4320
tctgcctgtt catccgcgtc cagctcgttg agtttctcca gaagcgttaa tgtctggctt   4380
ctgataaagc gggccatgtt aagggcggtt ttttcctgtt tggtcacttg atgcctccgt   4440
gtaaggggga atttctgttc atgggggtaa tgataccgat gaaacgagag aggatgctca   4500
cgatacgggt tactgatgat gaacatgccc ggttactgga acgttgtgag ggtaaacaac   4560
tggcggtatg gatgcggcgg gaccagagaa aaatcactca gggtcaatgc cagcgcttcg   4620
ttaatacaga tgtaggtgtt ccacagggta gccagcagca tcctgcgatg cagatccgga   4680
acataatggt gcagggcgct gacttccgcg tttccagact ttacgaaaca cggaaaccga   4740
agaccattca tgttgttgct caggtcgcag acgttttgca gcagcagtcg cttcacgttc   4800
gctcgcgtat cggtgattca ttctgctaac cagtaaggca accccgccag cctagccggg   4860
tcctcaacga caggagcacg atcatgcgca cccgtggcca ggacccaacg ctgcccgaga   4920
tgcgccgcgt gcggctgctg gagatggcgg acgcgatgga tatgttctgc caagggttgg   4980
tttgcgcatt cacagttctc cgcaagaatt gattggctcc aattcttgga gtggtgaatc   5040
cgttagcgag gtgccgccgg cttccattca ggtcgaggtg gcccggctcc atgcaccgcg   5100
acgcaacgcg gggaggcaga caaggtatag ggcggcgcct acaatccatg ccaacccgtt   5160
ccatgtgctc gccgaggcgg cataaatcgc cgtgacgatc agcggtccag tgatcgaagt   5220
taggctggta agagccgcga gcgatccttg aagctgtccc tgatggtcgt catctacctg   5280
cctggacagc atggcctgca acgcgggcat cccgatgccg ccggaagcga gaagaatcat   5340
aatggggaag gccatccagc ctcgcgtcgc gaacgccagc aagacgtagc ccagcgcgtc   5400
ggccagcttg caattcgcgc taacttacat taattgcgtt gcgctcactg cccgctttcc   5460
agtcgggaaa cctgtcgtgc cagctgcatt aatgaatcgg ccaacgcgcg gggagaggcg   5520
gtttgcgtat tgggcgccag ggtggttttt cttttcacca gtgagacggg caacagctga   5580
ttgcccttca ccgcctggcc ctgagagagt tgcagcaagc ggtccacgct ggtttgcccc   5640
agcaggcgaa aatcctgttt gatggtggtt gacggcggga tataacatga gctgtcttcg   5700
gtatcgtcgt atcccactac cgagatatcc gcaccaacgc gcagcccgga ctcggtaatg   5760
gcgcgcattg cgcccagcgc catctgatcg ttggcaacca gcatcgcagt gggaacgatg   5820
ccctcattca gcatttgcat ggtttgttga aaaccggaca tggcactcca gtcgccttcc   5880
cgttccgcta tcggctgaat ttgattgcga gtgagatatt tatgccagcc agccagacgc   5940
agacgcgccg agacagaact taatggtccc gctaacagcg cgatttgctg atgacccaat   6000
gcgaccagat gctccacgcc cagtcgcgta ccgtcttcat gggagaaaat aatactgttg   6060
atgggtgtct ggtcagagac atcaagaaat aacgccggaa cattagtgca ggcagcttcc   6120
acagcaatgg catcctggtc atccagcgga tagttaatga tcagcccact gacgcgttgc   6180
gcgagaagat tgtgcaccgc cgctttacag gcttcgacgc cgcttcgttc taccatcgac   6240
accaccacgc tggcacccag ttgatcggcg cgagatttaa tcgccgcgac aatttgcgac   6300
ggcgcgtgca gggccagact ggaggtggca acgccaatca gcaacgactg tttgcccgcc   6360
agttgttgtg ccacgcggtt gggaatgtaa ttcagctccg ccatcgccgc ttccactttt   6420
tcccgcgttt tcgcagaaac gtggctggcc tggttcacca cgcgggaaac ggtctgataa   6480
gagacaccgg catactctgc gacatcgtat aacgttactg gtttcacatt caccac       6536
```

<210> SEQ ID NO 10
<211> LENGTH: 4848
<212> TYPE: DNA
<213> ORGANISM: Artificial
<220> FEATURE:
<223> OTHER INFORMATION: Synthetic plasmid pHen1-CEA17

<400> SEQUENCE: 10

```
agcgcccaat acgcaaaccg cctctccccg cgcgttggcc gattcattaa tgcagctggc     60
acgacaggtt tcccgactgg aaagcgggca gtgagcgcaa cgcaattaat gtgagttagc    120
tcactcatta ggcaccccag gctttacact ttatgcttcc ggctcgtatg ttgtgtggaa    180
ttgtgagcgg ataacaattt cacacaggaa acagctatga ccatgattac gccaagcttg    240
catgcaaatt ctatttcaag gagacagtca taatgaaata cctattgcct acggcagccg    300
ctggattgtt attactcgcg gcccagccgg ccatggccga ggtgcagctg gtggagtctg    360
ggggaggctt cgtgcaggcg ggggaatctc tgacgctctc ctgtacaagt tctacactga    420
ccttcactcc gtatcgcatg gcctggtacc gccaggctcc agggaagcag cgtgatttag    480
tcgcggatat tagtagtggt gatggtagga ccacaaacta tgcggacttc gcgaagggcc    540
gattcaccat ctccagagac aacatcaaga acacggtctt tctgcgaatg actaacctga    600
aacctgagga cacggccgtc tactactgta acaccttcgt ttcgtttgtg ggattgcgc     660
gttcttgggg ccaggggacc caggtcactg tctcctcagc ggccgcagaa caaaaactca    720
tctcagaaga ggatctgaat ggggccgcat agactgttga aagttgttta gcaaaacctc    780
atacagaaaa ttcatttact aacgtctgga aagacgacaa aactttagat cgttacgcta    840
actatgaggg ctgtctgtgg aatgctacag gcgttgtggt ttgtactggt gacgaaactc    900
agtgttacgg tacatgggtt cctattgggc ttgctatccc tgaaaatgag ggtggtggct    960
ctgagggtgg cggttctgag ggtggcggtt ctgagggtgg cggtactaaa cctcctgagt   1020
acggtgatac acctattccg ggctatactt atatcaaccc tctcgacggc acttatccgc   1080
ctggtactga gcaaaacccc gctaatccta atccttctct tgaggagtct cagcctctta   1140
atactttcat gtttcagaat aataggttcc gaaataggca gggtgcatta actgtttata   1200
cgggcactgt tactcaaggc actgaccccg ttaaaactta ttaccagtac actcctgtat   1260
catcaaaagc catgtatgac gcttactgga acggtaaatt cagagactgc gctttccatt   1320
ctggctttaa tgaggatcca ttcgtttgtg aatatcaagg ccaatcgtct gacctgcctc   1380
aacctcctgt caatgctggc ggcggctctg gtggtggttc tggtggcggc tctgagggtg   1440
gcggctctga gggtggcggt tctgagggtg gcggctctga gggtggcggt tccggtggcg   1500
gctccggttc cggtgatttt gattatgaaa aaatggcaaa cgctaataag gggggctatga  1560
ccgaaaatgc cgatgaaaac gcgctacagt ctgacgctaa aggcaaactt gattctgtcg   1620
ctactgatta cggtgctgct atcgatggtt tcattggtga cgtttccggc cttgctaatg   1680
gtaatggtgc tactggtgat tttgctggct ctaattccca aatggctcaa gtcggtgacg   1740
gtgataattc acctttaatg aataatttcc gtcaatattt accttctttg cctcagtcgg   1800
ttgaatgtcg cccttatgtc tttggcgctg gtaaaccata tgaattttct attgattgtg   1860
acaaaataaa cttattccgt ggtgtctttg cgtttctttt atatgttgcc acctttatgt   1920
atgtattttc gacgtttgct aacatactgc gtaataagga gtcttaataa gaattcactg   1980
gccgtcgttt tacaacgtcg tgactgggaa aaccctggcg ttacccaact taatcgcctt   2040
```

-continued

```
gcagcacatc cccctttcgc cagctggcgt aatagcgaag aggcccgcac cgatcgccct   2100
tcccaacagt tgcgcagcct gaatggcgaa tggcgcctga tgcggtattt tctccttacg   2160
catctgtgcg gtatttcaca ccgcatacgt caaagcaacc atagtacgcg ccctgtagcg   2220
gcgcattaag cgcggcgggt gtggtggtta cgcgcagcgt gaccgctaca cttgccagcg   2280
ccctagcgcc cgctcctttc gctttcttcc cttcctttct cgccacgttc gccggctttc   2340
cccgtcaagc tctaaatcgg gggctccctt tagggttccg atttagtgct ttacggcacc   2400
tcgaccccaa aaaacttgat ttgggtgatg gttcacgtag tgggccatcg ccctgataga   2460
cggtttttcg ccctttgacg ttggagtcca cgttctttaa tagtggactc ttgttccaaa   2520
ctggaacaac actcaaccct atctcgggct attcttttga tttataaggg attttgccga   2580
tttcggccta ttggttaaaa aatgagctga tttaacaaaa atttaacgcg aattttaaca   2640
aaatattaac gtttacaatt ttatggtgca ctctcagtac aatctgctct gatgccgcat   2700
agttaagcca gccccgacac ccgccaacac ccgctgacgc gccctgacgg gcttgtctgc   2760
tcccggcatc cgcttacaga caagctgtga ccgtctccgg gagctgcatg tgtcagaggt   2820
tttcaccgtc atcaccgaaa cgcgcgagac gaaagggcct cgtgatacgc ctatttttat   2880
aggttaatgt catgataata atggtttctt agacgtcagg tggcactttt cggggaaatg   2940
tgcgcggaac ccctatttgt ttatttttct aaatacattc aaatatgtat ccgctcatga   3000
gacaataacc ctgataaatg cttcaataat attgaaaaag gaagagtatg agtattcaac   3060
atttccgtgt cgcccttatt cccttttttg cggcattttg ccttcctgtt tttgctcacc   3120
cagaaacgct ggtgaaagta aaagatgctg aagatcagtt gggtgcacga gtgggttaca   3180
tcgaactgga tctcaacagc ggtaagatcc ttgagagttt tcgccccgaa gaacgttttc   3240
caatgatgag cacttttaaa gttctgctat gtggcgcggt attatcccgt attgacgccg   3300
ggcaagagca actcggtcgc cgcatacact attctcagaa tgacttggtt gagtactcac   3360
cagtcacaga aaagcatctt acggatggca tgacagtaag agaattatgc agtgctgcca   3420
taaccatgag tgataacact gcggccaact tacttctgac aacgatcgga ggaccgaagg   3480
agctaaccgc ttttttgcac aacatggggg atcatgtaac tcgccttgat cgttgggaac   3540
cggagctgaa tgaagccata ccaaacgacg agcgtgacac cacgatgcct gtagcaatgg   3600
caacaacgtt gcgcaaacta ttaactggcg aactacttac tctagcttcc cggcaacaat   3660
taatagactg gatggaggcg gataaagttg caggaccact tctgcgctcg gcccttccgg   3720
ctggctggtt tattgctgat aaatctggag ccggtgagcg tgggtctcgc ggtatcattg   3780
cagcactggg gccagatggt aagccctccc gtatcgtagt tatctacacg acggggagtc   3840
aggcaactat ggatgaacga aatagacaga tcgctgagat aggtgcctca ctgattaagc   3900
attggtaact gtcagaccaa gtttactcat atatacttta gattgattta aaacttcatt   3960
tttaatttaa aaggatctag gtgaagatcc tttttgataa tctcatgacc aaaatccctt   4020
aacgtgagtt ttcgttccac tgagcgtcag accccgtaga aaagatcaaa ggatcttctt   4080
gagatccttt ttttctgcgc gtaatctgct gcttgcaaac aaaaaaacca ccgctaccag   4140
cggtggtttg tttgccggat caagagctac caactctttt tccgaaggta actggcttca   4200
gcagagcgca gataccaaat actgtccttc tagtgtagcc gtagttaggc caccacttca   4260
agaactctgt agcaccgcct acatacctcg ctctgctaat cctgttacca gtggctgctg   4320
ccagtggcga taagtcgtgt cttaccgggt tggactcaag acgatagtta ccggataagg   4380
cgcagcggtc gggctgaacg gggggttcgt gcacacagcc cagcttggag cgaacgacct   4440
```

-continued

```
acaccgaact gagataccta cagcgtgagc tatgagaaag cgccacgctt cccgaaggga   4500

gaaaggcgga caggtatccg gtaagcggca gggtcggaac aggagagcgc acgagggagc   4560

ttccaggggg aaacgcctgg tatctttata gtcctgtcgg gtttcgccac ctctgacttg   4620

agcgtcgatt tttgtgatgc tcgtcagggg ggcggagcct atggaaaaac gccagcaacg   4680

cggccttttt acggttcctg gccttttgct ggccttttgc tcacatgttc tttcctgcgt   4740

tatcccctga ttctgtggat aaccgtatta ccgcctttga gtgagctgat accgctcgcc   4800

gcagccgaac gaccgagcgc agcgagtcag tgagcgagga agcggaag                4848
```

```
<210> SEQ ID NO 11
<211> LENGTH: 6167
<212> TYPE: DNA
<213> ORGANISM: Artificial
<220> FEATURE:
<223> OTHER INFORMATION: Synthetic plasmid p1

<400> SEQUENCE: 11

ttgtttattt ttctaaatac attcaaatat gtatccgctc atgagacaat aaccctgata     60

aatgcttcaa taatattgaa aaaggaagag tatgagtatt caacatttcc gtgtcgccct    120

tattcccttt tttgcggcat tttgccttcc tgtttttgct cacccagaaa cgctggtgaa    180

agtaaaagat gctgaagatc agttgggtgc acgagtgggt tacatcgaac tggatctcaa    240

cagcggtaag atccttgaga gttttcgccc cgaagaacgt tttccaatga tgagcacttt    300

taaagttctg ctatgtggcg cggtattatc ccgtgttgac gccgggcaag agcaactcgg    360

tcgccgcata cactattctc agaatgactt ggttgagtac tcaccagtca cagaaaagca    420

tcttacggat ggcatgacag taagagaatt atgcagtgct gccataacca tgagtgataa    480

cactgcggcc aacttacttc tgacaacgat cggaggaccg aaggagctaa ccgctttttt    540

gcacaacatg ggggatcatg taactcgcct tgatcgttgg gaaccggagc tgaatgaagc    600

cataccaaac gacgagcgtg acaccacgat gcctgtagca atggcaacaa cgttgcgcaa    660

actattaact ggcgaactac ttactctagc ttcccggcaa caattaatag actggatgga    720

ggcggataaa gttgcaggac cacttctgcg ctcggccctt ccggctggct ggtttattgc    780

tgataaatct ggagccggtg agcgtgggtc tcgcggtatc attgcagcac tggggccaga    840

tggtaagccc tcccgtatcg tagttatcta cacgacgggg agtcaggcaa ctatggatga    900

acgaaataga cagatcgctg agataggtgc ctcactgatt aagcattggt aactgtcaga    960

ccaagtttac tcatatatac tttagattga tttaaaactt catttttaat ttaaaaggat   1020

ctaggtgaag atcctttttg ataatctcat gaccaaaatc ccttaacgtg agttttcgtt   1080

ccactgagcg tcagaccccg tagaaaagat caaaggatct tcttgagatc cttttttct   1140

gcgcgtaatc tgctgcttgc aaacaaaaaa accaccgcta ccagcggtgg tttgtttgcc   1200

ggatcaagag ctaccaactc tttttccgaa ggtaactggc ttcagcagag cgcagatacc   1260

aaatactgtc cttctagtgt agccgtagtt aggccaccac ttcaagaact ctgtagcacc   1320

gcctacatac ctcgctctgc taatcctgtt accagtggct gctgccagtg gcgataagtc   1380

gtgtcttacc gggttggact caagacgata gttaccggat aaggcgcagc ggtcgggctg   1440

aacggggggt tcgtgcacac agcccagctt ggagcgaacg acctacaccg aactgagata   1500

cctacagcgt gagcattgag aaagcgccac gcttcccgaa gggagaaagg cggacaggta   1560

tccggtaagc ggcagggtcg gaacaggaga gcgcacgagg gagcttccag ggggaaacgc   1620
```

-continued

```
ctggtatctt tatagtcctg tcgggtttcg ccacctctga cttgagcgtc gatttttgtg   1680

atgctcgtca ggggggcgga gcctatggaa aaacgccagc aacgcggcct ttttacggtt   1740

cctggccttt tgctggcctt ttgctcacat gttctttcct gcgttatccc ctgattctgt   1800

ggataaccgt attaccgcct ttgagtgagc tgataccgct cgccgcagcc gaacgaccga   1860

gcgcagcgag tcagtgagcg aggaagcgga agagcgcctg atgcggtatt ttctccttac   1920

gcatctgtgc ggtatttcac accgcatata tggtgcactc tcagtacaat ctgctctgat   1980

gccgcatagt taagccagta tacactccgc tatcgctacg tgactgggtc atggctgcgc   2040

cccgacaccc gccaacaccc gctgacgcgc cctgacgggc ttgtctgctc ccggcatccg   2100

cttacagaca agctgtgacc gtctccggga gctgcatgtg tcagaggttt tcaccgtcat   2160

caccgaaacg cgcgaggcag ctgcggtaaa gctcatcagc gtggtcgtga agcgattcac   2220

agatgtctgc ctgttcatcc gcgtccagct cgttgagttt ctccagaagc gttaatgtct   2280

ggcttctgat aaagcgggcc atgttaaggg cggttttttc ctgtttggtc acttgatgcc   2340

tccgtgtaag ggggaatttc tgttcatggg ggtaatgata ccgatgaaac gagagaggat   2400

gctcacgata cgggttactg atgatgaaca tgcccggtta ctggaacgtt gtgagggtaa   2460

acaactggcg gtatggatgc ggcgggacca gagaaaaatc actcagggtc aatgccagcg   2520

cttcgttaat acagatgtag gtgttccaca gggtagccag cagcatcctg cgatgcagat   2580

ccggaacata atggtgcagg gcgctgactt ccgcgtttcc agactttacg aaacacggaa   2640

accgaagacc attcatgttg ttgctcaggt cgcagacgtt ttgcagcagc agtcgcttca   2700

cgttcgctcg cgtatcggtg attcattctg ctaaccagta aggcaacccc gccagcctag   2760

ccgggtcctc aacgacagga gcacgatcat gcgcacccgt ggccaggacc caacgctgcc   2820

cgagatgcgc cgcgtgcggc tgctggagat ggcggacgcg atggatatgt tctgccaagg   2880

gttggtttgc gcattcacag ttctccgcaa gaattgattg gctccaattc ttggagtggt   2940

gaatccgtta gcgaggtgcc gccggcttcc attcaggtcg aggtggcccg gctccatgca   3000

ccgcgacgca acgcggggag gcagacaagg tatagggcgg cgcctacaat ccatgccaac   3060

ccgttccatg tgctcgccga ggcggcataa atcgccgtga cgatcagcgg tccagtgatc   3120

gaagttaggc tggtaagagc cgcgagcgat ccttgaagct gtccctgatg gtcgtcatct   3180

acctgcctgg acagcatggc ctgcaacgcg ggcatcccga tgccgccgga agcgagaaga   3240

atcataatgg ggaaggccat ccagcctcgc gtcgcgaacg ccagcaagac gtagcccagc   3300

gcgtcggcca gcttgcaatt cgcgctaact tacattaatt gcgttgcgct cactgcccgc   3360

tttccagtcg ggaaacctgt cgtgccagct gcattaatga atcggccaac gcgcggggag   3420

aggcggtttg cgtattgggc gccagggtgg tttttctttt caccagtgag acgggcaaca   3480

gctgattgcc cttcaccgcc tggccctgag agagttgcag caagcggtcc acgctggttt   3540

gccccagcag gcgaaaatcc tgtttgatgg tggttgacgg cgggatataa catgagctgt   3600

cttcggtatc gtcgtatccc actaccgaga tatccgcacc aacgcgcagc ccggactcgg   3660

taatggcgcg cattgcgccc agcgccatct gatcgttggc aaccagcatc gcagtgggaa   3720

cgatgccctc attcagcatt tgcatggttt gttgaaaacc ggacatggca ctccagtcgc   3780

cttcccgttc cgctatcggc tgaatttgat tgcgagtgag atatttatgc cagccagcca   3840

gacgcagacg cgccgagaca gaacttaatg gtcccgctaa cagcgcgatt tgctgatgac   3900

ccaatgcgac cagatgctcc acgcccagtc gcgtaccgtc ttcatgggag aaaataatac   3960

tgttgatggg tgtctggtca gagacatcaa gaaataacgc cggaacatta gtgcaggcag   4020
```

-continued

```
cttccacagc aatggcatcc tggtcatcca gcggatagtt aatgatcagc ccactgacgc   4080
gttgcgcgag aagattgtgc accgccgctt tacaggcttc gacgccgctt cgttctacca   4140
tcgacaccac cacgctggca cccagttgat cggcgcgaga tttaatcgcc gcgacaattt   4200
gcgacggcgc gtgcagggcc agactggagg tggcaacgcc aatcagcaac gactgtttgc   4260
ccgccagttg ttgtgccacg cggttgggaa tgtaattcag ctccgccatc gccgcttcca   4320
ctttttcccg cgttttcgca gaaacgtggc tggcctggtt caccacgcgg gaaacggtct   4380
gataagagac accggcatac tctgcgacat cgtataacgt tactggtttc acattcacca   4440
ccctgaattg actctcttcc gggcgctatc atgccatacc gcgaaaggtt ttgcgccatt   4500
cgatggtgtc aacgtaaatg catgccgctt cgccttcgcg cgcgaattgc aagctgatcc   4560
ggagcttatc gactgcacgg tgcaccaatg cttctggcgt caggcagcca tcggaagctg   4620
tggtatggct gtgcaggtcg taaatcactg cataattcgt gtcgctcaag gcgcactccc   4680
gttctggata atgttttttg cgccgacatc ataacggttc tggcaaatat tctgaaatga   4740
gctgttgaca attaatcatc ggctcgtata atgtgtggaa ttgtgagcgg ataacaattt   4800
cacacaggaa acagaattcc atatgaaata cctattacca acagcagcag ctgggttatt   4860
attgctcgct gcgcagccgg ccatggccca ggtcaccgtc tcctcacgta cggtggctgc   4920
accatctgtc ttcatcttcc cgccatctga tgagcagttg aaatctggaa ctgcctctgt   4980
tgtgtgcctg ctgaataact tctatcccag agaggccaaa gtacagtgga aggtggataa   5040
cgccctccaa tcgggtaact cccaggagag tgtcacagag caggacagca aggacagcac   5100
ctacagcctc agcagcaccc tgacgctgag caaagcagac tacgagaaac acaaagtcta   5160
cgcctgcgaa gtcacccatc agggcctgag ctcgccggtg acaaagagct tcaaccgcgg   5220
agagtgtgca ggtgattaca aagacgatga cgataagtaa taaacaggaa acagaagtcc   5280
atatgaaata cctattgcct acggcagccg ctggattgtt attactcgcg gcccagccgg   5340
ccatggccgc tagcaccaag ggcccatcgg tcttccccct ggcaccctcc tccaagagca   5400
cctctggggg cacagcggcc ctgggctgcc tggtcaagga ctacttcccc gaaccggtga   5460
cggtgtcgtg gaactcaggc gccctgacca gcggcgtgca caccttcccg gctgtcctac   5520
agtcctcagg actctactcc ctcagcagcg tagtgaccgt gccctccagc agcttgggca   5580
cccagaccta catctgcaac gtgaatcaca agcccagcaa caccaaggtg gacaagaaag   5640
ttgagcccaa atcttgtgcg gccgcagaac aaaaactcat ctcagaagag gatctgaatg   5700
gggccgtaca tcaccaccat catcatggga gctaagcttc tgttttggcg gatgagagaa   5760
gattttcagc ctgatacaga ttaaatcaga acgcagaagc ggtctgataa aacagaattt   5820
gcctggcggc agtagcgcgg tggtcccacc tgaccccatg ccgaactcag aagtgaaacg   5880
ccgtagcgcc gatggtagtg tggggtctcc ccatgcgaga gtagggaact gccaggcatc   5940
aaataaaacg aaaggctcag tcgaaagact gggcctttcg ttttatctgt tgtttgtcgg   6000
tgaacgctct cctgagtagg acaaatccgc cgggagcgga tttgaacgtt gcgaagcaac   6060
ggcccggagg accctggcgg gcaggacgcc cgccataaac tgccaggcat caaattaagc   6120
agaaggccat cctgacggat ggcctttttg cgtttctaca aactctt                 6167
```

<210> SEQ ID NO 12
<211> LENGTH: 7246
<212> TYPE: DNA
<213> ORGANISM: Artificial
<220> FEATURE:

-continued

<223> OTHER INFORMATION: Synthetic plasmid p514

<400> SEQUENCE: 12

```
cctgaattga ctctcttccg ggcgctatca tgccataccg cgaaaggttt tgcgccattc     60
gatggtgtca acgtaaatgc atgccgcttc gccttcgcgc gcgaattgca agctgatccg    120
gagcttatcg actgcacggt gcaccaatgc ttctggcgtc aggcagccat cggaagctgt    180
ggtatggctg tgcaggtcgt aaatcactgc ataattcgtg tcgctcaagg cgcactcccg    240
ttctggataa tgtttttgc gccgacatca taacggttct ggcaaatatt ctgaaatgag     300
ctgttgacaa ttaatcatcg gctcgtataa tgtgtggaat tgtgagcgga taacaatttc    360
acacaggaaa cagaattcca tatgaaatac ctattaccaa cagcagcagc tgggttatta    420
ttgctcgctg cgcagccggc catggccgag gtgcagctgg tggagtctgg gggaggcttc    480
gtgcaggcgg gggaatctct gacgctctcc tgtacaagtt ctacactgac cttcactccg    540
tatcgcatgg cctggtaccg ccaggctcca gggaagcagc gtgatttagt cgcggatatt    600
agtagtggtg atggtaggac cacaaactat gcggacttcg cgaagggccg attcaccatc    660
tccagagaca acatcaagaa cacggtcttt ctgcgaatga ctaacctgaa acctgaggac    720
acggccgtct actactgtaa caccttcgtt tcgtttgtgg ggattgcgcg ttcttggggc    780
caggggaccc aggtcaccgt ctcctcacgt acggtggctg caccatctgt cttcatcttc    840
ccgccatctg atgagcagtt gaaatctgga actgcctctg ttgtgtgcct gctgaataac    900
ttctatccca gagaggccaa agtacagtgg aaggtggata acgccctcca atcgggtaac    960
tcccaggaga gtgtcacaga gcaggacagc aaggacagca cctacagcct cagcagcacc   1020
ctgacgctga gcaaagcaga ctacgagaaa cacaaagtct acgcctgcga agtcacccat   1080
cagggcctga gctcgcccgt gacaaagagc ttcaaccgcg gagagtgtgc aggtgattac   1140
aaagacgatg acgataagta ataaacagga aacagaagtc catatgaaat acctattgcc   1200
tacggcagcc gctggattgt tattactcgc ggcccagccg gccatggccg aggtgcagct   1260
ggtggagtct gggggagagt tggtgcaggc tgggggctct ctgagactct cctgtgcagc   1320
ctctggcctc accttcagta gctataacat gggctggttc cgccgggctc cagggaagga   1380
gcgtgagttt gtagcatcta ttacctggag tggtcgggac acattctatg cagactccgt   1440
gaagggccga ttcaccatct ccagagacaa cgccaagaac actgtttatc tgcaaatgag   1500
cagcctgaaa cctgaggaca cggccgttta ttattgtgct gcaaacccct ggccagtggc   1560
ggcgccacgt agtggcacct actggggcca agggacccag gtcaccgtct cctcagctag   1620
caccaagggc ccatcggtct tcccccctggc accctcctcc aagagcacct ctgggggcac  1680
agcggccctg ggctgcctgg tcaaggacta cttccccgaa ccggtgacgg tgtcgtggaa   1740
ctcaggcgcc ctgaccagcg gcgtgcacac cttcccggct gtcctacagt cctcaggact   1800
ctactccctc agcagcgtag tgaccgtgcc ctccagcagc ttgggcaccc agacctacat   1860
ctgcaacgtg aatcacaagc ccagcaacac caaggtggac aagaaagttg agcccaaatc   1920
ttgtgcggcc gcagaggtgc agctggtgga gtctgggggga ggcttcgtgc aggcggggga  1980
atctctgacg ctctcctgta caagttctac actgaccttc actccgtatc gcatggcctg   2040
gtaccgccag gctccaggga agcagcgtga tttagtcgcg gatattagta gtggtgatgg   2100
taggaccaca aactatgcgg acttcgcgaa gggccgattc accatctcca gagacaacat   2160
caagaacacg gtctttctgc gaatgactaa cctgaaacct gaggacacgg ccgtctacta   2220
ctgtaacacc ttcgtttcgt ttgtggggat tgcgcgttct tggggccagg ggacccaggt   2280
```

-continued

```
cactgtctcc tcagcggccg cagaacaaaa actcatctca gaagaggatc tgaatggggc   2340
cgtacatcac caccatcatc atgggagcta agcttggctg ttttggcgga tgagagaaga   2400
ttttcagcct gatacagatt aaatcagaac gcagaagcgg tctgataaaa cagaatttgc   2460
ctggcggcag tagcgcggtg gtcccacctg accccatgcc gaactcagaa gtgaaacgcc   2520
gtagcgccga tggtagtgtg gggtctcccc atgcgagagt agggaactgc caggcatcaa   2580
ataaaacgaa aggctcagtc gaaagactgg gcctttcgtt ttatctgttg tttgtcggtg   2640
aacgctctcc tgagtaggac aaatccgccg ggagcggatt tgaacgttgc gaagcaacgg   2700
cccggaggac cctggcgggc aggacgcccg ccataaactg ccaggcatca aattaagcag   2760
aaggccatcc tgacggatgg cctttttgcg tttctacaaa ctcttttgtt tatttttcta   2820
aatacattca aatatgtatc cgctcatgag acaataaccc tgataaatgc ttcaataata   2880
ttgaaaaagg aagagtatga gtattcaaca tttccgtgtc gcccttattc ccttttttgc   2940
ggcattttgc cttcctgttt ttgctcaccc agaaacgctg gtgaaagtaa aagatgctga   3000
agatcagttg ggtgcacgag tgggttacat cgaactggat ctcaacagcg gtaagatcct   3060
tgagagtttt cgccccgaag aacgttttcc aatgatgagc acttttaaag ttctgctatg   3120
tggcgcggta ttatcccgtg ttgacgccgg gcaagagcaa ctcggtcgcc gcatacacta   3180
ttctcagaat gacttggttg agtactcacc agtcacagaa aagcatctta cggatggcat   3240
gacagtaaga gaattatgca gtgctgccat aaccatgagt gataacactg cggccaactt   3300
acttctgaca acgatcggag gaccgaagga gctaaccgct tttttgcaca acatggggga   3360
tcatgtaact cgccttgatc gttgggaacc ggagctgaat gaagccatac caaacgacga   3420
gcgtgacacc acgatgcctg tagcaatggc aacaacgttg cgcaaactat taactggcga   3480
actacttact ctagcttccc ggcaacaatt aatagactgg atggaggcgg ataaagttgc   3540
aggaccactt ctgcgctcgg cccttccggc tggctggttt attgctgata aatctggagc   3600
cggtgagcgt gggtctcgcg gtatcattgc agcactgggg ccagatggta agccctcccg   3660
tatcgtagtt atctacacga cggggagtca ggcaactatg gatgaacgaa atagacagat   3720
cgctgagata ggtgcctcac tgattaagca ttggtaactg tcagaccaag tttactcata   3780
tatactttag attgatttaa aacttcattt ttaatttaaa aggatctagg tgaagatcct   3840
ttttgataat ctcatgacca aaatccctta acgtgagttt tcgttccact gagcgtcaga   3900
ccccgtagaa aagatcaaag gatcttcttg agatcctttt tttctgcgcg taatctgctg   3960
cttgcaaaca aaaaaaccac cgctaccagc ggtggtttgt ttgccggatc aagagctacc   4020
aactcttttt ccgaaggtaa ctggcttcag cagagcgcag ataccaaata ctgtccttct   4080
agtgtagccg tagttaggcc accacttcaa gaactctgta gcaccgccta catacctcgc   4140
tctgctaatc ctgttaccag tggctgctgc cagtggcgat aagtcgtgtc ttaccgggtt   4200
ggactcaaga cgatagttac cggataaggc gcagcggtcg ggctgaacgg ggggttcgtg   4260
cacacagccc agcttggagc gaacgaccta caccgaactg agatacctac agcgtgagca   4320
ttgagaaagc gccacgcttc ccgaagggag aaaggcggac aggtatccgg taagcggcag   4380
ggtcggaaca ggagagcgca cgagggagct tccaggggga aacgcctggt atctttatag   4440
tcctgtcggg tttcgccacc tctgacttga gcgtcgattt ttgtgatgct cgtcaggggg   4500
gcggagccta tggaaaaacg ccagcaacgc ggccttttta cggttcctgg ccttttgctg   4560
gccttttgct cacatgttct ttcctgcgtt atcccctgat tctgtggata accgtattac   4620
```

-continued

```
cgcctttgag tgagctgata ccgctcgccg cagccgaacg accgagcgca gcgagtcagt   4680
gagcgaggaa gcggaagagc gcctgatgcg gtattttctc cttacgcatc tgtgcggtat   4740
ttcacaccgc atatatggtg cactctcagt acaatctgct ctgatgccgc atagttaagc   4800
cagtatacac tccgctatcg ctacgtgact gggtcatggc tgcgccccga cacccgccaa   4860
cacccgctga cgcgccctga cgggcttgtc tgctcccggc atccgcttac agacaagctg   4920
tgaccgtctc cgggagctgc atgtgtcaga ggttttcacc gtcatcaccg aaacgcgcga   4980
ggcagctgcg gtaaagctca tcagcgtggt cgtgaagcga ttcacagatg tctgcctgtt   5040
catccgcgtc cagctcgttg agtttctcca gaagcgttaa tgtctggctt ctgataaagc   5100
gggccatgtt aagggcggtt ttttcctgtt tggtcacttg atgcctccgt gtaaggggga   5160
atttctgttc atgggggtaa tgataccgat gaaacgagag aggatgctca cgatacgggt   5220
tactgatgat gaacatgccc ggttactgga acgttgtgag ggtaaacaac tggcggtatg   5280
gatgcggcgg gaccagagaa aaatcactca gggtcaatgc cagcgcttcg ttaatacaga   5340
tgtaggtgtt ccacagggta gccagcagca tcctgcgatg cagatccgga acataatggt   5400
gcagggcgct gacttccgcg tttccagact ttacgaaaca cggaaaccga agaccattca   5460
tgttgttgct caggtcgcag acgttttgca gcagcagtcg cttcacgttc gctcgcgtat   5520
cggtgattca ttctgctaac cagtaaggca accccgccag cctagccggg tcctcaacga   5580
caggagcacg atcatgcgca cccgtggcca ggacccaacg ctgcccgaga tgcgccgcgt   5640
gcggctgctg gagatggcgg acgcgatgga tatgttctgc caagggttgg tttgcgcatt   5700
cacagttctc cgcaagaatt gattggctcc aattcttgga gtggtgaatc cgttagcgag   5760
gtgccgccgg cttccattca ggtcgaggtg gcccggctcc atgcaccgcg acgcaacgcg   5820
gggaggcaga caaggtatag ggcggcgcct acaatccatg ccaacccgtt ccatgtgctc   5880
gccgaggcgg cataaatcgc cgtgacgatc agcggtccag tgatcgaagt taggctggta   5940
agagccgcga gcgatccttg aagctgtccc tgatggtcgt catctacctg cctggacagc   6000
atggcctgca acgcgggcat cccgatgccg ccggaagcga gaagaatcat aatggggaag   6060
gccatccagc ctcgcgtcgc gaacgccagc aagacgtagc ccagcgcgtc ggccagcttg   6120
caattcgcgc taacttacat taattgcgtt gcgctcactg cccgctttcc agtcgggaaa   6180
cctgtcgtgc cagctgcatt aatgaatcgg ccaacgcgcg gggagaggcg gtttgcgtat   6240
tgggcgccag ggtggttttt cttttcacca gtgagacggg caacagctga ttgcccttca   6300
ccgcctggcc ctgagagagt tgcagcaagc ggtccacgct ggtttgcccc agcaggcgaa   6360
aatcctgttt gatggtggtt gacggcggga tataacatga gctgtcttcg gtatcgtcgt   6420
atcccactac cgagatatcc gcaccaacgc gcagcccgga ctcggtaatg gcgcgcattg   6480
cgcccagcgc catctgatcg ttggcaacca gcatcgcagt gggaacgatg ccctcattca   6540
gcatttgcat ggtttgttga aaaccggaca tggcactcca gtcgccttcc cgttccgcta   6600
tcggctgaat ttgattgcga gtgagatatt tatgccagcc agccagacgc agacgcgccg   6660
agacagaact taatggtccc gctaacagcg cgatttgctg atgacccaat gcgaccagat   6720
gctccacgcc cagtcgcgta ccgtcttcat gggagaaaat aatactgttg atgggtgtct   6780
ggtcagagac atcaagaaat aacgccggaa cattagtgca ggcagcttcc acagcaatgg   6840
catcctggtc atccagcgga tagttaatga tcagcccact gacgcgttgc gcgagaagat   6900
tgtgcaccgc cgctttacag gcttcgacgc cgcttcgttc taccatcgac accaccacgc   6960
tggcacccag ttgatcggcg cgagatttaa tcgccgcgac aatttgcgac ggcgcgtgca   7020
```

```
gggccagact ggaggtggca acgccaatca gcaacgactg tttgcccgcc agttgttgtg   7080

ccacgcggtt gggaatgtaa ttcagctccg ccatcgccgc ttccactttt tcccgcgttt   7140

tcgcagaaac gtggctggcc tggttcacca cgcgggaaac ggtctgataa gagacaccgg   7200

catactctgc gacatcgtat aacgttactg gtttcacatt caccac                  7246
```

<210> SEQ ID NO 13
<211> LENGTH: 6877
<212> TYPE: DNA
<213> ORGANISM: Artificial
<220> FEATURE:
<223> OTHER INFORMATION: Synthetic plasmid p14

<400> SEQUENCE: 13

```
cctgaattga ctctcttccg ggcgctatca tgccataccg cgaaaggttt tgcgccattc     60

gatggtgtca acgtaaatgc atgccgcttc gccttcgcgc gcgaattgca agctgatccg    120

gagcttatcg actgcacggt gcaccaatgc ttctggcgtc aggcagccat cggaagctgt    180

ggtatggctg tgcaggtcgt aaatcactgc ataattcgtg tcgctcaagg cgcactcccg    240

ttctggataa tgttttttgc gccgacatca taacggttct ggcaaatatt ctgaaatgag    300

ctgttgacaa ttaatcatcg gctcgtataa tgtgtggaat tgtgagcgga taacaatttc    360

acacaggaaa cagaattcca tatgaaatac ctattaccaa cagcagcagc tgggttatta    420

ttgctcgctg cgcagccggc catggccgag gtgcagctgg tggagtctgg gggaggcttc    480

gtgcaggcgg gggaatctct gacgctctcc tgtacaagtt ctacactgac cttcactccg    540

tatcgcatgg cctggtaccg ccaggctcca gggaagcagc gtgatttagt cgcggatatt    600

agtagtggtg atggtaggac cacaaactat gcggacttcg cgaagggccg attcaccatc    660

tccagagaca acatcaagaa cacggtcttt ctgcgaatga ctaacctgaa acctgaggac    720

acggccgtct actactgtaa caccttcgtt tcgtttgtgg ggattgcgcg ttcttggggc    780

caggggaccc aggtcaccgt ctcctcacgt acggtggctg caccatctgt cttcatcttc    840

ccgccatctg atgagcagtt gaaatctgga actgcctctg ttgtgtgcct gctgaataac    900

ttctatccca gagaggccaa agtacagtgg aaggtggata acgccctcca atcgggtaac    960

tcccaggaga gtgtcacaga gcaggacagc aaggacagca cctacagcct cagcagcacc   1020

ctgacgctga gcaaagcaga ctacgagaaa cacaaagtct acgcctgcga agtcacccat   1080

cagggcctga gctcgccggt gacaaagagc ttcaaccgcg gagagtgtgc aggtgattac   1140

aaagacgatg acgataagta ataaacagga aacagaagtc catatgaaat acctattgcc   1200

tacggcagcc gctggattgt tattactcgc ggcccagccg gccatggccg aggtgcagct   1260

ggtggagtct gggggagagt tggtgcaggc tgggggctct ctgagactct cctgtgcagc   1320

ctctggcctc accttcagta gctataacat gggctggttc cgccgggctc cagggaagga   1380

gcgtgagttt gtagcatcta ttacctggag tggtcgggac acattctatg cagactccgt   1440

gaagggccga ttcaccatct ccagagacaa cgccaagaac actgtttatc tgcaaatgag   1500

cagcctgaaa cctgaggaca cggccgttta ttattgtgct gcaaacccct ggccagtggc   1560

ggcgccacgt agtggcacct actggggcca agggacccag gtcaccgtct cctcagctag   1620

caccaagggc ccatcggtct tccccctggc accctcctcc aagagcacct ctgggggcac   1680

agcggccctg ggctgcctgg tcaaggacta cttccccgaa ccggtgacgg tgtcgtggaa   1740

ctcaggcgcc ctgaccagcg gcgtgcacac cttcccggct gtcctacagt cctcaggact   1800
```

-continued

```
ctactccctc agcagcgtag tgaccgtgcc ctccagcagc ttgggcaccc agacctacat   1860
ctgcaacgtg aatcacaagc ccagcaacac caaggtggac aagaaagttg agcccaaatc   1920
ttgtgcggcc gcagaacaaa aactcatctc agaagaggat ctgaatgggg ccgtacatca   1980
ccaccatcat catgggagct aagcttggct gttttggcgg atgagagaag attttcagcc   2040
tgatacagat taaatcagaa cgcagaagcg gtctgataaa acagaatttg cctggcggca   2100
gtagcgcggt ggtcccacct gaccccatgc cgaactcaga agtgaaacgc cgtagcgccg   2160
atggtagtgt ggggtctccc catgcgagag tagggaactg ccaggcatca aataaaacga   2220
aaggctcagt cgaaagactg ggcctttcgt tttatctgtt gtttgtcggt gaacgctctc   2280
ctgagtagga caaatccgcc gggagcggat ttgaacgttg cgaagcaacg gcccggagga   2340
ccctggcggg caggacgccc gccataaact gccaggcatc aaattaagca gaaggccatc   2400
ctgacggatg gcctttttgc gtttctacaa actcttttgt ttatttttct aaatacattc   2460
aaatatgtat ccgctcatga gacaataacc ctgataaatg cttcaataat attgaaaaag   2520
gaagagtatg agtattcaac atttccgtgt cgcccttatt cccttttttg cggcattttg   2580
ccttcctgtt tttgctcacc cagaaacgct ggtgaaagta aaagatgctg aagatcagtt   2640
gggtgcacga gtgggttaca tcgaactgga tctcaacagc ggtaagatcc ttgagagttt   2700
tcgccccgaa gaacgttttc caatgatgag cacttttaaa gttctgctat gtggcgcggt   2760
attatcccgt gttgacgccg ggcaagagca actcggtcgc cgcatacact attctcagaa   2820
tgacttggtt gagtactcac cagtcacaga aaagcatctt acggatggca tgacagtaag   2880
agaattatgc agtgctgcca taaccatgag tgataacact gcggccaact tacttctgac   2940
aacgatcgga ggaccgaagg agctaaccgc ttttttgcac aacatggggg atcatgtaac   3000
tcgccttgat cgttgggaac cggagctgaa tgaagccata ccaaacgacg agcgtgacac   3060
cacgatgcct gtagcaatgg caacaacgtt gcgcaaacta ttaactggcg aactacttac   3120
tctagcttcc cggcaacaat taatagactg gatggaggcg gataaagttg caggaccact   3180
tctgcgctcg gcccttccgg ctggctggtt tattgctgat aaatctggag ccggtgagcg   3240
tgggtctcgc ggtatcattg cagcactggg gccagatggt aagccctccc gtatcgtagt   3300
tatctacacg acggggagtc aggcaactat ggatgaacga aatagacaga tcgctgagat   3360
aggtgcctca ctgattaagc attggtaact gtcagaccaa gtttactcat atatacttta   3420
gattgattta aaacttcatt tttaatttaa aaggatctag gtgaagatcc tttttgataa   3480
tctcatgacc aaaatccctt aacgtgagtt ttcgttccac tgagcgtcag accccgtaga   3540
aaagatcaaa ggatcttctt gagatccttt ttttctgcgc gtaatctgct gcttgcaaac   3600
aaaaaaacca ccgctaccag cggtggtttg tttgccggat caagagctac caactctttt   3660
tccgaaggta actggcttca gcagagcgca gataccaaat actgtccttc tagtgtagcc   3720
gtagttaggc caccacttca agaactctgt agcaccgcct acatacctcg ctctgctaat   3780
cctgttacca gtggctgctg ccagtggcga taagtcgtgt cttaccgggt tggactcaag   3840
acgatagtta ccggataagg cgcagcggtc gggctgaacg gggggttcgt gcacacagcc   3900
cagcttggag cgaacgacct acaccgaact gagataccta cagcgtgagc attgagaaag   3960
cgccacgctt cccgaaggga gaaaggcgga caggtatccg gtaagcggca gggtcggaac   4020
aggagagcgc acgagggagc ttccaggggg aaacgcctgg tatctttata gtcctgtcgg   4080
gtttcgccac ctctgacttg agcgtcgatt tttgtgatgc tcgtcagggg ggcggagcct   4140
atggaaaaac gccagcaacg cggccttttt acggttcctg gccttttgct ggccttttgc   4200
```

-continued

```
tcacatgttc tttcctgcgt tatcccctga ttctgtggat aaccgtatta ccgcctttga   4260
gtgagctgat accgctcgcc gcagccgaac gaccgagcgc agcgagtcag tgagcgagga   4320
agcggaagag cgcctgatgc ggtattttct ccttacgcat ctgtgcggta tttcacaccg   4380
catatatggt gcactctcag tacaatctgc tctgatgccg catagttaag ccagtataca   4440
ctccgctatc gctacgtgac tgggtcatgg ctgcgccccg acacccgcca acacccgctg   4500
acgcgccctg acgggcttgt ctgctcccgg catccgctta cagacaagct gtgaccgtct   4560
ccgggagctg catgtgtcag aggttttcac cgtcatcacc gaaacgcgcg aggcagctgc   4620
ggtaaagctc atcagcgtgg tcgtgaagcg attcacagat gtctgcctgt tcatccgcgt   4680
ccagctcgtt gagtttctcc agaagcgtta atgtctggct tctgataaag cgggccatgt   4740
taagggcggt tttttcctgt ttggtcactt gatgcctccg tgtaaggggg aatttctgtt   4800
catgggggta atgataccga tgaaacgaga gaggatgctc acgatacggg ttactgatga   4860
tgaacatgcc cggttactgg aacgttgtga gggtaaacaa ctggcggtat ggatgcggcg   4920
ggaccagaga aaaatcactc agggtcaatg ccagcgcttc gttaatacag atgtaggtgt   4980
tccacagggt agccagcagc atcctgcgat gcagatccgg aacataatgg tgcagggcgc   5040
tgacttccgc gtttccagac tttacgaaac acggaaaccg aagaccattc atgttgttgc   5100
tcaggtcgca gacgttttgc agcagcagtc gcttcacgtt cgctcgcgta tcggtgattc   5160
attctgctaa ccagtaaggc aaccccgcca gcctagccgg gtcctcaacg acaggagcac   5220
gatcatgcgc acccgtggcc aggacccaac gctgcccgag atgcgccgcg tgcggctgct   5280
ggagatggcg gacgcgatgg atatgttctg ccaagggttg gtttgcgcat tcacagttct   5340
ccgcaagaat tgattggctc caattcttgg agtggtgaat ccgttagcga ggtgccgccg   5400
gcttccattc aggtcgaggt ggcccggctc catgcaccgc gacgcaacgc ggggaggcag   5460
acaaggtata gggcggcgcc tacaatccat gccaacccgt tccatgtgct cgccgaggcg   5520
gcataaatcg ccgtgacgat cagcggtcca gtgatcgaag ttaggctggt aagagccgcg   5580
agcgatcctt gaagctgtcc ctgatggtcg tcatctacct gcctggacag catggcctgc   5640
aacgcgggca tcccgatgcc gccggaagcg agaagaatca taatggggaa ggccatccag   5700
cctcgcgtcg cgaacgccag caagacgtag cccagcgcgt cggccagctt gcaattcgcg   5760
ctaacttaca ttaattgcgt tgcgctcact gcccgctttc cagtcgggaa acctgtcgtg   5820
ccagctgcat taatgaatcg gccaacgcgc ggggagaggc ggtttgcgta ttgggcgcca   5880
gggtggtttt tcttttcacc agtgagacgg gcaacagctg attgcccttc accgcctggc   5940
cctgagagag ttgcagcaag cggtccacgc tggtttgccc cagcaggcga aaatcctgtt   6000
tgatggtggt tgacggcggg atataacatg agctgtcttc ggtatcgtcg tatcccacta   6060
ccgagatatc cgcaccaacg cgcagcccgg actcggtaat ggcgcgcatt gcgcccagcg   6120
ccatctgatc gttggcaacc agcatcgcag tgggaacgat gccctcattc agcatttgca   6180
tggtttgttg aaaaccggac atggcactcc agtcgccttc ccgttccgct atcggctgaa   6240
tttgattgcg agtgagatat ttatgccagc cagccagacg cagacgcgcc gagacagaac   6300
ttaatggtcc cgctaacagc gcgatttgct gatgacccaa tgcgaccaga tgctccacgc   6360
ccagtcgcgt accgtcttca tgggagaaaa taatactgtt gatgggtgtc tggtcagaga   6420
catcaagaaa taacgccgga acattagtgc aggcagcttc cacagcaatg gcatcctggt   6480
catccagcgg atagttaatg atcagcccac tgacgcgttg cgcgagaaga ttgtgcaccg   6540
```

-continued ccgctttaca ggcttcgacg ccgcttcgtt ctaccatcga caccaccacg ctggcaccca 6600
gttgatcggc gcgagattta atcgccgcga caatttgcga cggcgcgtgc agggccagac 6660
tggaggtggc aacgccaatc agcaacgact gtttgcccgc cagttgttgt gccacgcggt 6720
tgggaatgta attcagctcc gccatcgccg cttccacttt ttcccgcgtt ttcgcagaaa 6780
cgtggctggc ctggttcacc acgcgggaaa cggtctgata agagacaccg gcatactctg 6840
cgacatcgta taacgttact ggtttcacat tcaccac 6877

<210> SEQ ID NO 14
<211> LENGTH: 7237
<212> TYPE: DNA
<213> ORGANISM: Artificial
<220> FEATURE:
<223> OTHER INFORMATION: Synthetic plasmid p515

<400> SEQUENCE: 14
cctgaattga ctctcttccg ggcgctatca tgccataccg cgaaaggttt tgcgccattc 60
gatggtgtca acgtaaatgc atgccgcttc gccttcgcgc gcgaattgca agctgatccg 120
gagcttatcg actgcacggt gcaccaatgc ttctggcgtc aggcagccat cggaagctgt 180
ggtatggctg tgcaggtcgt aaatcactgc ataattcgtg tcgctcaagg cgcactcccg 240
ttctggataa tgttttttgc gccgacatca taacggttct ggcaaatatt ctgaaatgag 300
ctgttgacaa ttaatcatcg gctcgtataa tgtgtggaat tgtgagcgga taacaatttc 360
acacaggaaa cagaattcca tatgaaatac ctattaccaa cagcagcagc tgggttatta 420
ttgctcgctg cgcagccggc catggccgag gtgcagctgg tggagtctgg gggaggcttc 480
gtgcaggcgg gggaatctct gacgctctcc tgtacaagtt ctacactgac cttcactccg 540
tatcgcatgg cctggtaccg ccaggctcca gggaagcagc gtgatttagt cgcggatatt 600
agtagtggtg atggtaggac cacaaactat gcggacttcg cgaagggccg attcaccatc 660
tccagagaca acatcaagaa cacggtcttt ctgcgaatga ctaacctgaa acctgaggac 720
acggccgtct actactgtaa caccttcgtt tcgtttgtgg ggattgcgcg ttcttggggc 780
caggggaccc aggtcaccgt ctcctcacgt acggtggctg caccatctgt cttcatcttc 840
ccgccatctg atgagcagtt gaaatctgga actgcctctg ttgtgtgcct gctgaataac 900
ttctatccca gagaggccaa agtacagtgg aaggtggata acgccctcca atcgggtaac 960
tcccaggaga gtgtcacaga gcaggacagc aaggacagca cctacagcct cagcagcacc 1020
ctgacgctga gcaaagcaga ctacgagaaa cacaaagtct acgcctgcga agtcacccat 1080
cagggcctga gctcgccggt gacaaagagc ttcaaccgcg gagagtgtgc aggtgattac 1140
aaagacgatg acgataagta ataaacagga aacagaagtc catatgaaat acctattgcc 1200
tacggcagcc gctggattgt tattactcgc ggcccagccg gccatggccg aggtgcagct 1260
ggtggagtct gggggaggct tagtgcagcc tggggagtct ctgacactct cctgtgtagt 1320
tgctggaagc atcttcagct tcgccatgag ctggtatcgc caggctccag gaaaagagcg 1380
cgaattggtc gcacgtattg gttcggatga tcgggtaacg tacgcagatt ccgtgaaggg 1440
ccgatttacc atctccagag acaacatcaa gcgcacggcg ggcctgcaga tgaacagcct 1500
gaaacctgag gacacggccg tctactactg caatgcccaa acagatttga gggattggac 1560
tgtgcgagag tactggggcc aggggaccca ggtcaccgtc tcctcagcta gcaccaaggg 1620
cccatcggtc ttcccccctgg caccctcctc caagagcacc tctgggggca cagcggccct 1680
gggctgcctg gtcaaggact acttccccga accggtgacg gtgtcgtgga actcaggcgc 1740

-continued

```
cctgaccagc ggcgtgcaca ccttcccggc tgtcctacag tcctcaggac tctactccct   1800
cagcagcgta gtgaccgtgc cctccagcag cttgggcacc cagacctaca tctgcaacgt   1860
gaatcacaag cccagcaaca ccaaggtgga caagaaagtt gagcccaaat cttgtgcggc   1920
cgcagaggtg cagctggtgg agtctggggg aggcttcgtg caggcggggg aatctctgac   1980
gctctcctgt acaagttcta cactgacctt cactccgtat cgcatggcct ggtaccgcca   2040
ggctccaggg aagcagcgtg atttagtcgc ggatattagt agtggtgatg gtaggaccac   2100
aaactatgcg gacttcgcga agggccgatt caccatctcc agagacaaca tcaagaacac   2160
ggtctttctg cgaatgacta acctgaaacc tgaggacacg gccgtctact actgtaacac   2220
cttcgtttcg tttgtgggga ttgcgcgttc ttggggccag gggacccagg tcactgtctc   2280
ctcagcggcc gcagaacaaa aactcatctc agaagaggat ctgaatgggg ccgtacatca   2340
ccaccatcat catgggagct aagcttggct gttttggcgg atgagagaag attttcagcc   2400
tgatacagat taaatcagaa cgcagaagcg gtctgataaa acagaatttg cctggcggca   2460
gtagcgcggt ggtcccacct gaccccatgc cgaactcaga agtgaaacgc cgtagcgccg   2520
atggtagtgt ggggtctccc catgcgagag tagggaactg ccaggcatca aataaaacga   2580
aaggctcagt cgaaagactg ggcctttcgt tttatctgtt gtttgtcggt gaacgctctc   2640
ctgagtagga caaatccgcc gggagcggat ttgaacgttg cgaagcaacg gcccggagga   2700
ccctggcggg caggacgccc gccataaact gccaggcatc aaattaagca gaaggccatc   2760
ctgacggatg gcctttttgc gtttctacaa actcttttgt ttatttttct aaatacattc   2820
aaatatgtat ccgctcatga gacaataacc ctgataaatg cttcaataat attgaaaaag   2880
gaagagtatg agtattcaac atttccgtgt cgcccttatt cccttttttg cggcattttg   2940
ccttcctgtt tttgctcacc cagaaacgct ggtgaaagta aaagatgctg aagatcagtt   3000
gggtgcacga gtgggttaca tcgaactgga tctcaacagc ggtaagatcc ttgagagttt   3060
tcgccccgaa gaacgttttc caatgatgag cacttttaaa gttctgctat gtggcgcggt   3120
attatcccgt gttgacgccg ggcaagagca actcggtcgc cgcatacact attctcagaa   3180
tgacttggtt gagtactcac cagtcacaga aaagcatctt acggatggca tgacagtaag   3240
agaattatgc agtgctgcca taaccatgag tgataacact gcggccaact tacttctgac   3300
aacgatcgga ggaccgaagg agctaaccgc ttttttgcac aacatggggg atcatgtaac   3360
tcgccttgat cgttgggaac cggagctgaa tgaagccata ccaaacgacg agcgtgacac   3420
cacgatgcct gtagcaatgg caacaacgtt gcgcaaacta ttaactggcg aactacttac   3480
tctagcttcc cggcaacaat taatagactg gatggaggcg gataaagttg caggaccact   3540
tctgcgctcg gcccttccgg ctggctggtt tattgctgat aaatctggag ccggtgagcg   3600
tgggtctcgc ggtatcattg cagcactggg gccagatggt aagccctccc gtatcgtagt   3660
tatctacacg acggggagtc aggcaactat ggatgaacga aatagacaga tcgctgagat   3720
aggtgcctca ctgattaagc attggtaact gtcagaccaa gtttactcat atatacttta   3780
gattgattta aaacttcatt tttaatttaa aaggatctag gtgaagatcc tttttgataa   3840
tctcatgacc aaaatccctt aacgtgagtt ttcgttccac tgagcgtcag accccgtaga   3900
aaagatcaaa ggatcttctt gagatccttt ttttctgcgc gtaatctgct gcttgcaaac   3960
aaaaaaacca ccgctaccag cggtggtttg tttgccggat caagagctac caactctttt   4020
tccgaaggta actggcttca gcagagcgca gataccaaat actgtccttc tagtgtagcc   4080
```

-continued gtagttaggc caccacttca agaactctgt agcaccgcct acatacctcg ctctgctaat 4140
cctgttacca gtggctgctg ccagtggcga taagtcgtgt cttaccgggt tggactcaag 4200
acgatagtta ccggataagg cgcagcggtc gggctgaacg gggggttcgt gcacacagcc 4260
cagcttggag cgaacgacct acaccgaact gagataccta cagcgtgagc attgagaaag 4320
cgccacgctt cccgaaggga gaaaggcgga caggtatccg gtaagcggca gggtcggaac 4380
aggagagcgc acgagggagc ttccaggggg aaacgcctgg tatctttata gtcctgtcgg 4440
gtttcgccac ctctgacttg agcgtcgatt tttgtgatgc tcgtcagggg ggcggagcct 4500
atggaaaaac gccagcaacg cggccttttt acggttcctg gccttttgct ggccttttgc 4560
tcacatgttc tttcctgcgt tatcccctga ttctgtggat aaccgtatta ccgcctttga 4620
gtgagctgat accgctcgcc gcagccgaac gaccgagcgc agcgagtcag tgagcgagga 4680
agcggaagag cgcctgatgc ggtattttct ccttacgcat ctgtgcggta tttcacaccg 4740
catatatggt gcactctcag tacaatctgc tctgatgccg catagttaag ccagtataca 4800
ctccgctatc gctacgtgac tgggtcatgg ctgcgccccg acacccgcca acacccgctg 4860
acgcgccctg acgggcttgt ctgctcccgg catccgctta cagacaagct gtgaccgtct 4920
ccgggagctg catgtgtcag aggttttcac cgtcatcacc gaaacgcgcg aggcagctgc 4980
ggtaaagctc atcagcgtgg tcgtgaagcg attcacagat gtctgcctgt tcatccgcgt 5040
ccagctcgtt gagtttctcc agaagcgtta atgtctggct tctgataaag cgggccatgt 5100
taagggcggt tttttcctgt ttggtcactt gatgcctccg tgtaaggggg aatttctgtt 5160
catgggggta atgataccga tgaaacgaga gaggatgctc acgatacggg ttactgatga 5220
tgaacatgcc cggttactgg aacgttgtga gggtaaacaa ctggcggtat ggatgcggcg 5280
ggaccagaga aaaatcactc agggtcaatg ccagcgcttc gttaatacag atgtaggtgt 5340
tccacagggt agccagcagc atcctgcgat gcagatccgg aacataatgg tgcagggcgc 5400
tgacttccgc gtttccagac tttacgaaac acggaaaccg aagaccattc atgttgttgc 5460
tcaggtcgca gacgttttgc agcagcagtc gcttcacgtt cgctcgcgta tcggtgattc 5520
attctgctaa ccagtaaggc aaccccgcca gcctagccgg gtcctcaacg acaggagcac 5580
gatcatgcgc acccgtggcc aggacccaac gctgcccgag atgcgccgcg tgcggctgct 5640
ggagatggcg gacgcgatgg atatgttctg ccaagggttg gtttgcgcat tcacagttct 5700
ccgcaagaat tgattggctc caattcttgg agtggtgaat ccgttagcga ggtgccgccg 5760
gcttccattc aggtcgaggt ggcccggctc catgcaccgc gacgcaacgc ggggaggcag 5820
acaaggtata gggcggcgcc tacaatccat gccaacccgt tccatgtgct cgccgaggcg 5880
gcataaatcg ccgtgacgat cagcggtcca gtgatcgaag ttaggctggt aagagccgcg 5940
agcgatcctt gaagctgtcc ctgatggtcg tcatctacct gcctggacag catggcctgc 6000
aacgcgggca tcccgatgcc gccggaagcg agaagaatca taatggggaa ggccatccag 6060
cctcgcgtcg cgaacgccag caagacgtag cccagcgcgt cggccagctt gcaattcgcg 6120
ctaacttaca ttaattgcgt tgcgctcact gcccgctttc cagtcgggaa acctgtcgtg 6180
ccagctgcat taatgaatcg gccaacgcgc ggggagaggc ggtttgcgta ttgggcgcca 6240
gggtggtttt tcttttcacc agtgagacgg gcaacagctg attgcccttc accgcctggc 6300
cctgagagag ttgcagcaag cggtccacgc tggtttgccc cagcaggcga aaatcctgtt 6360
tgatggtggt tgacggcggg atataacatg agctgtcttc ggtatcgtcg tatcccacta 6420
ccgagatatc cgcaccaacg cgcagcccgg actcggtaat ggcgcgcatt gcgcccagcg 6480

-continued

```
ccatctgatc gttggcaacc agcatcgcag tgggaacgat gccctcattc agcatttgca   6540

tggtttgttg aaaaccggac atggcactcc agtcgccttc ccgttccgct atcggctgaa   6600

tttgattgcg agtgagatat ttatgccagc cagccagacg cagacgcgcc gagacagaac   6660

ttaatggtcc cgctaacagc gcgatttgct gatgacccaa tgcgaccaga tgctccacgc   6720

ccagtcgcgt accgtcttca tgggagaaaa taatactgtt gatgggtgtc tggtcagaga   6780

catcaagaaa taacgccgga acattagtgc aggcagcttc cacagcaatg gcatcctggt   6840

catccagcgg atagttaatg atcagcccac tgacgcgttg cgcgagaaga ttgtgcaccg   6900

ccgctttaca ggcttcgacg ccgcttcgtt ctaccatcga caccaccacg ctggcaccca   6960

gttgatcggc gcgagattta atcgccgcga caatttgcga cggcgcgtgc agggccagac   7020

tggaggtggc aacgccaatc agcaacgact gtttgcccgc cagttgttgt gccacgcggt   7080

tgggaatgta attcagctcc gccatcgccg cttccacttt ttcccgcgtt ttcgcagaaa   7140

cgtggctggc ctggttcacc acgcgggaaa cggtctgata agagacaccg gcatactctg   7200

cgacatcgta taacgttact ggtttcacat tcaccac                           7237
```

<210> SEQ ID NO 15
<211> LENGTH: 6868
<212> TYPE: DNA
<213> ORGANISM: Artificial
<220> FEATURE:
<223> OTHER INFORMATION: Synthetic plasmid p15

<400> SEQUENCE: 15

```
ttgtttattt ttctaaatac attcaaatat gtatccgctc atgagacaat aaccctgata     60

aatgcttcaa taatattgaa aaaggaagag tatgagtatt caacatttcc gtgtcgccct    120

tattcccttt tttgcggcat tttgccttcc tgtttttgct cacccagaaa cgctggtgaa    180

agtaaaagat gctgaagatc agttgggtgc acgagtgggt tacatcgaac tggatctcaa    240

cagcggtaag atccttgaga gttttcgccc cgaagaacgt tttccaatga tgagcacttt    300

taaagttctg ctatgtggcg cggtattatc ccgtgttgac gccgggcaag agcaactcgg    360

tcgccgcata cactattctc agaatgactt ggttgagtac tcaccagtca cagaaaagca    420

tcttacggat ggcatgacag taagagaatt atgcagtgct gccataacca tgagtgataa    480

cactgcggcc aacttacttc tgacaacgat cggaggaccg aaggagctaa ccgctttttt    540

gcacaacatg ggggatcatg taactcgcct tgatcgttgg gaaccggagc tgaatgaagc    600

cataccaaac gacgagcgtg acaccacgat gcctgtagca atggcaacaa cgttgcgcaa    660

actattaact ggcgaactac ttactctagc ttcccggcaa caattaatag actggatgga    720

ggcggataaa gttgcaggac cacttctgcg ctcggccctt ccggctggct ggtttattgc    780

tgataaatct ggagccggtg agcgtgggtc tcgcggtatc attgcagcac tggggccaga    840

tggtaagccc tcccgtatcg tagttatcta cacgacgggg agtcaggcaa ctatggatga    900

acgaaataga cagatcgctg agataggtgc ctcactgatt aagcattggt aactgtcaga    960

ccaagtttac tcatatatac tttagattga tttaaaactt catttttaat ttaaaaggat   1020

ctaggtgaag atcctttttg ataatctcat gaccaaaatc ccttaacgtg agttttcgtt   1080

ccactgagcg tcagaccccg tagaaaagat caaaggatct tcttgagatc cttttttct    1140

gcgcgtaatc tgctgcttgc aaacaaaaaa accaccgcta ccagcggtgg tttgtttgcc   1200

ggatcaagag ctaccaactc tttttccgaa ggtaactggc ttcagcagag cgcagatacc   1260
```

-continued

```
aaatactgtc cttctagtgt agccgtagtt aggccaccac ttcaagaact ctgtagcacc   1320
gcctacatac ctcgctctgc taatcctgtt accagtggct gctgccagtg gcgataagtc   1380
gtgtcttacc gggttggact caagacgata gttaccggat aaggcgcagc ggtcgggctg   1440
aacggggggt tcgtgcacac agcccagctt ggagcgaacg acctacaccg aactgagata   1500
cctacagcgt gagcattgag aaagcgccac gcttcccgaa gggagaaagg cggacaggta   1560
tccggtaagc ggcagggtcg gaacaggaga gcgcacgagg gagcttccag ggggaaacgc   1620
ctggtatctt tatagtcctg tcgggtttcg ccacctctga cttgagcgtc gatttttgtg   1680
atgctcgtca ggggggcgga gcctatggaa aaacgccagc aacgcggcct ttttacggtt   1740
cctggccttt tgctggcctt ttgctcacat gttctttcct gcgttatccc ctgattctgt   1800
ggataaccgt attaccgcct ttgagtgagc tgataccgct cgccgcagcc gaacgaccga   1860
gcgcagcgag tcagtgagcg aggaagcgga agagcgcctg atgcggtatt ttctccttac   1920
gcatctgtgc ggtatttcac accgcatata tggtgcactc tcagtacaat ctgctctgat   1980
gccgcatagt taagccagta tacactccgc tatcgctacg tgactgggtc atggctgcgc   2040
cccgacaccc gccaacaccc gctgacgcgc cctgacgggc ttgtctgctc ccggcatccg   2100
cttacagaca agctgtgacc gtctccggga gctgcatgtg tcagaggttt tcaccgtcat   2160
caccgaaacg cgcgaggcag ctgcggtaaa gctcatcagc gtggtcgtga agcgattcac   2220
agatgtctgc ctgttcatcc gcgtccagct cgttgagttt ctccagaagc gttaatgtct   2280
ggcttctgat aaagcgggcc atgttaaggg cggttttttc ctgtttggtc acttgatgcc   2340
tccgtgtaag ggggaatttc tgttcatggg ggtaatgata ccgatgaaac gagagaggat   2400
gctcacgata cgggttactg atgatgaaca tgcccggtta ctggaacgtt gtgagggtaa   2460
acaactggcg gtatggatgc ggcgggacca gagaaaaatc actcagggtc aatgccagcg   2520
cttcgttaat acagatgtag gtgttccaca gggtagccag cagcatcctg cgatgcagat   2580
ccggaacata atggtgcagg gcgctgactt ccgcgtttcc agactttacg aaacacggaa   2640
accgaagacc attcatgttg ttgctcaggt cgcagacgtt ttgcagcagc agtcgcttca   2700
cgttcgctcg cgtatcggtg attcattctg ctaaccagta aggcaacccc gccagcctag   2760
ccgggtcctc aacgacagga gcacgatcat gcgcacccgt ggccaggacc caacgctgcc   2820
cgagatgcgc cgcgtgcggc tgctggagat ggcggacgcg atggatatgt tctgccaagg   2880
gttggtttgc gcattcacag ttctccgcaa gaattgattg gctccaattc ttggagtggt   2940
gaatccgtta gcgaggtgcc gccggcttcc attcaggtcg aggtggcccg gctccatgca   3000
ccgcgacgca acgcggggag gcagacaagg tatagggcgg cgcctacaat ccatgccaac   3060
ccgttccatg tgctcgccga ggcggcataa atcgccgtga cgatcagcgg tccagtgatc   3120
gaagttaggc tggtaagagc cgcgagcgat ccttgaagct gtccctgatg gtcgtcatct   3180
acctgcctgg acagcatggc ctgcaacgcg ggcatcccga tgccgccgga agcgagaaga   3240
atcataatgg ggaaggccat ccagcctcgc gtcgcgaacg ccagcaagac gtagcccagc   3300
gcgtcggcca gcttgcaatt cgcgctaact tacattaatt gcgttgcgct cactgcccgc   3360
tttccagtcg ggaaacctgt cgtgccagct gcattaatga atcggccaac gcgcggggag   3420
aggcggtttg cgtattgggc gccagggtgg tttttctttt caccagtgag acgggcaaca   3480
gctgattgcc cttcaccgcc tggccctgag agagttgcag caagcggtcc acgctggttt   3540
gccccagcag gcgaaaatcc tgtttgatgg tggttgacgg cgggatataa catgagctgt   3600
cttcggtatc gtcgtatccc actaccgaga tatccgcacc aacgcgcagc ccggactcgg   3660
```

-continued

```
taatggcgcg cattgcgccc agcgccatct gatcgttggc aaccagcatc gcagtgggaa   3720
cgatgccctc attcagcatt tgcatggttt gttgaaaacc ggacatggca ctccagtcgc   3780
cttcccgttc cgctatcggc tgaatttgat tgcgagtgag atatttatgc cagccagcca   3840
gacgcagacg cgccgagaca gaacttaatg gtcccgctaa cagcgcgatt tgctgatgac   3900
ccaatgcgac cagatgctcc acgcccagtc gcgtaccgtc ttcatgggag aaaataatac   3960
tgttgatggg tgtctggtca gagacatcaa gaaataacgc cggaacatta gtgcaggcag   4020
cttccacagc aatggcatcc tggtcatcca gcggatagtt aatgatcagc ccactgacgc   4080
gttgcgcgag aagattgtgc accgccgctt tacaggcttc gacgccgctt cgttctacca   4140
tcgacaccac cacgctggca cccagttgat cggcgcgaga tttaatcgcc gcgacaattt   4200
gcgacggcgc gtgcagggcc agactggagg tggcaacgcc aatcagcaac gactgtttgc   4260
ccgccagttg ttgtgccacg cggttgggaa tgtaattcag ctccgccatc gccgcttcca   4320
ctttttcccg cgttttcgca gaaacgtggc tggcctggtt caccacgcgg gaaacggtct   4380
gataagagac accggcatac tctgcgacat cgtataacgt tactggtttc acattcacca   4440
ccctgaattg actctcttcc gggcgctatc atgccatacc gcgaaaggtt ttgcgccatt   4500
cgatggtgtc aacgtaaatg catgccgctt cgccttcgcg cgcgaattgc aagctgatcc   4560
ggagcttatc gactgcacgg tgcaccaatg cttctggcgt caggcagcca tcggaagctg   4620
tggtatggct gtgcaggtcg taaatcactg cataattcgt gtcgctcaag gcgcactccc   4680
gttctggata atgttttttg cgccgacatc ataacggttc tggcaaatat tctgaaatga   4740
gctgttgaca attaatcatc ggctcgtata atgtgtggaa ttgtgagcgg ataacaattt   4800
cacacaggaa acagaattcc atatgaaata cctattacca acagcagcag ctgggttatt   4860
attgctcgct gcgcagccgg ccatggccga ggtgcagctg gtggagtctg ggggaggctt   4920
cgtgcaggcg ggggaatctc tgacgctctc ctgtacaagt tctacactga ccttcactcc   4980
gtatcgcatg gcctggtacc gccaggctcc agggaagcag cgtgatttag tcgcggatat   5040
tagtagtggt gatggtagga ccacaaacta tgcggacttc gcgaagggcc gattcaccat   5100
ctccagagac aacatcaaga acacggtctt tctgcgaatg actaacctga aacctgagga   5160
cacggccgtc tactactgta acaccttcgt ttcgtttgtg gggattgcgc gttcttgggg   5220
ccaggggacc caggtcaccg tctcctcacg tacggtggct gcaccatctg tcttcatctt   5280
cccgccatct gatgagcagt tgaaatctgg aactgcctct gttgtgtgcc tgctgaataa   5340
cttctatccc agagaggcca aagtacagtg gaaggtggat aacgccctcc aatcgggtaa   5400
ctcccaggag agtgtcacag agcaggacag caaggacagc acctacagcc tcagcagcac   5460
cctgacgctg agcaaagcag actacgagaa acacaaagtc tacgcctgcg aagtcaccca   5520
tcagggcctg agctcgccgg tgacaaagag cttcaaccgc ggagagtgtg caggtgatta   5580
caaagacgat gacgataagt aataaacagg aaacagaagt ccatatgaaa tacctattgc   5640
ctacggcagc cgctggattg ttattactcg cggcccagcc ggccatggcc gaggtgcagc   5700
tggtggagtc tgggggaggc ttagtgcagc ctggggagtc tctgacactc tcctgtgtag   5760
ttgctggaag catcttcagc ttcgccatga gctggtatcg ccaggctcca ggaaaagagc   5820
gcgaattggt cgcacgtatt ggttcggatg atcgggtaac gtacgcagat tccgtgaagg   5880
gccgatttac catctccaga gacaacatca agcgcacggc gggcctgcag atgaacagcc   5940
tgaaacctga ggacacggcc gtctactact gcaatgccca aacagatttg agggattgga   6000
```

-continued

```
ctgtgcgaga gtactggggc caggggaccc aggtcaccgt ctcctcagct agcaccaagg   6060

gcccatcggt cttcccctg gcaccctcct ccaagagcac ctctgggggc acagcggccc   6120

tgggctgcct ggtcaaggac tacttccccg aaccggtgac ggtgtcgtgg aactcaggcg   6180

ccctgaccag cggcgtgcac accttcccgg ctgtcctaca gtcctcagga ctctactccc   6240

tcagcagcgt agtgaccgtg ccctccagca gcttgggcac ccagacctac atctgcaacg   6300

tgaatcacaa gcccagcaac accaaggtgg acaagaaagt tgagcccaaa tcttgtgcgg   6360

ccgcagaaca aaaactcatc tcagaagagg atctgaatgg ggccgtacat caccaccatc   6420

atcatgggag ctaagcttgg ctgttttggc ggatgagaga agattttcag cctgatacag   6480

attaaatcag aacgcagaag cggtctgata aaacagaatt tgcctggcgg cagtagcgcg   6540

gtggtcccac ctgaccccat gccgaactca gaagtgaaac gccgtagcgc cgatggtagt   6600

gtggggtctc cccatgcgag agtagggaac tgccaggcat caaataaaac gaaaggctca   6660

gtcgaaagac tgggcctttc gttttatctg ttgtttgtcg gtgaacgctc tcctgagtag   6720

gacaaatccg ccgggagcgg atttgaacgt tgcgaagcaa cggcccggag gaccctggcg   6780

ggcaggacgc ccgccataaa ctgccaggca tcaaattaag cagaaggcca tcctgacgga   6840

tggccttttt gcgtttctac aaactctt                                      6868
```

```
<210> SEQ ID NO 16
<211> LENGTH: 6536
<212> TYPE: DNA
<213> ORGANISM: Artificial
<220> FEATURE:
<223> OTHER INFORMATION: Synthetic plasmid p1201

<400> SEQUENCE: 16

ttgtttattt ttctaaatac attcaaatat gtatccgctc atgagacaat aaccctgata     60

aatgcttcaa taatattgaa aaaggaagag tatgagtatt caacatttcc gtgtcgccct    120

tattcccttt tttgcggcat tttgccttcc tgtttttgct cacccagaaa cgctggtgaa    180

agtaaaagat gctgaagatc agttgggtgc acgagtgggt tacatcgaac tggatctcaa    240

cagcggtaag atccttgaga gttttcgccc cgaagaacgt tttccaatga tgagcacttt    300

taaagttctg ctatgtggcg cggtattatc ccgtgttgac gccgggcaag agcaactcgg    360

tcgccgcata cactattctc agaatgactt ggttgagtac tcaccagtca cagaaaagca    420

tcttacggat ggcatgacag taagagaatt atgcagtgct gccataacca tgagtgataa    480

cactgcggcc aacttacttc tgacaacgat cggaggaccg aaggagctaa ccgctttttt    540

gcacaacatg ggggatcatg taactcgcct tgatcgttgg gaaccggagc tgaatgaagc    600

cataccaaac gacgagcgtg acaccacgat gcctgtagca atggcaacaa cgttgcgcaa    660

actattaact ggcgaactac ttactctagc ttcccggcaa caattaatag actggatgga    720

ggcggataaa gttgcaggac cacttctgcg ctcggccctt ccggctggct ggtttattgc    780

tgataaatct ggagccggtg agcgtgggtc tcgcggtatc attgcagcac tggggccaga    840

tggtaagccc tcccgtatcg tagttatcta cacgacgggg agtcaggcaa ctatggatga    900

acgaaataga cagatcgctg agataggtgc ctcactgatt aagcattggt aactgtcaga    960

ccaagtttac tcatatatac tttagattga tttaaaactt catttttaat ttaaaaggat   1020

ctaggtgaag atcctttttg ataatctcat gaccaaaatc ccttaacgtg agttttcgtt   1080

ccactgagcg tcagaccccg tagaaaagat caaaggatct tcttgagatc cttttttct   1140

gcgcgtaatc tgctgcttgc aaacaaaaaa accaccgcta ccagcggtgg tttgtttgcc   1200
```

-continued

```
ggatcaagag ctaccaactc tttttccgaa ggtaactggc ttcagcagag cgcagatacc   1260
aaatactgtc cttctagtgt agccgtagtt aggccaccac ttcaagaact ctgtagcacc   1320
gcctacatac ctcgctctgc taatcctgtt accagtggct gctgccagtg gcgataagtc   1380
gtgtcttacc gggttggact caagacgata gttaccggat aaggcgcagc ggtcgggctg   1440
aacggggggt tcgtgcacac agcccagctt ggagcgaacg acctacaccg aactgagata   1500
cctacagcgt gagcattgag aaagcgccac gcttcccgaa gggagaaagg cggacaggta   1560
tccggtaagc ggcagggtcg gaacaggaga gcgcacgagg gagcttccag ggggaaacgc   1620
ctggtatctt tatagtcctg tcgggtttcg ccacctctga cttgagcgtc gatttttgtg   1680
atgctcgtca ggggggcgga gcctatggaa aaacgccagc aacgcggcct ttttacggtt   1740
cctggccttt tgctggcctt ttgctcacat gttctttcct gcgttatccc ctgattctgt   1800
ggataaccgt attaccgcct ttgagtgagc tgataccgct cgccgcagcc gaacgaccga   1860
gcgcagcgag tcagtgagcg aggaagcgga agagcgcctg atgcggtatt ttctccttac   1920
gcatctgtgc ggtatttcac accgcatata tggtgcactc tcagtacaat ctgctctgat   1980
gccgcatagt taagccagta tacactccgc tatcgctacg tgactgggtc atggctgcgc   2040
cccgacaccc gccaacaccc gctgacgcgc cctgacgggc ttgtctgctc ccggcatccg   2100
cttacagaca agctgtgacc gtctccggga gctgcatgtg tcagaggttt tcaccgtcat   2160
caccgaaacg cgcgaggcag ctgcggtaaa gctcatcagc gtggtcgtga agcgattcac   2220
agatgtctgc ctgttcatcc gcgtccagct cgttgagttt ctccagaagc gttaatgtct   2280
ggcttctgat aaagcgggcc atgttaaggg cggttttttc ctgtttggtc acttgatgcc   2340
tccgtgtaag ggggaatttc tgttcatggg ggtaatgata ccgatgaaac gagagaggat   2400
gctcacgata cgggttactg atgatgaaca tgcccggtta ctggaacgtt gtgagggtaa   2460
acaactggcg gtatggatgc ggcgggacca gagaaaaatc actcagggtc aatgccagcg   2520
cttcgttaat acagatgtag gtgttccaca gggtagccag cagcatcctg cgatgcagat   2580
ccggaacata atggtgcagg gcgctgactt ccgcgtttcc agactttacg aaacacggaa   2640
accgaagacc attcatgttg ttgctcaggt cgcagacgtt ttgcagcagc agtcgcttca   2700
cgttcgctcg cgtatcggtg attcattctg ctaaccagta aggcaacccc gccagcctag   2760
ccgggtcctc aacgacagga gcacgatcat gcgcacccgt ggccaggacc caacgctgcc   2820
cgagatgcgc cgcgtgcggc tgctggagat ggcggacgcg atggatatgt tctgccaagg   2880
gttggtttgc gcattcacag ttctccgcaa gaattgattg gctccaattc ttggagtggt   2940
gaatccgtta gcgaggtgcc gccggcttcc attcaggtcg aggtggcccg gctccatgca   3000
ccgcgacgca acgcggggag gcagacaagg tatagggcgg cgcctacaat ccatgccaac   3060
ccgttccatg tgctcgccga ggcggcataa atcgccgtga cgatcagcgg tccagtgatc   3120
gaagttaggc tggtaagagc cgcgagcgat ccttgaagct gtccctgatg gtcgtcatct   3180
acctgcctgg acagcatggc ctgcaacgcg ggcatcccga tgccgccgga agcgagaaga   3240
atcataatgg ggaaggccat ccagcctcgc gtcgcgaacg ccagcaagac gtagcccagc   3300
gcgtcggcca gcttgcaatt cgcgctaact tacattaatt gcgttgcgct cactgcccgc   3360
tttccagtcg ggaaacctgt cgtgccagct gcattaatga atcggccaac gcgcggggag   3420
aggcggtttg cgtattgggc gccagggtgg tttttctttt caccagtgag acgggcaaca   3480
gctgattgcc cttcaccgcc tggccctgag agagttgcag caagcggtcc acgctggttt   3540
```

gccccagcag gcgaaaatcc tgtttgatgg tggttgacgg cgggatataa catgagctgt 3600
cttcggtatc gtcgtatccc actaccgaga tatccgcacc aacgcgcagc ccggactcgg 3660
taatggcgcg cattgcgccc agcgccatct gatcgttggc aaccagcatc gcagtgggaa 3720
cgatgccctc attcagcatt tgcatggttt gttgaaaacc ggacatggca ctccagtcgc 3780
cttcccgttc cgctatcggc tgaatttgat tgcgagtgag atatttatgc cagccagcca 3840
gacgcagacg cgccgagaca gaacttaatg gtcccgctaa cagcgcgatt tgctgatgac 3900
ccaatgcgac cagatgctcc acgcccagtc gcgtaccgtc ttcatgggag aaaataatac 3960
tgttgatggg tgtctggtca gagacatcaa gaaataacgc cggaacatta gtgcaggcag 4020
cttccacagc aatggcatcc tggtcatcca gcggatagtt aatgatcagc ccactgacgc 4080
gttgcgcgag aagattgtgc accgccgctt tacaggcttc gacgccgctt cgttctacca 4140
tcgacaccac cacgctggca cccagttgat cggcgcgaga tttaatcgcc gcgacaattt 4200
gcgacggcgc gtgcagggcc agactggagg tggcaacgcc aatcagcaac gactgtttgc 4260
ccgccagttg ttgtgccacg cggttgggaa tgtaattcag ctccgccatc gccgcttcca 4320
ctttttcccg cgttttcgca gaaacgtggc tggcctggtt caccacgcgg gaaacggtct 4380
gataagagac accggcatac tctgcgacat cgtataacgt tactggtttc acattcacca 4440
ccctgaattg actctcttcc gggcgctatc atgccatacc gcgaaaggtt ttgcgccatt 4500
cgatggtgtc aacgtaaatg catgccgctt cgccttcgcg cgcgaattgc aagctgatcc 4560
ggagcttatc gactgcacgg tgcaccaatg cttctggcgt caggcagcca tcggaagctg 4620
tggtatggct gtgcaggtcg taaatcactg cataattcgt gtcgctcaag gcgcactccc 4680
gttctggata atgtttttg cgccgacatc ataacggttc tggcaaatat tctgaaatga 4740
gctgttgaca attaatcatc ggctcgtata atgtgtggaa ttgtgagcgg ataacaattt 4800
cacacaggaa acagaattcc atatgaaata cctattacca acagcagcag ctgggttatt 4860
attgctcgct gcgcagccgg ccatggccca ggtcaccgtc tcctcacgta cggtggctgc 4920
accatctgtc ttcatcttcc cgccatctga tgagcagttg aaatctggaa ctgcctctgt 4980
tgtgtgcctg ctgaataact tctatcccag agaggccaaa gtacagtgga aggtggataa 5040
cgccctccaa tcgggtaact cccaggagag tgtcacagag caggacagca aggacagcac 5100
ctacagcctc agcagcaccc tgacgctgag caaagcagac tacgagaaac acaaagtcta 5160
cgcctgcgaa gtcacccatc agggcctgag ctcgccggtg acaaagagct tcaaccgcgg 5220
agagtgtgca ggtgattaca aagacgatga cgataagtaa taaacaggaa acagaagtcc 5280
atatgaaata cctattgcct acggcagccg ctggattgtt attactcgcg gcccagccgg 5340
ccatggccgc tagcaccaag ggcccatcgg tcttccccct ggcaccctcc tccaagagca 5400
cctctggggg cacagcggcc ctgggctgcc tggtcaagga ctacttcccc gaaccggtga 5460
cggtgtcgtg gaactcaggc gccctgacca gcggcgtgca caccttcccg gctgtcctac 5520
agtcctcagg actctactcc ctcagcagcg tagtgaccgt gccctccagc agcttgggca 5580
cccagaccta catctgcaac gtgaatcaca agcccagcaa caccaaggtg gacaagaaag 5640
ttgagcccaa atcttgtgac aaaactgagg tgcagctggt ggagtctggg ggaggcttcg 5700
tgcaggcggg ggaatctctg acgctctcct gtacaagttc tacactgacc ttcactccgt 5760
atcgcatggc ctggtaccgc caggctccag ggaagcagcg tgatttagtc gcggatatta 5820
gtagtggtga tggtaggacc acaaactatg cggacttcgc gaagggccga ttcaccatct 5880
ccagagacaa catcaagaac acggtctttc tgcgaatgac taacctgaaa cctgaggaca 5940

```
cggccgtcta ctactgtaac accttcgttt cgtttgtggg gattgcgcgt tcttggggcc   6000

aggggaccca ggtcactgtc tcctcagcgg ccgcagaaca aaaactcatc tcagaagagg   6060

atctgaatgg ggccgtacat caccaccatc atcatgggag ctaagcttct gttttggcgg   6120

atgagagaag attttcagcc tgatacagat taaatcagaa cgcagaagcg gtctgataaa   6180

acagaatttg cctggcggca gtagcgcggt ggtcccacct gaccccatgc cgaactcaga   6240

agtgaaacgc cgtagcgccg atggtagtgt ggggtctccc catgcgagag tagggaactg   6300

ccaggcatca aataaaacga aaggctcagt cgaaagactg ggcctttcgt tttatctgtt   6360

gtttgtcggt gaacgctctc ctgagtagga caaatccgcc gggagcggat ttgaacgttg   6420

cgaagcaacg gcccggagga ccctggcggg caggacgccc gccataaact gccaggcatc   6480

aaattaagca gaaggccatc ctgacggatg gcctttttgc gtttctacaa actctt       6536
```

<210> SEQ ID NO 17
<211> LENGTH: 7246
<212> TYPE: DNA
<213> ORGANISM: Artificial
<220> FEATURE:
<223> OTHER INFORMATION: Synthetic plasmid p1214

<400> SEQUENCE: 17

```
cctgaattga ctctcttccg ggcgctatca tgccataccg cgaaaggttt tgcgccattc     60

gatggtgtca acgtaaatgc atgccgcttc gccttcgcgc gcgaattgca agctgatccg    120

gagcttatcg actgcacggt gcaccaatgc ttctggcgtc aggcagccat cggaagctgt    180

ggtatggctg tgcaggtcgt aaatcactgc ataattcgtg tcgctcaagg cgcactcccg    240

ttctggataa tgtttttttgc gccgacatca taacggttct ggcaaatatt ctgaaatgag   300

ctgttgacaa ttaatcatcg gctcgtataa tgtgtggaat tgtgagcgga taacaatttc    360

acacaggaaa cagaattcca tatgaaatac ctattaccaa cagcagcagc tgggttatta    420

ttgctcgctg cgcagccggc catggccgag gtgcagctgg tggagtctgg gggaggcttc    480

gtgcaggcgg gggaatctct gacgctctcc tgtacaagtt ctacactgac cttcactccg    540

tatcgcatgg cctggtaccg ccaggctcca gggaagcagc gtgatttagt cgcggatatt    600

agtagtggtg atggtaggac cacaaactat gcggacttcg cgaagggccg attcaccatc    660

tccagagaca acatcaagaa cacggtcttt ctgcgaatga ctaacctgaa acctgaggac    720

acggccgtct actactgtaa caccttcgtt tcgtttgtgg ggattgcgcg ttcttggggc    780

caggggaccc aggtcaccgt ctcctcacgt acggtggctg caccatctgt cttcatcttc    840

ccgccatctg atgagcagtt gaaatctgga actgcctctg ttgtgtgcct gctgaataac    900

ttctatccca gagaggccaa agtacagtgg aaggtggata acgccctcca atcgggtaac    960

tcccaggaga gtgtcacaga gcaggacagc aaggacagca cctacagcct cagcagcacc   1020

ctgacgctga gcaaagcaga ctacgagaaa cacaaagtct acgcctgcga agtcacccat   1080

cagggcctga gctcgcccgt gacaaagagc ttcaaccgcg gagagtgtgc aggtgattac   1140

aaagacgatg acgataagta ataaacagga aacagaagtc catatgaaat acctattgcc   1200

tacggcagcc gctggattgt tattactcgc ggcccagccg gccatggccg aggtgcagct   1260

ggtggagtct gggggagagt tggtgcaggc tgggggctct ctgagactct cctgtgcagc   1320

ctctggcctc accttcagta gctataacat gggctggttc cgccgggctc cagggaagga   1380

gcgtgagttt gtagcatcta ttacctggag tggtcgggac acattctatg cagactccgt   1440
```

-continued

```
gaagggccga ttcaccatct ccagagacaa cgccaagaac actgtttatc tgcaaatgag   1500
cagcctgaaa cctgaggaca cggccgttta ttattgtgct gcaaacccct ggccagtggc   1560
ggcgccacgt agtggcacct actggggcca agggacccag gtcaccgtct cctcagctag   1620
caccaagggc ccatcggtct tcccccctggc accctcctcc aagagcacct ctgggggcac   1680
agcggccctg ggctgcctgg tcaaggacta cttccccgaa ccggtgacgg tgtcgtggaa   1740
ctcaggcgcc ctgaccagcg gcgtgcacac cttcccggct gtcctacagt cctcaggact   1800
ctactccctc agcagcgtag tgaccgtgcc ctccagcagc ttgggcaccc agacctacat   1860
ctgcaacgtg aatcacaagc ccagcaacac caaggtggac aagaaagttg agcccaaatc   1920
ttgtgacaaa actgaggtgc agctggtgga gtctggggga ggcttcgtgc aggcggggga   1980
atctctgacg ctctcctgta caagttctac actgaccttc actccgtatc gcatggcctg   2040
gtaccgccag gctccaggga agcagcgtga tttagtcgcg gatattagta gtggtgatgg   2100
taggaccaca aactatgcgg acttcgcgaa gggccgattc accatctcca gagacaacat   2160
caagaacacg gtctttctgc gaatgactaa cctgaaacct gaggacacgg ccgtctacta   2220
ctgtaacacc ttcgtttcgt ttgtggggat tgcgcgttct tggggccagg ggacccaggt   2280
cactgtctcc tcagcggccg cagaacaaaa actcatctca gaagaggatc tgaatggggc   2340
cgtacatcac caccatcatc atgggagcta agcttggctg ttttggcgga tgagagaaga   2400
ttttcagcct gatacagatt aaatcagaac gcagaagcgg tctgataaaa cagaatttgc   2460
ctggcggcag tagcgcggtg gtcccacctg accccatgcc gaactcagaa gtgaaacgcc   2520
gtagcgccga tggtagtgtg gggtctcccc atgcgagagt agggaactgc caggcatcaa   2580
ataaaacgaa aggctcagtc gaaagactgg gcctttcgtt ttatctgttg tttgtcggtg   2640
aacgctctcc tgagtaggac aaatccgccg ggagcggatt tgaacgttgc gaagcaacgg   2700
cccggaggac cctggcgggc aggacgcccg ccataaactg ccaggcatca aattaagcag   2760
aaggccatcc tgacggatgg cctttttgcg tttctacaaa ctcttttgtt tatttttcta   2820
aatacattca aatatgtatc cgctcatgag acaataaccc tgataaatgc ttcaataata   2880
ttgaaaaagg aagagtatga gtattcaaca tttccgtgtc gcccttattc cctttttttgc   2940
ggcattttgc cttcctgttt ttgctcaccc agaaacgctg gtgaaagtaa aagatgctga   3000
agatcagttg ggtgcacgag tgggttacat cgaactggat ctcaacagcg gtaagatcct   3060
tgagagtttt cgccccgaag aacgttttcc aatgatgagc acttttaaag ttctgctatg   3120
tggcgcggta ttatcccgtg ttgacgccgg gcaagagcaa ctcggtcgcc gcatacacta   3180
ttctcagaat gacttggttg agtactcacc agtcacagaa aagcatctta cggatggcat   3240
gacagtaaga gaattatgca gtgctgccat aaccatgagt gataacactg cggccaactt   3300
acttctgaca acgatcggag gaccgaagga gctaaccgct tttttgcaca acatggggga   3360
tcatgtaact cgccttgatc gttgggaacc ggagctgaat gaagccatac caaacgacga   3420
gcgtgacacc acgatgcctg tagcaatggc aacaacgttg cgcaaactat taactggcga   3480
actacttact ctagcttccc ggcaacaatt aatagactgg atggaggcgg ataaagttgc   3540
aggaccactt ctgcgctcgg cccttccggc tggctggttt attgctgata aatctggagc   3600
cggtgagcgt gggtctcgcg gtatcattgc agcactgggg ccagatggta agccctcccg   3660
tatcgtagtt atctacacga cggggagtca ggcaactatg gatgaacgaa atagacagat   3720
cgctgagata ggtgcctcac tgattaagca ttggtaactg tcagaccaag tttactcata   3780
tatactttag attgatttaa aacttcattt ttaatttaaa aggatctagg tgaagatcct   3840
```

-continued

```
ttttgataat ctcatgacca aaatccctta acgtgagttt tcgttccact gagcgtcaga   3900
ccccgtagaa aagatcaaag gatcttcttg agatcctttt tttctgcgcg taatctgctg   3960
cttgcaaaca aaaaaaccac cgctaccagc ggtggtttgt ttgccggatc aagagctacc   4020
aactcttttt ccgaaggtaa ctggcttcag cagagcgcag ataccaaata ctgtccttct   4080
agtgtagccg tagttaggcc accacttcaa gaactctgta gcaccgccta catacctcgc   4140
tctgctaatc ctgttaccag tggctgctgc cagtggcgat aagtcgtgtc ttaccgggtt   4200
ggactcaaga cgatagttac cggataaggc gcagcggtcg ggctgaacgg ggggttcgtg   4260
cacacagccc agcttggagc gaacgaccta caccgaactg agatacctac agcgtgagca   4320
ttgagaaagc gccacgcttc ccgaagggag aaaggcggac aggtatccgg taagcggcag   4380
ggtcggaaca ggagagcgca cgagggagct tccaggggga aacgcctggt atctttatag   4440
tcctgtcggg tttcgccacc tctgacttga gcgtcgattt ttgtgatgct cgtcaggggg   4500
gcggagccta tggaaaaacg ccagcaacgc ggccttttta cggttcctgg ccttttgctg   4560
gccttttgct cacatgttct ttcctgcgtt atcccctgat tctgtggata accgtattac   4620
cgcctttgag tgagctgata ccgctcgccg cagccgaacg accgagcgca gcgagtcagt   4680
gagcgaggaa gcggaagagc gcctgatgcg gtattttctc cttacgcatc tgtgcggtat   4740
ttcacaccgc atatatggtg cactctcagt acaatctgct ctgatgccgc atagttaagc   4800
cagtatacac tccgctatcg ctacgtgact gggtcatggc tgcgccccga cacccgccaa   4860
cacccgctga cgcgccctga cgggcttgtc tgctcccggc atccgcttac agacaagctg   4920
tgaccgtctc cgggagctgc atgtgtcaga ggttttcacc gtcatcaccg aaacgcgcga   4980
ggcagctgcg gtaaagctca tcagcgtggt cgtgaagcga ttcacagatg tctgcctgtt   5040
catccgcgtc cagctcgttg agtttctcca gaagcgttaa tgtctggctt ctgataaagc   5100
gggccatgtt aagggcggtt ttttcctgtt tggtcacttg atgcctccgt gtaaggggga   5160
atttctgttc atgggggtaa tgataccgat gaaacgagag aggatgctca cgatacgggt   5220
tactgatgat gaacatgccc ggttactgga acgttgtgag ggtaaacaac tggcggtatg   5280
gatgcggcgg gaccagagaa aaatcactca gggtcaatgc cagcgcttcg ttaatacaga   5340
tgtaggtgtt ccacagggta gccagcagca tcctgcgatg cagatccgga acataatggt   5400
gcagggcgct gacttccgcg tttccagact ttacgaaaca cggaaaccga agaccattca   5460
tgttgttgct caggtcgcag acgttttgca gcagcagtcg cttcacgttc gctcgcgtat   5520
cggtgattca ttctgctaac cagtaaggca accccgccag cctagccggg tcctcaacga   5580
caggagcacg atcatgcgca cccgtggcca ggacccaacg ctgcccgaga tgcgccgcgt   5640
gcggctgctg gagatggcgg acgcgatgga tatgttctgc caagggttgg tttgcgcatt   5700
cacagttctc cgcaagaatt gattggctcc aattcttgga gtggtgaatc cgttagcgag   5760
gtgccgccgg cttccattca ggtcgaggtg gcccggctcc atgcaccgcg acgcaacgcg   5820
gggaggcaga caaggtatag ggcggcgcct acaatccatg ccaacccgtt ccatgtgctc   5880
gccgaggcgg cataaatcgc cgtgacgatc agcggtccag tgatcgaagt taggctggta   5940
agagccgcga gcgatccttg aagctgtccc tgatggtcgt catctacctg cctggacagc   6000
atggcctgca acgcgggcat cccgatgccg ccggaagcga gaagaatcat aatggggaag   6060
gccatccagc ctcgcgtcgc gaacgccagc aagacgtagc ccagcgcgtc ggccagcttg   6120
caattcgcgc taacttacat taattgcgtt gcgctcactg cccgctttcc agtcgggaaa   6180
```

cctgtcgtgc cagctgcatt aatgaatcgg ccaacgcgcg gggagaggcg gtttgcgtat 6240
tgggcgccag ggtggttttt cttttcacca gtgagacggg caacagctga ttgcccttca 6300
ccgcctggcc ctgagagagt tgcagcaagc ggtccacgct ggtttgcccc agcaggcgaa 6360
aatcctgttt gatggtggtt gacggcggga tataacatga gctgtcttcg gtatcgtcgt 6420
atcccactac cgagatatcc gcaccaacgc gcagcccgga ctcggtaatg gcgcgcattg 6480
cgcccagcgc catctgatcg ttggcaacca gcatcgcagt gggaacgatg ccctcattca 6540
gcatttgcat ggtttgttga aaaccggaca tggcactcca gtcgccttcc cgttccgcta 6600
tcggctgaat ttgattgcga gtgagatatt tatgccagcc agccagacgc agacgcgccg 6660
agacagaact taatggtccc gctaacagcg cgatttgctg atgacccaat gcgaccagat 6720
gctccacgcc cagtcgcgta ccgtcttcat gggagaaaat aatactgttg atgggtgtct 6780
ggtcagagac atcaagaaat aacgccggaa cattagtgca ggcagcttcc acagcaatgg 6840
catcctggtc atccagcgga tagttaatga tcagcccact gacgcgttgc gcgagaagat 6900
tgtgcaccgc cgctttacag gcttcgacgc cgcttcgttc taccatcgac accaccacgc 6960
tggcacccag ttgatcggcg cgagatttaa tcgccgcgac aatttgcgac ggcgcgtgca 7020
gggccagact ggaggtggca acgccaatca gcaacgactg tttgcccgcc agttgttgtg 7080
ccacgcggtt gggaatgtaa ttcagctccg ccatcgccgc ttccactttt tcccgcgttt 7140
tcgcagaaac gtggctggcc tggttcacca cgcgggaaac ggtctgataa gagacaccgg 7200
catactctgc gacatcgtat aacgttactg gtttcacatt caccac 7246

<210> SEQ ID NO 18
<211> LENGTH: 7237
<212> TYPE: DNA
<213> ORGANISM: Artificial
<220> FEATURE:
<223> OTHER INFORMATION: Synthetic plasmid p1215

<400> SEQUENCE: 18
cctgaattga ctctcttccg ggcgctatca tgccataccg cgaaaggttt tgcgccattc 60
gatggtgtca acgtaaatgc atgccgcttc gccttcgcgc gcgaattgca agctgatccg 120
gagcttatcg actgcacggt gcaccaatgc ttctggcgtc aggcagccat cggaagctgt 180
ggtatggctg tgcaggtcgt aaatcactgc ataattcgtg tcgctcaagg cgcactcccg 240
ttctggataa tgttttttgc gccgacatca taacggttct ggcaaatatt ctgaaatgag 300
ctgttgacaa ttaatcatcg gctcgtataa tgtgtggaat tgtgagcgga taacaatttc 360
acacaggaaa cagaattcca tatgaaatac ctattaccaa cagcagcagc tgggttatta 420
ttgctcgctg cgcagccggc catggccgag gtgcagctgg tggagtctgg gggaggcttc 480
gtgcaggcgg gggaatctct gacgctctcc tgtacaagtt ctacactgac cttcactccg 540
tatcgcatgg cctggtaccg ccaggctcca gggaagcagc gtgatttagt cgcggatatt 600
agtagtggtg atggtaggac cacaaactat gcggacttcg cgaagggccg attcaccatc 660
tccagagaca acatcaagaa cacggtcttt ctgcgaatga ctaacctgaa acctgaggac 720
acggccgtct actactgtaa caccttcgtt tcgtttgtgg ggattgcgcg ttcttggggc 780
caggggaccc aggtcaccgt ctcctcacgt acggtggctg caccatctgt cttcatcttc 840
ccgccatctg atgagcagtt gaaatctgga actgcctctg ttgtgtgcct gctgaataac 900
ttctatccca gagaggccaa agtacagtgg aaggtggata acgccctcca atcgggtaac 960
tcccaggaga gtgtcacaga gcaggacagc aaggacagca cctacagcct cagcagcacc 1020

-continued ctgacgctga gcaaagcaga ctacgagaaa cacaaagtct acgcctgcga agtcacccat 1080
cagggcctga gctcgccggt gacaaagagc ttcaaccgcg gagagtgtgc aggtgattac 1140
aaagacgatg acgataagta ataaacagga aacagaagtc catatgaaat acctattgcc 1200
tacggcagcc gctggattgt tattactcgc ggcccagccg gccatggccg aggtgcagct 1260
ggtggagtct gggggaggct tagtgcagcc tggggagtct ctgacactct cctgtgtagt 1320
tgctggaagc atcttcagct tcgccatgag ctggtatcgc caggctccag gaaaagagcg 1380
cgaattggtc gcacgtattg gttcggatga tcgggtaacg tacgcagatt ccgtgaaggg 1440
ccgatttacc atctccagag acaacatcaa gcgcacggcg ggcctgcaga tgaacagcct 1500
gaaacctgag gacacggccg tctactactg caatgcccaa acagatttga gggattggac 1560
tgtgcgagag tactggggcc aggggaccca ggtcaccgtc tcctcagcta gcaccaaggg 1620
cccatcggtc ttccccctgg caccctcctc caagagcacc tctgggggca cagcggccct 1680
gggctgcctg gtcaaggact acttccccga accggtgacg gtgtcgtgga actcaggcgc 1740
cctgaccagc ggcgtgcaca ccttcccggc tgtcctacag tcctcaggac tctactccct 1800
cagcagcgta gtgaccgtgc cctccagcag cttgggcacc cagacctaca tctgcaacgt 1860
gaatcacaag cccagcaaca ccaaggtgga caagaaagtt gagcccaaat cttgtgacaa 1920
aactgaggtg cagctggtgg agtctggggg aggcttcgtg caggcggggg aatctctgac 1980
gctctcctgt acaagttcta cactgacctt cactccgtat cgcatggcct ggtaccgcca 2040
ggctccaggg aagcagcgtg atttagtcgc ggatattagt agtggtgatg gtaggaccac 2100
aaactatgcg gacttcgcga agggccgatt caccatctcc agagacaaca tcaagaacac 2160
ggtctttctg cgaatgacta acctgaaacc tgaggacacg gccgtctact actgtaacac 2220
cttcgtttcg tttgtgggga ttgcgcgttc ttggggccag gggacccagg tcactgtctc 2280
ctcagcggcc gcagaacaaa aactcatctc agaagaggat ctgaatgggg ccgtacatca 2340
ccaccatcat catgggagct aagcttggct gttttggcgg atgagagaag attttcagcc 2400
tgatacagat taaatcagaa cgcagaagcg gtctgataaa acagaatttg cctggcggca 2460
gtagcgcggt ggtcccacct gaccccatgc cgaactcaga agtgaaacgc cgtagcgccg 2520
atggtagtgt ggggtctccc catgcgagag tagggaactg ccaggcatca aataaaacga 2580
aaggctcagt cgaaagactg ggcctttcgt tttatctgtt gtttgtcggt gaacgctctc 2640
ctgagtagga caaatccgcc gggagcggat ttgaacgttg cgaagcaacg gcccggagga 2700
ccctggcggg caggacgccc gccataaact gccaggcatc aaattaagca gaaggccatc 2760
ctgacggatg gcctttttgc gtttctacaa actcttttgt ttatttttct aaatacattc 2820
aaatatgtat ccgctcatga gacaataacc ctgataaatg cttcaataat attgaaaaag 2880
gaagagtatg agtattcaac atttccgtgt cgcccttatt cccttttttg cggcattttg 2940
ccttcctgtt tttgctcacc cagaaacgct ggtgaaagta aaagatgctg aagatcagtt 3000
gggtgcacga gtgggttaca tcgaactgga tctcaacagc ggtaagatcc ttgagagttt 3060
tcgccccgaa gaacgttttc caatgatgag cacttttaaa gttctgctat gtggcgcggt 3120
attatcccgt gttgacgccg ggcaagagca actcggtcgc cgcatacact attctcagaa 3180
tgacttggtt gagtactcac cagtcacaga aaagcatctt acggatggca tgacagtaag 3240
agaattatgc agtgctgcca taaccatgag tgataacact gcggccaact tacttctgac 3300
aacgatcgga ggaccgaagg agctaaccgc ttttttgcac aacatggggg atcatgtaac 3360

-continued

```
tcgccttgat cgttgggaac cggagctgaa tgaagccata ccaaacgacg agcgtgacac   3420
cacgatgcct gtagcaatgg caacaacgtt gcgcaaacta ttaactggcg aactacttac   3480
tctagcttcc cggcaacaat taatagactg gatggaggcg gataaagttg caggaccact   3540
tctgcgctcg gcccttccgg ctggctggtt tattgctgat aaatctggag ccggtgagcg   3600
tgggtctcgc ggtatcattg cagcactggg gccagatggt aagccctccc gtatcgtagt   3660
tatctacacg acggggagtc aggcaactat ggatgaacga aatagacaga tcgctgagat   3720
aggtgcctca ctgattaagc attggtaact gtcagaccaa gtttactcat atatacttta   3780
gattgattta aaacttcatt tttaatttaa aaggatctag gtgaagatcc tttttgataa   3840
tctcatgacc aaaatccctt aacgtgagtt ttcgttccac tgagcgtcag accccgtaga   3900
aaagatcaaa ggatcttctt gagatccttt ttttctgcgc gtaatctgct gcttgcaaac   3960
aaaaaaacca ccgctaccag cggtggtttg tttgccggat caagagctac caactctttt   4020
tccgaaggta actggcttca gcagagcgca gataccaaat actgtccttc tagtgtagcc   4080
gtagttaggc caccacttca agaactctgt agcaccgcct acatacctcg ctctgctaat   4140
cctgttacca gtggctgctg ccagtggcga taagtcgtgt cttaccgggt tggactcaag   4200
acgatagtta ccggataagg cgcagcggtc gggctgaacg gggggttcgt gcacacagcc   4260
cagcttggag cgaacgacct acaccgaact gagataccta cagcgtgagc attgagaaag   4320
cgccacgctt cccgaaggga gaaaggcgga caggtatccg gtaagcggca gggtcggaac   4380
aggagagcgc acgagggagc ttccaggggg aaacgcctgg tatctttata gtcctgtcgg   4440
gtttcgccac ctctgacttg agcgtcgatt tttgtgatgc tcgtcagggg ggcggagcct   4500
atggaaaaac gccagcaacg cggccttttt acggttcctg gccttttgct ggccttttgc   4560
tcacatgttc tttcctgcgt tatcccctga ttctgtggat aaccgtatta ccgcctttga   4620
gtgagctgat accgctcgcc gcagccgaac gaccgagcgc agcgagtcag tgagcgagga   4680
agcggaagag cgcctgatgc ggtattttct ccttacgcat ctgtgcggta tttcacaccg   4740
catatatggt gcactctcag tacaatctgc tctgatgccg catagttaag ccagtataca   4800
ctccgctatc gctacgtgac tgggtcatgg ctgcgccccg acacccgcca acacccgctg   4860
acgcgccctg acgggcttgt ctgctcccgg catccgctta cagacaagct gtgaccgtct   4920
ccgggagctg catgtgtcag aggttttcac cgtcatcacc gaaacgcgcg aggcagctgc   4980
ggtaaagctc atcagcgtgg tcgtgaagcg attcacagat gtctgcctgt tcatccgcgt   5040
ccagctcgtt gagtttctcc agaagcgtta atgtctggct tctgataaag cgggccatgt   5100
taagggcggt tttttcctgt ttggtcactt gatgcctccg tgtaaggggg aatttctgtt   5160
catgggggta atgataccga tgaaacgaga gaggatgctc acgatacggg ttactgatga   5220
tgaacatgcc cggttactgg aacgttgtga gggtaaacaa ctggcggtat ggatgcggcg   5280
ggaccagaga aaaatcactc agggtcaatg ccagcgcttc gttaatacag atgtaggtgt   5340
tccacagggt agccagcagc atcctgcgat gcagatccgg aacataatgg tgcagggcgc   5400
tgacttccgc gtttccagac tttacgaaac acggaaaccg aagaccattc atgttgttgc   5460
tcaggtcgca gacgttttgc agcagcagtc gcttcacgtt cgctcgcgta tcggtgattc   5520
attctgctaa ccagtaaggc aaccccgcca gcctagccgg gtcctcaacg acaggagcac   5580
gatcatgcgc acccgtggcc aggacccaac gctgcccgag atgcgccgcg tgcggctgct   5640
ggagatggcg gacgcgatgg atatgttctg ccaagggttg gtttgcgcat tcacagttct   5700
ccgcaagaat tgattggctc caattcttgg agtggtgaat ccgttagcga ggtgccgccg   5760
```

```
gcttccattc aggtcgaggt ggcccggctc catgcaccgc gacgcaacgc ggggaggcag   5820

acaaggtata gggcggcgcc tacaatccat gccaacccgt tccatgtgct cgccgaggcg   5880

gcataaatcg ccgtgacgat cagcggtcca gtgatcgaag ttaggctggt aagagccgcg   5940

agcgatcctt gaagctgtcc ctgatggtcg tcatctacct gcctggacag catggcctgc   6000

aacgcgggca tcccgatgcc gccggaagcg agaagaatca taatggggaa ggccatccag   6060

cctcgcgtcg cgaacgccag caagacgtag cccagcgcgt cggccagctt gcaattcgcg   6120

ctaacttaca ttaattgcgt tgcgctcact gcccgctttc cagtcgggaa acctgtcgtg   6180

ccagctgcat taatgaatcg gccaacgcgc ggggagaggc ggtttgcgta ttgggcgcca   6240

gggtggtttt tcttttcacc agtgagacgg gcaacagctg attgcccttc accgcctggc   6300

cctgagagag ttgcagcaag cggtccacgc tggtttgccc cagcaggcga aaatcctgtt   6360

tgatggtggt tgacggcggg atataacatg agctgtcttc ggtatcgtcg tatcccacta   6420

ccgagatatc cgcaccaacg cgcagcccgg actcggtaat ggcgcgcatt gcgcccagcg   6480

ccatctgatc gttggcaacc agcatcgcag tgggaacgat gccctcattc agcatttgca   6540

tggtttgttg aaaaccggac atggcactcc agtcgccttc ccgttccgct atcggctgaa   6600

tttgattgcg agtgagatat ttatgccagc cagccagacg cagacgcgcc gagacagaac   6660

ttaatggtcc cgctaacagc gcgatttgct gatgacccaa tgcgaccaga tgctccacgc   6720

ccagtcgcgt accgtcttca tgggagaaaa taatactgtt gatgggtgtc tggtcagaga   6780

catcaagaaa taacgccgga acattagtgc aggcagcttc cacagcaatg gcatcctggt   6840

catccagcgg atagttaatg atcagcccac tgacgcgttg cgcgagaaga ttgtgcaccg   6900

ccgctttaca ggcttcgacg ccgcttcgtt ctaccatcga caccaccacg ctggcaccca   6960

gttgatcggc gcgagattta atcgccgcga caatttgcga cggcgcgtgc agggccagac   7020

tggaggtggc aacgccaatc agcaacgact gtttgcccgc cagttgttgt gccacgcggt   7080

tgggaatgta attcagctcc gccatcgccg cttccacttt ttcccgcgtt ttcgcagaaa   7140

cgtggctggc ctggttcacc acgcgggaaa cggtctgata agagacaccg gcatactctg   7200

cgacatcgta taacgttact ggtttcacat tcaccac                            7237
```

<210> SEQ ID NO 19
<211> LENGTH: 107
<212> TYPE: PRT
<213> ORGANISM: Artificial
<220> FEATURE:
<223> OTHER INFORMATION: Synthetic polypeptide 501-L

<400> SEQUENCE: 19

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95
```

```
Pro Val Thr Lys Ser Phe Asn Arg Gly Glu Cys
            100                 105


<210> SEQ ID NO 20
<211> LENGTH: 226
<212> TYPE: PRT
<213> ORGANISM: Artificial
<220> FEATURE:
<223> OTHER INFORMATION: Synthetic polypeptide 501-H

<400> SEQUENCE: 20

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Ala Ala Ala Glu Val Gln Leu Val Glu
            100                 105                 110

Ser Gly Gly Gly Phe Val Gln Ala Gly Glu Ser Leu Thr Leu Ser Cys
        115                 120                 125

Thr Ser Ser Thr Leu Thr Phe Thr Pro Tyr Arg Met Ala Trp Tyr Arg
    130                 135                 140

Gln Ala Pro Gly Lys Gln Arg Asp Leu Val Ala Asp Ile Ser Ser Gly
145                 150                 155                 160

Asp Gly Arg Thr Thr Asn Tyr Ala Asp Phe Ala Lys Gly Arg Phe Thr
                165                 170                 175

Ile Ser Arg Asp Asn Ile Lys Asn Thr Val Phe Leu Arg Met Thr Asn
            180                 185                 190

Leu Lys Pro Glu Asp Thr Ala Val Tyr Tyr Cys Asn Thr Phe Val Ser
        195                 200                 205

Phe Val Gly Ile Ala Arg Ser Trp Gly Gln Gly Thr Gln Val Thr Val
    210                 215                 220

Ser Ser
225


<210> SEQ ID NO 21
<211> LENGTH: 227
<212> TYPE: PRT
<213> ORGANISM: Artificial
<220> FEATURE:
<223> OTHER INFORMATION: Synthetic polypeptide 514-L

<400> SEQUENCE: 21

Glu Val Gln Leu Val Glu Ser Gly Gly Gly Phe Val Gln Ala Gly Glu
1               5                   10                  15

Ser Leu Thr Leu Ser Cys Thr Ser Ser Thr Leu Thr Phe Thr Pro Tyr
            20                  25                  30

Arg Met Ala Trp Tyr Arg Gln Ala Pro Gly Lys Gln Arg Asp Leu Val
        35                  40                  45

Ala Asp Ile Ser Ser Gly Asp Gly Arg Thr Thr Asn Tyr Ala Asp Phe
    50                  55                  60
```

Ala Lys Gly Arg Phe Thr Ile Ser Arg Asp Asn Ile Lys Asn Thr Val
65 70 75 80

Phe Leu Arg Met Thr Asn Leu Lys Pro Glu Asp Thr Ala Val Tyr Tyr
85 90 95

Cys Asn Thr Phe Val Ser Phe Val Gly Ile Ala Arg Ser Trp Gly Gln
100 105 110

Gly Thr Gln Val Thr Val Ser Ser Arg Thr Val Ala Ala Pro Ser Val
115 120 125

Phe Ile Phe Pro Pro Ser Asp Glu Gln Leu Lys Ser Gly Thr Ala Ser
130 135 140

Val Val Cys Leu Leu Asn Asn Phe Tyr Pro Arg Glu Ala Lys Val Gln
145 150 155 160

Trp Lys Val Asp Asn Ala Leu Gln Ser Gly Asn Ser Gln Glu Ser Val
165 170 175

Thr Glu Gln Asp Ser Lys Asp Ser Thr Tyr Ser Leu Ser Ser Thr Leu
180 185 190

Thr Leu Ser Lys Ala Asp Tyr Glu Lys His Lys Val Tyr Ala Cys Glu
195 200 205

Val Thr His Gln Gly Leu Ser Ser Pro Val Thr Lys Ser Phe Asn Arg
210 215 220

Gly Glu Cys
225

<210> SEQ ID NO 22
<211> LENGTH: 348
<212> TYPE: PRT
<213> ORGANISM: Artificial
<220> FEATURE:
<223> OTHER INFORMATION: Synthetic polypeptide 514-H

<400> SEQUENCE: 22

Glu Val Gln Leu Val Glu Ser Gly Gly Glu Leu Val Gln Ala Gly Gly
1 5 10 15

Ser Leu Arg Leu Ser Cys Ala Ala Ser Gly Leu Thr Phe Ser Ser Tyr
20 25 30

Asn Met Gly Trp Phe Arg Arg Ala Pro Gly Lys Glu Arg Glu Phe Val
35 40 45

Ala Ser Ile Thr Trp Ser Gly Arg Asp Thr Phe Tyr Ala Asp Ser Val
50 55 60

Lys Gly Arg Phe Thr Ile Ser Arg Asp Asn Ala Lys Asn Thr Val Tyr
65 70 75 80

Leu Gln Met Ser Ser Leu Lys Pro Glu Asp Thr Ala Val Tyr Tyr Cys
85 90 95

Ala Ala Asn Pro Trp Pro Val Ala Ala Pro Arg Ser Gly Thr Tyr Trp
100 105 110

Gly Gln Gly Thr Gln Val Thr Val Ser Ser Ala Ser Thr Lys Gly Pro
115 120 125

Ser Val Phe Pro Leu Ala Pro Ser Ser Lys Ser Thr Ser Gly Gly Thr
130 135 140

Ala Ala Leu Gly Cys Leu Val Lys Asp Tyr Phe Pro Glu Pro Val Thr
145 150 155 160

Val Ser Trp Asn Ser Gly Ala Leu Thr Ser Gly Val His Thr Phe Pro
165 170 175

Ala Val Leu Gln Ser Ser Gly Leu Tyr Ser Leu Ser Ser Val Val Thr
180 185 190

```
Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Ala Ala Ala Glu Val Gln Leu Val Glu Ser Gly Gly Gly Phe Val
225                 230                 235                 240

Gln Ala Gly Glu Ser Leu Thr Leu Ser Cys Thr Ser Ser Thr Leu Thr
                245                 250                 255

Phe Thr Pro Tyr Arg Met Ala Trp Tyr Arg Gln Ala Pro Gly Lys Gln
            260                 265                 270

Arg Asp Leu Val Ala Asp Ile Ser Ser Gly Asp Gly Arg Thr Thr Asn
        275                 280                 285

Tyr Ala Asp Phe Ala Lys Gly Arg Phe Thr Ile Ser Arg Asp Asn Ile
    290                 295                 300

Lys Asn Thr Val Phe Leu Arg Met Thr Asn Leu Lys Pro Glu Asp Thr
305                 310                 315                 320

Ala Val Tyr Tyr Cys Asn Thr Phe Val Ser Phe Val Gly Ile Ala Arg
                325                 330                 335

Ser Trp Gly Gln Gly Thr Gln Val Thr Val Ser Ser
            340                 345


<210> SEQ ID NO 23
<211> LENGTH: 227
<212> TYPE: PRT
<213> ORGANISM: Artificial
<220> FEATURE:
<223> OTHER INFORMATION: Synthetic polypeptide 515-L

<400> SEQUENCE: 23

Glu Val Gln Leu Val Glu Ser Gly Gly Gly Phe Val Gln Ala Gly Glu
1               5                   10                  15

Ser Leu Thr Leu Ser Cys Thr Ser Ser Thr Leu Thr Phe Thr Pro Tyr
            20                  25                  30

Arg Met Ala Trp Tyr Arg Gln Ala Pro Gly Lys Gln Arg Asp Leu Val
        35                  40                  45

Ala Asp Ile Ser Ser Gly Asp Gly Arg Thr Thr Asn Tyr Ala Asp Phe
    50                  55                  60

Ala Lys Gly Arg Phe Thr Ile Ser Arg Asp Asn Ile Lys Asn Thr Val
65                  70                  75                  80

Phe Leu Arg Met Thr Asn Leu Lys Pro Glu Asp Thr Ala Val Tyr Tyr
                85                  90                  95

Cys Asn Thr Phe Val Ser Phe Val Gly Ile Ala Arg Ser Trp Gly Gln
            100                 105                 110

Gly Thr Gln Val Thr Val Ser Ser Arg Thr Val Ala Ala Pro Ser Val
        115                 120                 125

Phe Ile Phe Pro Pro Ser Asp Glu Gln Leu Lys Ser Gly Thr Ala Ser
    130                 135                 140

Val Val Cys Leu Leu Asn Asn Phe Tyr Pro Arg Glu Ala Lys Val Gln
145                 150                 155                 160

Trp Lys Val Asp Asn Ala Leu Gln Ser Gly Asn Ser Gln Glu Ser Val
                165                 170                 175

Thr Glu Gln Asp Ser Lys Asp Ser Thr Tyr Ser Leu Ser Ser Thr Leu
            180                 185                 190

Thr Leu Ser Lys Ala Asp Tyr Glu Lys His Lys Val Tyr Ala Cys Glu
        195                 200                 205
```

```
Val Thr His Gln Gly Leu Ser Ser Pro Val Thr Lys Ser Phe Asn Arg
    210                 215                 220

Gly Glu Cys
225


<210> SEQ ID NO 24
<211> LENGTH: 345
<212> TYPE: PRT
<213> ORGANISM: Artificial
<220> FEATURE:
<223> OTHER INFORMATION: Synthetic polypeptide 515-H

<400> SEQUENCE: 24

Glu Val Gln Leu Val Glu Ser Gly Gly Gly Leu Val Gln Pro Gly Glu
1               5                   10                  15

Ser Leu Thr Leu Ser Cys Val Val Ala Gly Ser Ile Phe Ser Phe Ala
            20                  25                  30

Met Ser Trp Tyr Arg Gln Ala Pro Gly Lys Glu Arg Glu Leu Val Ala
        35                  40                  45

Arg Ile Gly Ser Asp Asp Arg Val Thr Tyr Ala Asp Ser Val Lys Gly
    50                  55                  60

Arg Phe Thr Ile Ser Arg Asp Asn Ile Lys Arg Thr Ala Gly Leu Gln
65                  70                  75                  80

Met Asn Ser Leu Lys Pro Glu Asp Thr Ala Val Tyr Tyr Cys Asn Ala
                85                  90                  95

Gln Thr Asp Leu Arg Asp Trp Thr Val Arg Glu Tyr Trp Gly Gln Gly
            100                 105                 110

Thr Gln Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Ala Ala
    210                 215                 220

Ala Glu Val Gln Leu Val Glu Ser Gly Gly Gly Phe Val Gln Ala Gly
225                 230                 235                 240

Glu Ser Leu Thr Leu Ser Cys Thr Ser Ser Thr Leu Thr Phe Thr Pro
                245                 250                 255

Tyr Arg Met Ala Trp Tyr Arg Gln Ala Pro Gly Lys Gln Arg Asp Leu
            260                 265                 270

Val Ala Asp Ile Ser Ser Gly Asp Gly Arg Thr Thr Asn Tyr Ala Asp
        275                 280                 285

Phe Ala Lys Gly Arg Phe Thr Ile Ser Arg Asp Asn Ile Lys Asn Thr
    290                 295                 300

Val Phe Leu Arg Met Thr Asn Leu Lys Pro Glu Asp Thr Ala Val Tyr
305                 310                 315                 320

Tyr Cys Asn Thr Phe Val Ser Phe Val Gly Ile Ala Arg Ser Trp Gly
                325                 330                 335
```

Gln Gly Thr Gln Val Thr Val Ser Ser
340 345

<210> SEQ ID NO 25
<211> LENGTH: 227
<212> TYPE: PRT
<213> ORGANISM: Artificial
<220> FEATURE:
<223> OTHER INFORMATION: Synthetic polypeptide 1214-L

<400> SEQUENCE: 25

Glu Val Gln Leu Val Glu Ser Gly Gly Gly Phe Val Gln Ala Gly Glu
1 5 10 15

Ser Leu Thr Leu Ser Cys Thr Ser Ser Thr Leu Thr Phe Thr Pro Tyr
20 25 30

Arg Met Ala Trp Tyr Arg Gln Ala Pro Gly Lys Gln Arg Asp Leu Val
35 40 45

Ala Asp Ile Ser Ser Gly Asp Gly Arg Thr Thr Asn Tyr Ala Asp Phe
50 55 60

Ala Lys Gly Arg Phe Thr Ile Ser Arg Asp Asn Ile Lys Asn Thr Val
65 70 75 80

Phe Leu Arg Met Thr Asn Leu Lys Pro Glu Asp Thr Ala Val Tyr Tyr
85 90 95

Cys Asn Thr Phe Val Ser Phe Val Gly Ile Ala Arg Ser Trp Gly Gln
100 105 110

Gly Thr Gln Val Thr Val Ser Ser Arg Thr Val Ala Ala Pro Ser Val
115 120 125

Phe Ile Phe Pro Pro Ser Asp Glu Gln Leu Lys Ser Gly Thr Ala Ser
130 135 140

Val Val Cys Leu Leu Asn Asn Phe Tyr Pro Arg Glu Ala Lys Val Gln
145 150 155 160

Trp Lys Val Asp Asn Ala Leu Gln Ser Gly Asn Ser Gln Glu Ser Val
165 170 175

Thr Glu Gln Asp Ser Lys Asp Ser Thr Tyr Ser Leu Ser Ser Thr Leu
180 185 190

Thr Leu Ser Lys Ala Asp Tyr Glu Lys His Lys Val Tyr Ala Cys Glu
195 200 205

Val Thr His Gln Gly Leu Ser Ser Pro Val Thr Lys Ser Phe Asn Arg
210 215 220

Gly Glu Cys
225

<210> SEQ ID NO 26
<211> LENGTH: 348
<212> TYPE: PRT
<213> ORGANISM: Artificial
<220> FEATURE:
<223> OTHER INFORMATION: Synthetic polypeptide 1214-H

<400> SEQUENCE: 26

Glu Val Gln Leu Val Glu Ser Gly Gly Glu Leu Val Gln Ala Gly Gly
1 5 10 15

Ser Leu Arg Leu Ser Cys Ala Ala Ser Gly Leu Thr Phe Ser Ser Tyr
20 25 30

Asn Met Gly Trp Phe Arg Arg Ala Pro Gly Lys Glu Arg Glu Phe Val
35 40 45

Ala Ser Ile Thr Trp Ser Gly Arg Asp Thr Phe Tyr Ala Asp Ser Val

-continued

```
    50                  55                  60

Lys Gly Arg Phe Thr Ile Ser Arg Asp Asn Ala Lys Asn Thr Val Tyr
65                  70                  75                  80

Leu Gln Met Ser Ser Leu Lys Pro Glu Asp Thr Ala Val Tyr Tyr Cys
                85                  90                  95

Ala Ala Asn Pro Trp Pro Val Ala Ala Pro Arg Ser Gly Thr Tyr Trp
            100                 105                 110

Gly Gln Gly Thr Gln Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr Glu Val Gln Leu Val Glu Ser Gly Gly Gly Phe Val
225                 230                 235                 240

Gln Ala Gly Glu Ser Leu Thr Leu Ser Cys Thr Ser Ser Thr Leu Thr
                245                 250                 255

Phe Thr Pro Tyr Arg Met Ala Trp Tyr Arg Gln Ala Pro Gly Lys Gln
            260                 265                 270

Arg Asp Leu Val Ala Asp Ile Ser Ser Gly Asp Gly Arg Thr Thr Asn
        275                 280                 285

Tyr Ala Asp Phe Ala Lys Gly Arg Phe Thr Ile Ser Arg Asp Asn Ile
    290                 295                 300

Lys Asn Thr Val Phe Leu Arg Met Thr Asn Leu Lys Pro Glu Asp Thr
305                 310                 315                 320

Ala Val Tyr Tyr Cys Asn Thr Phe Val Ser Phe Val Gly Ile Ala Arg
                325                 330                 335

Ser Trp Gly Gln Gly Thr Gln Val Thr Val Ser Ser
            340                 345


<210> SEQ ID NO 27
<211> LENGTH: 227
<212> TYPE: PRT
<213> ORGANISM: Artificial
<220> FEATURE:
<223> OTHER INFORMATION: Synthetic polypeptide 1215-L

<400> SEQUENCE: 27

Glu Val Gln Leu Val Glu Ser Gly Gly Gly Phe Val Gln Ala Gly Glu
1               5                   10                  15

Ser Leu Thr Leu Ser Cys Thr Ser Ser Thr Leu Thr Phe Thr Pro Tyr
            20                  25                  30

Arg Met Ala Trp Tyr Arg Gln Ala Pro Gly Lys Gln Arg Asp Leu Val
        35                  40                  45

Ala Asp Ile Ser Ser Gly Asp Gly Arg Thr Thr Asn Tyr Ala Asp Phe
    50                  55                  60

Ala Lys Gly Arg Phe Thr Ile Ser Arg Asp Asn Ile Lys Asn Thr Val
```

-continued

```
65                  70                  75                  80

Phe Leu Arg Met Thr Asn Leu Lys Pro Glu Asp Thr Ala Val Tyr Tyr
                85                  90                  95

Cys Asn Thr Phe Val Ser Phe Val Gly Ile Ala Arg Ser Trp Gly Gln
            100                 105                 110

Gly Thr Gln Val Thr Val Ser Ser Arg Thr Val Ala Ala Pro Ser Val
        115                 120                 125

Phe Ile Phe Pro Pro Ser Asp Glu Gln Leu Lys Ser Gly Thr Ala Ser
    130                 135                 140

Val Val Cys Leu Leu Asn Asn Phe Tyr Pro Arg Glu Ala Lys Val Gln
145                 150                 155                 160

Trp Lys Val Asp Asn Ala Leu Gln Ser Gly Asn Ser Gln Glu Ser Val
                165                 170                 175

Thr Glu Gln Asp Ser Lys Asp Ser Thr Tyr Ser Leu Ser Ser Thr Leu
            180                 185                 190

Thr Leu Ser Lys Ala Asp Tyr Glu Lys His Lys Val Tyr Ala Cys Glu
        195                 200                 205

Val Thr His Gln Gly Leu Ser Ser Pro Val Thr Lys Ser Phe Asn Arg
    210                 215                 220

Gly Glu Cys
225


<210> SEQ ID NO 28
<211> LENGTH: 345
<212> TYPE: PRT
<213> ORGANISM: Artificial
<220> FEATURE:
<223> OTHER INFORMATION: Synthetic polypeptide 1215-L

<400> SEQUENCE: 28

Glu Val Gln Leu Val Glu Ser Gly Gly Gly Leu Val Gln Pro Gly Glu
1               5                   10                  15

Ser Leu Thr Leu Ser Cys Val Val Ala Gly Ser Ile Phe Ser Phe Ala
            20                  25                  30

Met Ser Trp Tyr Arg Gln Ala Pro Gly Lys Glu Arg Glu Leu Val Ala
        35                  40                  45

Arg Ile Gly Ser Asp Asp Arg Val Thr Tyr Ala Asp Ser Val Lys Gly
    50                  55                  60

Arg Phe Thr Ile Ser Arg Asp Asn Ile Lys Arg Thr Ala Gly Leu Gln
65                  70                  75                  80

Met Asn Ser Leu Lys Pro Glu Asp Thr Ala Val Tyr Tyr Cys Asn Ala
                85                  90                  95

Gln Thr Asp Leu Arg Asp Trp Thr Val Arg Glu Tyr Trp Gly Gln Gly
            100                 105                 110

Thr Gln Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
```

-continued

```
        195                 200                 205

Ser Asn Thr Lys Val Asp Lys Lys Val Glu Pro Lys Ser Cys Asp Lys
    210                 215                 220

Thr Glu Val Gln Leu Val Glu Ser Gly Gly Gly Phe Val Gln Ala Gly
225                 230                 235                 240

Glu Ser Leu Thr Leu Ser Cys Thr Ser Ser Thr Leu Thr Phe Thr Pro
                245                 250                 255

Tyr Arg Met Ala Trp Tyr Arg Gln Ala Pro Gly Lys Gln Arg Asp Leu
            260                 265                 270

Val Ala Asp Ile Ser Ser Gly Asp Gly Arg Thr Thr Asn Tyr Ala Asp
        275                 280                 285

Phe Ala Lys Gly Arg Phe Thr Ile Ser Arg Asp Asn Ile Lys Asn Thr
    290                 295                 300

Val Phe Leu Arg Met Thr Asn Leu Lys Pro Glu Asp Thr Ala Val Tyr
305                 310                 315                 320

Tyr Cys Asn Thr Phe Val Ser Phe Val Gly Ile Ala Arg Ser Trp Gly
                325                 330                 335

Gln Gly Thr Gln Val Thr Val Ser Ser
            340                 345
```